(12) United States Patent
Yasuma et al.

(10) Patent No.: US 8,492,405 B2
(45) Date of Patent: Jul. 23, 2013

(54) GLUCOKINASE-ACTIVATING FUSED HETEROCYCLIC COMPOUNDS AND METHODS OF TREATING DIABETES AND OBESITY

(75) Inventors: Tsuneo Yasuma, Osaka (JP); Yasufumi Miyamoto, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 47 days.

(21) Appl. No.: 12/311,892

(22) PCT Filed: Oct. 17, 2007

(86) PCT No.: PCT/JP2007/070228
§ 371 (c)(1),
(2), (4) Date: Jul. 15, 2009

(87) PCT Pub. No.: WO2008/047821
PCT Pub. Date: Apr. 24, 2008

(65) Prior Publication Data
US 2010/0184794 A1    Jul. 22, 2010

(30) Foreign Application Priority Data
Oct. 18, 2006    (JP) .................................. 2006-284418

(51) Int. Cl.
| A01N 43/52 | (2006.01) |
| A01N 43/78 | (2006.01) |
| A01N 43/40 | (2006.01) |
| A01N 43/82 | (2006.01) |
| A61K 31/415 | (2006.01) |
| A61K 31/425 | (2006.01) |
| A61K 31/445 | (2006.01) |
| A61K 31/41 | (2006.01) |
| C07D 261/20 | (2006.01) |

(52) U.S. Cl.
USPC ........... 514/321; 514/363; 514/365; 514/393; 546/198

(58) Field of Classification Search
None
See application file for complete search history.

(56) References Cited

U.S. PATENT DOCUMENTS

| 6,399,601 | B1 | 6/2002 | Du Bois |
| 2003/0004162 | A1 | 1/2003 | Treadway |
| 2003/0232875 | A1 | 12/2003 | Bartlett et al. |
| 2004/0048878 | A1 | 3/2004 | Cai et al. |
| 2004/0142938 | A1 | 7/2004 | Sher et al. |
| 2005/0054696 | A1 | 3/2005 | Nakamura et al. |
| 2006/0223799 | A1 * | 10/2006 | Crew et al. ................ 514/234.2 |
| 2008/0058395 | A1 | 3/2008 | Heffernan et al. |
| 2010/0022612 | A1 | 1/2010 | Dorsey et al. |
| 2010/0029741 | A1 | 2/2010 | Dorsey et al. |

FOREIGN PATENT DOCUMENTS

| EP | 1 088 824 | 4/2001 |
| EP | 1 136 071 | 9/2001 |
| EP | 1 391 460 | 2/2004 |
| EP | 1 702 919 | 9/2006 |
| JP | 4-204532 | 7/1992 |
| JP | 2001-131181 | 5/2001 |
| JP | 2001-302546 | 10/2001 |
| JP | 2001-333778 | 12/2001 |
| JP | 2003-201279 | 7/2003 |
| JP | 2004-508376 | 3/2004 |
| JP | 2004-196702 | 7/2004 |
| JP | 2005-537333 | 12/2005 |
| WO | 99/40914 | 8/1999 |
| WO | 02/20530 | 3/2002 |
| WO | 03/091213 | 11/2003 |
| WO | 2004/002481 | 1/2004 |
| WO | 2004/022537 | 3/2004 |
| WO | WO 2004/021999 | * 3/2004 |
| WO | 2004/113345 | 12/2004 |
| WO | 2005/063738 | 7/2005 |
| WO | 2006/077412 | 7/2006 |
| WO | 2006/112549 | 10/2006 |
| WO | 2007/096334 | 8/2007 |
| WO | WO 2007/096334 | * 8/2007 |
| WO | 2008/005456 | 1/2008 |
| WO | WO 2008/089453 | * 7/2008 |

OTHER PUBLICATIONS

Stella et al. (Prodrugs: Challenges and Rewards, Part 1, 2007).*
Park, KS. "Prevention of type 2 diabetes mellitus from the viewpoint of genetics." Diabetes Research and Clinical Practice, 2004; 66S:S33-S35.*
International Search Report issued Nov. 27, 2007 in International (PCT) Application No. PCT/JP2007/070228.

(Continued)

*Primary Examiner* — Anna Pagonakis
(74) *Attorney, Agent, or Firm* — Wenderoth, Lind & Ponack, L.L.P.

(57) ABSTRACT

The present invention aims to provide a glucokinase activator useful as a pharmaceutical agent such as an agent for the prophylaxis or treatment of diabetes, obesity and the like, and the like.

A glucokinase activator containing a compound represented by the formula (I):

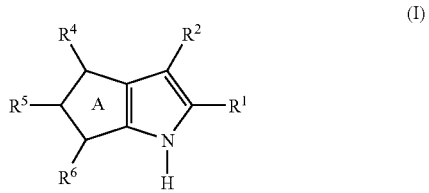

(I)

wherein each symbol is as defined in the specification, or a salt thereof or a prodrug thereof.

9 Claims, No Drawings

OTHER PUBLICATIONS

A. Shafiee et al., "Syntheses of substituted-pyrrolo-[2,3-*d*] imidazoles and substituted-pyrrolo[3,2-*d*]imidazoles", Indian Journal of Chemistry, vol. 36B, pp. 813-815, Sep. 1997.

M. M. Akhavan et al., "Synthesis and antagonistic activity of four new 2-alkyl-*N*-biphenyl fused imidazoles on angiotensin II receptors", IL Farmaco, vol. 58, pp. 1193-1199, 2003.

M. A. Fagan et al., "A New Approach to the Core of Roseophilin", Tetrahedron Letters, vol. 40, pp. 6117-6120, 1999.

D. M. Quizon-Colquitt et al., "Porphyrins with Exocyclic Rings. Part 4[1]. An Improved One Step Synthesis of Cyclopental[*b*]pyrroles [2]", J. Heterocyclic Chem., vol. 30, pp. 477-482, 1993.

European Search Report issued Jan. 3, 2011 in corresponding European Application No. 10 17 4737, in the English language (with letter showing date of receipt).

A. Shafiee et al., "Syntheses of Substituted Pyrrolo[2,3-*d*]imidazole-5-carboxylates and Substitued Pyrrolo[3,2*d*]imidazole-5-carboxylates", Journal of Heterocyclic Chemistry, vol. 39, pp. 367-373 (2002).

M. Farnier et al., "Etude de la decomposition thermique d'azido dithienyl-1,2-ethenes et ethanes", Journal of Heterocyclic Chemistry, vol. 23, pp. 513-516, 1986.

R. Gasparova et al., "Reactions of substituted furo[3,2-*b*]pyrrole-5-carboxhydrazides and their biological activity", Central European Journal of Chemistry, vol. 3, No. 4, pp. 622-646, Dec. 1, 2005.

J. Einsiedel et al., "Benzamide Bioisosteres Incorporating Dihydroheteroazole Substructures: EPC Synthesis and SAR Leading to a Selective Dopamine D4 Receptor Partial Agonist (FAUC 179)", Bioorganic & Medicinal Chemistry Letters, vol. 11, No. 18, pp. 2533-2536, Sep. 17, 2001.

J. Einsiedel et al., "Phenyloxazoles and Phenylthiazo as Benzamide Bioisosteres: Synthesis and Dopamine Receptor Binding Profiles", Bioorganic & Medicinal Chemistry Letters, vol. 10, No. 17, pp. 2041-2044, Sep. 4, 2000.

* cited by examiner

GLUCOKINASE-ACTIVATING FUSED HETEROCYCLIC COMPOUNDS AND METHODS OF TREATING DIABETES AND OBESITY

This application is a U.S. national stage of International Application No. PCT/JP2007/070228 filed Oct. 17, 2007.

TECHNICAL FIELD

The present invention relates to a fused heterocyclic compound having a glucokinase activating action and useful as a therapeutic agent for diabetes and the like. More particularly, the present invention relates to a fused pyrrole compound.

BACKGROUND ART

Glucokinase (sometimes to be abbreviated to as GK in the present specification) (EC2.7.1.1) is one of the four kinds of hexokinases found in mammals, and is also called hexokinase IV. GK is an enzyme that catalyzes the conversion of glucose to glucose-6-phosphate, which is the first step of glycolysis. GK is mainly present in the pancreatic β cell and the liver, and acts in the pancreatic β cell as a sensor of extracellular glucose concentration that defines the glucose-stimulated insulin secretion. In the liver, the enzyme reaction of GK becomes a rate determining factor and regulates glycogen synthesis and glycolysis. The three hexokinases (I, II, III) other than GK reach the maximum enzyme activity at a glucose concentration of 1 mM or below. In contrast, GK shows low affinity for glucose and has a Km value of 8-15 mM which is close to a physiological blood glucose level. Accordingly, GK-mediated promotion of intracellular glucose metabolism occurs, which corresponds to blood glucose changes from normal blood glucose (5 mM) to postprandial hyperglycemia (10-15 mM).

The hypothesis proposed by Matschinsky et al. in 1984 that GK acts as a glucose sensor in the pancreatic β cell and hepatocytes has been demonstrated by the analysis of glucokinase gene manipulation mouse in recent years (see non-patent references 1-5). That is, GK heterozygous knockout mouse, showed a hyperglycemic condition, and further, a disordered glucose-stimulated insulin secretion response. GK homozygous knockout mouse dies shortly after birth with manifestations of marked hyperglycemia and urinary sugar. On the other hand, GK overexpressed mouse (hetero type) showed decreased blood glucose level, increased blood glucose clearance rate, increased liver glycogen content and the like. From these findings, it has been clarified that GK plays an important role in the systemic glucose homeostasis. In other words, decreased GK activity causes insulin secretion failure and lower liver glucose metabolism, which develops impaired glucose tolerance and diabetes. Conversely, GK activation or increased GK activity due to overexpression causes promoted insulin secretion and promoted liver glucose metabolism, which in turn increases the systemic use of glucose to improve glucose tolerance.

In addition, it has been clarified from the analysis of a report on GK gene abnormality mainly in the family of MODY2 (Maturity Onset Diabetes of the Young) that GK also acts as a glucose sensor in human, and plays a key role in glucose homeostasis (see non-patent reference 6). In GK gene abnormality, due to the decreased affinity of GK for glucose (increased Km value) and decreased Vmax, the blood glucose threshold value of insulin secretion increases and the insulin secretory capacity decreases. In the liver, due to the decreased GK activity, decreased glucose uptake, promoted gluconeogenesis, decreased glycogen synthesis and liver insulin resistance are observed. On the other hand, a family with a mutation increasing the GK activity has also been found. In such family, fasting hypoglycemia associated with increased plasma insulin concentration is observed (see non-patent reference 7).

As mentioned above, GK acts as a glucose sensor in mammals including human, and plays an important role in blood glucose regulation. On the other hand, control of blood glucose utilizing the glucose sensor system of GK is considered to open a new way to treat diabetes in many type 2 diabetes patients. Particularly, since a GK activating substance is expected to show insulin secretagogue action in the pancreatic β cell and glucose uptake promotive action and glucose release suppressive action in the liver, it will be useful as a prophylactic or therapeutic drug for type 2 diabetes.

In recent years, it has been clarified that pancreatic β cell type glucokinase expresses locally in the feeding center (Ventromedial Hypothalamus: VMH) of rat brain. A subset of nerve cell present in VMH is called glucose responsive neuron, and plays an important role in the body weight control. From electrophysiological experiments, the neuron is activated in response to physiological changes in the glucose concentration (5-20 mM). However, since the glucose concentration sensor system of VHM is assumed to have a mechanism mediated by glucokinase as in the case of insulin secretion in the pancreatic β cell, separately from pancreatic β cell and the liver, a pharmaceutical agent capable of activating glucokinase of VHM has a possibility of providing not only a blood glucose corrective effect but also improvement of obesity.

As mentioned above, a GK activator is useful as a prophylactic or therapeutic drug for diabetes and diabetic complications, and further, as a prophylactic or therapeutic drug for obesity.

As a fused pyrrole compound, the following compounds have been reported.

(1) A compound represented by the formula:

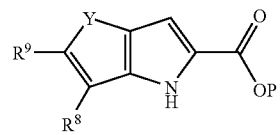

wherein

Y is O or S; P is an alkyl group, an aryl group or a benzyl group; and $R^8$ and $R^9$ are each independently —H, —F, a $C_{1-4}$ alkyl group, a $C_{1-4}$ alkoxy group, —[NR′]SO_2—$C_{1-4}$ alkyl wherein R′ is —H, a $C_{1-4}$ alkyl group and the like has been reported as an synthetic intermediate for a therapeutic drug for histamine $H_4$ receptor-mediated diseases (see patent document 1).

(2) A compound represented by the formula:

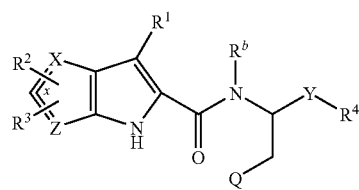

wherein Q is a phenyl group; Z and X are each independently C, CH, CH$_2$, N, O or S; each — is a bond or absent (provided that — is not a bond at the same time); R$^1$ is a hydrogen atom or a halogen atom; each of R$^a$ and R$^b$ is independently a hydrogen atom or —C$_{1-8}$ alkyl; Y is —CH(OH)— or absent; R$^2$ is a hydrogen atom, a halogen atom, —C$_{1-8}$ alkyl and the like; R$^3$ is a hydrogen atom, a halogen atom, —C$_{1-8}$ alkyl, —O—C$_{1-8}$ alkyl, —NH—C$_{1-8}$ alkyl and the like; R$^4$ is —C(=O)A; A is —NR$^d$R$^d$ or

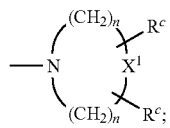

each R$^d$ is independently a hydrogen atom, —C$_{1-8}$ alkyl, —C$_{1-8}$ alkoxy and the like; X$^1$ is —NR$^a$, —CH$_2$—, O or S; each R$^c$ is independently a hydrogen atom, —C(=O)OR$^a$, —OR$^a$, —SR$^a$ or —NR$^a$R$^a$; and n is independently 1 to 3 has been reported as a glycogen phosphorylase inhibitor, and a compound represented by the formula

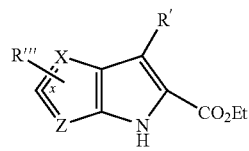

wherein R' and R''' are each independently a hydrogen atom or halide, and other symbols are as defined above, has been reported as a synthetic intermediate therefor (see patent documents 2, 3 and 4).

(3) The following compounds have been reported as angiotensin II antagonists (see non-patent document 8):

methyl 3-{[2'-(methoxycarbonyl)biphenyl-4-yl]methyl}-2-propyl-3,4-dihydropyrrolo[2,3-d]imidazol-5-carboxylate

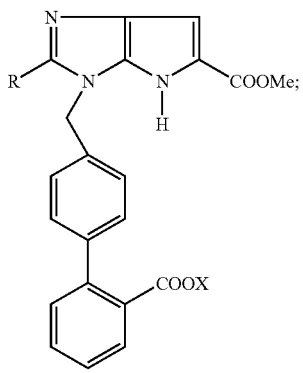

R = n-Pr, X = Me methyl 2-butyl-3-{([2'-(methoxycarbonyl)biphenyl-4-yl]methyl}-3,4-dihydropyrrolo[2,3-d]imidazol-5-carboxylate

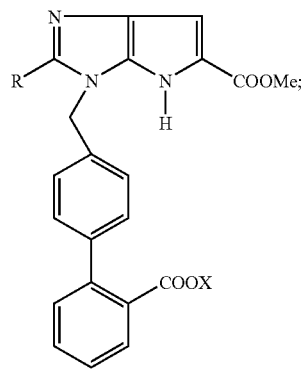

R = n-Bu, X = Me

4'-{[5-(methoxycarbonyl)-2-propylpyrrolo[2,3-d]imidazol-3(4H)-yl]methyl}biphenyl-2-carboxylic acid

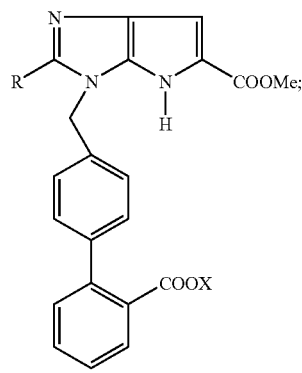

R = n-Pr, X = H and
4'-{[2-butyl-5-(methoxycarbonyl)pyrrolo[2,3-d]imidazol-3(4H)-yl]methyl}biphenyl-2-carboxylic acid

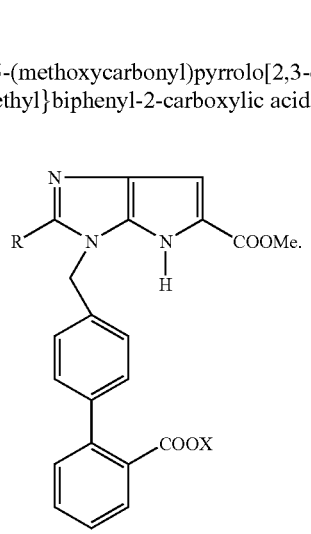

R = n-Bu, X = H (4) The following compounds have been reported as therapeutic drugs for hypertension (see non-patent document 9):
ethyl 3-[4-(ethoxycarbonyl)benzyl]-2-propyl-3,4-dihydropyrrolo[2,3-d]imidazol-5-carboxylate

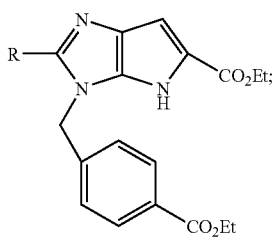

R = n-Pr and
ethyl 2-butyl-3-[4-(ethoxycarbonyl)benzyl]-3,4-dihydropyrrolo[2,3-d]imidazol-5-carboxylate

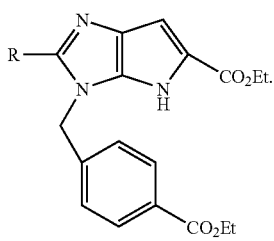

R = n-Bu (5) A compound represented by the formula:

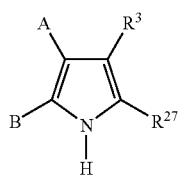

wherein A and B in combination form an optionally substituted 5-membered aromatic ring (containing one or more hetero atoms); $R^{27}$ is —H, —COOH, —C(O)CH$_2$OH, —CONHR$^4$ and the like wherein $R^4$ is —H, an alkyl group and the like; and $R^3$ is —H and the like, specifically, ethyl 3-methyl-3,4-dihydropyrrolo[2,3-d]imidazol-5-carboxylate

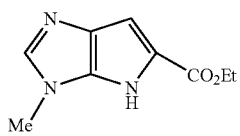

has been reported as a synthetic intermediate for an anti-inflammatory compound (see patent document 5).

(6) The following two compounds have been reported as intermediates for synthesizing porphyrins (see non-patent document 10):

ethyl 3,6-dimethyl-1,4,5,6-tetrahydrocyclopenta[b]pyrrol-2-carboxylate

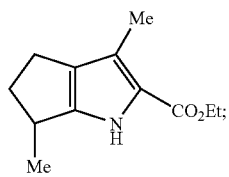 [SMILES: CCOC(=O)c1[nH]c2c(c1C)CCC2C]

and
benzyl 6-(acetoxy)-3-methyl-1,4,5,6-tetrahydrocyclopenta[b]pyrrol-2-carboxylate

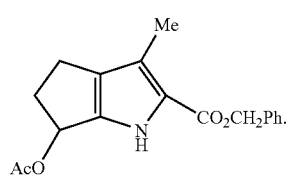

(7) A compound represented by the formula:

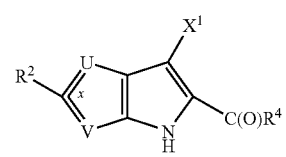

wherein one of U and V is —S— and the other is —C(R$^3$)—; one of R$^2$ and R$^3$ is -D-E (D is a bond, —O—, —CH$_2$— and the like; E is an aryl group and the like) and the other is a hydrogen atom, a halogen atom and the like; R$^4$ is —OR$^{12a}$ or —N(R$^{12b}$)R$^{13b}$; R$^{12a}$, R$^{12b}$ and R$^{13b}$ are each independently a hydrogen atom, an aryl group, a C$_{1-8}$ alkyl group and the like; and X$^1$ is a hydrogen atom, a halogen atom and the like, has been reported as a synthetic intermediate for a therapeutic agent for inflammation (see patent document 6).

(8) A compound represented by the formula:

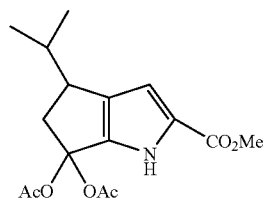 [SMILES: COC(=O)c1cc2c([nH]1)C(OC(C)=O)(OC(C)=O)CC2C(C)C]

has been reported as an intermediate for synthesizing roseophilin (see non-patent document 11).

However, none of the references discloses that a compound represented by the following formula (I) has a glucokinase activating action.
patent document 1: WO 2004/022537
patent document 2: EP-A-1088824
patent document 3: EP-A-1391460
patent document 4: EP-A-1136071
patent document 5: WO 99/40914
patent document 6: WO 2006/077412
non-patent document 1: J. Biol. Chem., 1995, vol. 270, pages 30253-30256
non-patent document 2: J. Biol. Chem., 1997, vol. 272, pages 22564-22569 non-patent document 3: J. Biol. Chem., 1997, vol. 272, pages 22570-22575 non-patent document 4: Nippon Rinsho, 2002, vol. 60, pages 523-534 non-patent document 5: Cell, 1995, vol. 83, pages 69-78 non-patent document 6: Nature, 1992, vol. 356, pages 721-722 non-patent document 7: New England Journal Medicine, 1998, vol. 338, pages 226-230 non-patent document 8: IL FARMACO, 2003, vol. 58, pages 1193-1199 non-patent document 9: Indian Journal of Chemistry, 1997, vol. 36-B, pages 813-815 non-patent document 10: J. Heterocyclic Chem, 1993, vol. 30, pages 447-482 non-patent document 11: Tetrahedron Letters, 1999, vol. 40, pages 6117-6120

DISCLOSURE OF THE INVENTION

Problems to be Solved by the Invention

An object of the present invention is to provide a glucokinase activator which is useful as a pharmaceutical agent such as an agent for the prophylaxis or treatment of diabetes, obesity and the like, and the like.

Means of Solving the Problems

The present inventors have conducted intensive studies and found that a compound represented by the following formula (I) unexpectedly has a superior glucokinase activating action as well as superior properties as a pharmaceutical product such as stability and the like, and can be a safe and useful pharmaceutical agent, which resulted in the completion of the present invention.

Accordingly, the present invention relates to

[1] A compound represented by the formula (I):

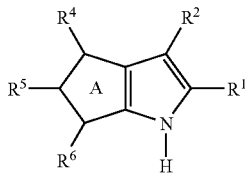

wherein ring A is a 5-membered ring, $R^1$ is an optionally substituted 5- to 7-membered heterocyclic group or —$COR^3$ wherein $R^3$ is an optionally substituted hydrocarbon group, an optionally substituted hydroxy group, an optionally substituted amino group or an optionally substituted heterocyclic group, $R^2$ is a hydrogen atom or a halogen atom, $R^4$, $R^5$ and $R^6$ are each independently a hydrogen atom or a substituent (provided that $R^4$, $R^5$ and $R^6$ are absent when an atom on ring A they are bonded to cannot have a substituent), or a salt thereof (hereinafter sometimes to be abbreviated as compound (I)), or a glucokinase activator comprising a prodrug thereof;

[2] a compound represented by the formula (I):

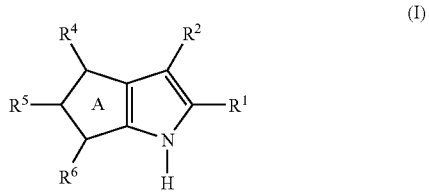

wherein ring A is a 5-membered ring, $R^1$ is an optionally substituted 5- to 7-membered heterocyclic group or —$COR^3$ wherein $R^3$ is an optionally substituted hydrocarbon group, an optionally substituted hydroxy group, an optionally substituted amino group or an optionally substituted heterocyclic group, $R^2$ is a hydrogen atom or a halogen atom, $R^4$, $R^5$ and $R^6$ are each independently a hydrogen atom or a substituent (provided that $R^4$, $R^5$ and $R^6$ are absent when an atom on ring A they are bonded to cannot have a substituent), provided that A) when $R^1$ is —$COR^3$ wherein $R^3$ is as defined above, then $R^6$ is an optionally substituted amino group, an optionally substituted $C_{1-6}$ alkyl group or an optionally substituted hydrocarbon-oxy group, B) when $R^1$ is —$COR^3$ wherein $R^3$ is as defined above and ring A is a thiophene ring or a furan ring, then $R^6$ is an optionally substituted amino group or an optionally substituted hydrocarbon-oxy group (excluding methyl 3-{[2'-(methoxycarbonyl)biphenyl-4-yl]methyl}-2-propyl-3,4-dihydropyrrolo[2,3-d]imidazol-5-carboxylate, methyl 2-butyl-3-{[2'-(methoxycarbonyl)biphenyl-4-yl]methyl}-3,4-dihydropyrrolo[2,3-d]imidazol-5-carboxylate, 4'-{[5-(methoxycarbonyl)-2-propylpyrrolo[2,3-d]imidazol-3(4H)-yl]methyl}biphenyl-2-carboxylic acid, 4'-{[2-butyl-5-(methoxycarbonyl)pyrrolo[2,3-d]imidazol-3(4H)-yl]methyl}biphenyl-2-carboxylic acid, ethyl 3-[4-(ethoxycarbonyl)benzyl]-2-propyl-3,4-dihydropyrrolo[2,3-d]imidazol-5-carboxylate, ethyl 2-butyl-3-[4-(ethoxycarbonyl)benzyl]-3,4-dihydropyrrolo[2,3-d]imidazol-5-carboxylate, ethyl 3-methyl-3,4-dihydropyrrolo[2,3-d]imidazol-5-carboxylate, and ethyl 3,6-dimethyl-1,4,5,6-tetrahydrocyclopenta[b]pyrrol-2-carboxylate), or a salt thereof;

[3] the compound of the above-mentioned [2], wherein ring A is 5-membered aromatic heterocycle;

[4] the compound of the above-mentioned [2], wherein $R^1$ is an optionally substituted 5- to 7-membered heterocyclic group;

[5] the compound of the above-mentioned [2], wherein $R^2$ is a hydrogen atom;

[6] the compound of the above-mentioned [2], wherein $R^4$ is an optionally substituted hydrocarbon group;

[7] the compound of the above-mentioned [2], wherein $R^5$ is a hydrogen atom or an optionally substituted hydrocarbon group;

[8] the compound of the above-mentioned [2], wherein $R^6$ is an optionally substituted amino group;

[9] ethyl 3-benzyl-2-methyl-3,4-dihydropyrrolo[2,3-d]imidazol-5-carboxylate,

N-[5-(4,5-dihydro-1,3-thiazol-2-yl)-2-methyl-4H-thieno[3,2-b]pyrrol-3-yl]-N-methylthiophen-2-sulfonamide, N-[5-(8-acetyl-1-thia-3,8-diazaspiro[4.5]deca-2-en-2-yl)-2-methyl-4H-thieno[3,2-b]pyrrol-3-yl]-N-methylthiophen-2-sulfonamide, N-[5-(4,5-dihydro-1,3-thiazol-2-yl)-1-ethyl-1,4-dihydropyr-rolo[3,2-b]pyrrol-3-yl]-N-methylthiophen-2-sulfonamide or ethyl 4-benzyl-6-[methyl(2-thienylsulfonyl)amino]-1,4-di-hydropyrrolo[3,2-b]pyrrol-2-carboxylate, or a salt thereof;

[10] a prodrug of the compound of the above-mentioned [2];

[11] a pharmaceutical agent comprising the compound of the above-mentioned [2] or a prodrug thereof;

[12] the pharmaceutical agent of the above-mentioned [11], which is an agent for the prophylaxis or treatment of diabetes or obesity;

[13] a method of preventing or treating diabetes or obesity in a mammal, comprising administering the compound of the above-mentioned [2] or a prodrug thereof to the mammal;

[14] use of the compound of the above-mentioned [2] or a prodrug thereof for the production of an agent for the prophylaxis or treatment of diabetes or obesity; and the like.

Effect of the Invention

Since compound (I) of the present invention has a superior glucokinase activating action, it is useful as a pharmaceutical agent such as an agent for the prophylaxis or treatment of diabetes, obesity and the like.

DETAILED DESCRIPTION OF THE INVENTION

Unless otherwise specified, as the "halogen atom" in the present specification, fluorine atom, chlorine atom, bromine atom or iodine atom can be mentioned.

Unless otherwise specified, as the "$C_{1-3}$ alkylenedioxy group" in the present specification, methylenedioxy, ethylenedioxy or the like can be mentioned.

Unless otherwise specified, as the "$C_{1-6}$ alkyl group" in the present specification, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl or the like can be mentioned.

Unless otherwise specified, as the "$C_{1-6}$ alkoxy group" in the present specification, methoxy, ethoxy, propoxy, isopropoxy, butoxy, isobutoxy, sec-butoxy, tert-butoxy or the like can be mentioned.

Unless otherwise specified, as the "$C_{1-6}$ alkoxy-carbonyl group" in the present specification, methoxycarbonyl, ethoxycarbonyl, propoxycarbonyl, tert-butoxycarbonyl or the like can be mentioned.

Unless otherwise specified, as the "$C_{1-6}$ alkyl-carbonyl group" in the present specification, acetyl, propanoyl, butanoyl, isobutanoyl, pentanoyl, isopentanoyl, hexanoyl or the like can be mentioned.

Each symbol in the formula (I) is described in detail in the following.

$R^1$ is an optionally substituted 5- to 7-membered heterocyclic group or —$COR^3$ wherein $R^3$ is an optionally substituted hydrocarbon group, an optionally substituted hydroxy group, an optionally substituted amino group or an optionally substituted heterocyclic group.

As the "hydrocarbon group" of the "optionally substituted hydrocarbon group" for $R^3$, for example, a $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{4-10}$ cycloalkadienyl group, a $C_{8-14}$ aryl group, a $C_{7-13}$ aralkyl group, a $C_{8-13}$ arylalkenyl group, a $C_{3-10}$ cycloalkyl-$C_{1-6}$ alkyl group and the like can be mentioned.

As used herein, as the $C_{1-10}$ alkyl group, for example, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like can be mentioned.

As the $C_{2-10}$ alkenyl group, for example, ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like can be mentioned.

As the $C_{2-10}$ alkynyl group, for example, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like can be mentioned.

As the $C_{3-10}$ cycloalkyl group, for example, cyclopropyl, cyclobutyl, cyclopentyl, cyclohexyl, cycloheptyl, cyclooctyl and the like can be mentioned.

As the $C_{3-10}$ cycloalkenyl group, for example, 2-cyclopenten-1-yl, 3-cyclopenten-1-yl, 2-cyclohexen-1-yl, 3-cyclohexen-1-yl and the like can be mentioned.

As the $C_{4-10}$ cycloalkadienyl group, for example, 2,4-cyclopentadien-1-yl, 2,4-cyclohexadien-1-yl, 2,5-cyclohexadien-1-yl and the like can be mentioned.

The above-mentioned $C_{3-10}$ cycloalkyl group, $C_{3-10}$ cycloalkenyl group and $C_{4-10}$ cycloalkadienyl are each optionally condensed with a benzene ring to form a fused cyclic group, and as the fused cyclic group, for example, indanyl, dihydronaphthyl, tetrahydronaphthyl, fluorenyl and the like can be mentioned. In addition, as the aforementioned hydrocarbon group, a cross-linked hydrocarbon group such as bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl, norbornanyl and the like, and the like can also be mentioned.

As the $C_{6-14}$ aryl group, for example, phenyl, naphthyl, anthryl, phenanthryl, acenaphthylenyl, biphenylyl and the like can be mentioned.

As the $C_{7-13}$ aralkyl group, for example, benzyl, phenethyl, naphthylmethyl, biphenylylmethyl and the like can be mentioned.

As the $C_{8-13}$ arylalkenyl group, for example, styryl and the like can be mentioned.

As the $C_{3-10}$ cycloalkyl-$C_{1-6}$ alkyl group, for example, cyclohexylmethyl and the like can be mentioned.

The $C_{1-10}$ alkyl group, $C_{2-10}$ alkenyl group and $C_{2-10}$ alkynyl group exemplified as the aforementioned "hydrocarbon group" optionally have 1 to 3 substituents at substitutable positions.

As such substituents, for example, (1) a $C_{3-10}$ cycloalkyl group (e.g., cyclopropyl, cyclohexyl);

(2) a $C_{6-14}$ aryl group (e.g., phenyl, naphthyl) optionally substituted by 1 to 3 substituents selected from (a) a $C_{1-6}$ alkyl group optionally substituted by 1 to 3 halogen atoms, (b) a hydroxy group, (c) a $C_{1-6}$ alkoxy group and (d) a halogen atom;

(3) an aromatic heterocyclic group (e.g., thienyl, furyl, pyridyl, oxazolyl, thiazolyl, tetrazolyl, oxadiazolyl, pyrazinyl, quinolyl, indolyl) optionally substituted by 1 to 3 substituents selected from (a) a $C_{1-6}$ alkyl group optionally substituted by 1 to 3 halogen atoms, (b) a hydroxy group, (c) a $C_{1-6}$ alkoxy group and (d) a halogen atom;

(4) a non-aromatic heterocyclic group (e.g., tetrahydrofuryl, morpholinyl, thiomorpholinyl, piperidinyl, pyrrolidinyl, piperazinyl, dioxolyl, dioxolanyl, 1,3-dihydro-2-benzofuranyl, thiazolidinyl, thiazolinyl) optionally substituted by 1 to 3 substituents selected from (a) a $C_{1-6}$ alkyl group optionally substituted by 1 to 3 halogen atoms, (b) a hydroxy group, (c) a $C_{1-6}$ alkoxy group, (d) an oxo group, (e) a halogen atom and (f) a $C_{7-20}$ aralkylthio group (e.g., benzylthio, tritylthio);

(5) an amino group optionally mono- or di-substituted by substituent(s) selected from
(a) a $C_{1-6}$ alkyl group,
(b) a $C_{1-6}$ alkyl-carbonyl group,
(c) a $C_{1-6}$ alkoxy-carbonyl group,
(d) a $C_{6-14}$ aryl-carbonyl group (e.g., benzoyl),
(e) a $C_{7-13}$ aralkyl-carbonyl group (e.g., benzylcarbonyl, phenethylcarbonyl),
(f) a carbamoyl group optionally mono- or di-substituted by substituent(s) selected from a $C_{1-6}$ alkyl group, a $C_{6-14}$ aryl group and a $C_{7-13}$ aralkyl group (e.g., carbamoyl, methylcarbamoyl, benzylcarbamoyl, dimethylcarbamoyl),
(g) a $C_{1-6}$ alkylsulfonyl group (e.g., methylsulfonyl, ethylsulfonyl, isopropylsulfonyl),
(h) a $C_{6-14}$ arylsulfonyl group (e.g., benzenesulfonyl, toluenesulfonyl, 1-naphthalenesulfonyl, 2-naphthalenesulfonyl), and
(i) a $C_{7-13}$ aralkylsulfonyl group (e.g., benzylsulfonyl);
(6) an amidino group;
(7) a $C_{1-6}$ alkyl-carbonyl group optionally substituted by 1 to 3 is halogen atoms;
(8) a $C_{1-6}$ alkoxy-carbonyl group optionally substituted by 1 to 3 halogen atoms;
(9) an aromatic heterocyclyl-carbonyl group (e.g., thienylcarbonyl, indolylcarbonyl) optionally substituted by 1 to 3 amino groups (the amino group is each optionally mono- or di-substituted by substituent(s) selected from a $C_{1-6}$ alkyl group and an aromatic heterocyclyl-sulfonyl group (e.g., thienylsulfonyl));
(10) a non-aromatic heterocyclyl-carbonyl group (e.g., morpholinylcarbonyl);
(11) a $C_{1-6}$ alkylsulfonyl group (e.g., methylsulfonyl) optionally substituted by 1 to 3 halogen atoms;
(12) a carbamoyl group optionally mono- or di-substituted by substituent(s) selected from (a) a $C_{1-6}$ alkyl group optionally substituted by 1 to 3 halogen atoms, (b) a $C_{6-14}$ aryl group (e.g., phenyl), (c) a $C_{7-13}$ aralkyl group (e.g., benzyl) and (d) an aromatic heterocyclyl-$C_{1-6}$ alkyl group (e.g., furfuryl);
(13) a thiocarbamoyl group optionally mono- or di-substituted by $C_{1-6}$ alkyl group(s) optionally substituted by 1 to 3 halogen atoms;
(14) a sulfamoyl group optionally mono- or di-substituted by a $C_{1-6}$ alkyl group optionally substituted by 1 to 3 halogen atoms;
(15) a carboxy group;
(16) a hydroxy group;
(17) a $C_{1-6}$ alkoxy group optionally substituted by 1 to 3 substituents selected from (a) a halogen atom, (b) a carboxy group, (c) a $C_{1-6}$ alkoxy group and (d) a $C_{1-6}$ alkoxy-carbonyl group;
(18) a $C_{2-6}$ alkenyloxy group (e.g., ethenyloxy) optionally substituted by 1 or 3 halogen atoms;
(19) a $C_{3-10}$ cycloalkyloxy group (e.g., cyclohexyloxy);
(20) a $C_{7-13}$ aralkyloxy group (e.g., benzyloxy) optionally substituted by 1 or 3 halogen atoms;
(21) a $C_{6-14}$ aryloxy group (e.g., phenyloxy, naphthyloxy);
(22) a $C_{1-6}$ alkyl-carbonyloxy group (e.g., acetyloxy, tert-butylcarbonyloxy);
(23) a mercapto group;
(24) a $C_{1-6}$ alkylthio group (e.g., methylthio, ethylthio) optionally substituted by 1 to 3 substituents selected from a halogen atom and a $C_{6-14}$ aryl group;
(25) a $C_{6-14}$ arylthio group (e.g., phenylthio, naphthylthio);
(26) an aromatic heterocycle-thio group (e.g., tetrazolylthio) optionally substituted by 1 to 3 $C_{1-6}$ alkyl groups;
(27) a sulfo group;
(28) a cyano group;
(29) an azido group;
(30) a nitro group;
(31) a nitroso group;
(32) a halogen atom;
(33) a $C_{1-6}$ alkylsulfinyl group (e.g., methylsulfinyl);
(34) an oxo group;
(35) a $C_{3-10}$ cycloalkyl-$C_{1-6}$alkyloxy group (e.g., cyclopropylmethyloxy);
(36) a $C_{1-3}$ alkylenedioxy group;
(37) an aromatic heterocyclyl-carbonylthio group (e.g., indolylcarbonylthio) optionally substituted by 1 to 3 amino groups (the amino group is each optionally mono- or di-substituted by substituent(s) selected from a $C_{1-6}$ alkyl group and an aromatic heterocyclyl-sulfonyl group (e.g., thienylsulfonyl));
(38) a formyl group;
and the like can be mentioned.

The $C_{3-10}$ cycloalkyl group, $C_{3-10}$ cycloalkenyl group, $C_{4-10}$ cycloalkadienyl group, $C_{6-14}$ aryl group, $C_{7-13}$ aralkyl group, $C_{8-13}$ arylalkenyl group and $C_{3-10}$ cycloalkyl-$C_{1-6}$ alkyl group exemplified as the aforementioned "hydrocarbon group" optionally have 1 to 3 substituents at substitutable positions.

As such substituents, for example,
(1) those exemplified as the substituents of the aforementioned $C_{1-10}$ alkyl group and the like;
(2) a $C_{1-6}$ alkyl group optionally substituted by 1 to 3 substituents selected from
(i) a halogen atom,
(ii) a carboxy group,
(iii) a hydroxy group,
(iv) a $C_{1-6}$ alkoxy group optionally substituted by 1 to 3 substituents selected from a carboxy group and a $C_{1-6}$ alkoxy-carbonyl group,
(v) a $C_{1-6}$ alkoxy-carbonyl group,
(vi) a $C_{1-6}$ alkyl-carbonyloxy group (e.g., acetyloxy, tert-butylcarbonyloxy),
(vii) a carbamoyl group optionally mono- or di-substituted by substituent(s) selected from a $C_{1-6}$ alkylsulfonyl group and an amino group,
(viii) a aromatic heterocyclic group (e.g., thienyl, tetrazolyl),
(ix) a non-aromatic heterocyclic group (e.g., piperidino, piperazinyl, morpholinyl, dihydrooxadiazolyl, hexahydropyrazinooxazinyl (e.g., hexahydropyrazino[2,1-c][1,4]oxazinyl)) optionally substituted by 1 to 3 substituents selected from a $C_{1-6}$ alkyl-carbonyl group and an oxo group,
(x) an amino group optionally mono- or di-substituted by a $C_{1-6}$ alkyl group(s) (the $C_{1-6}$ alkyl group is each optionally substituted by 1 to 3 substituents selected from a non-aromatic heterocyclic group (e.g., morpholinyl), a $C_{1-6}$ alkoxy group and a $C_{1-6}$ alkylsulfonyl group),
(xi) a $C_{1-6}$ alkylsulfonyl group optionally substituted by 1 to 3 carboxy groups,
(xii) a $C_{1-6}$ alkylthio group optionally substituted by 1 to 3 substituents selected from a carboxy group, a $C_{1-6}$ alkoxy-carbonyl group, a hydroxy group and a carbamoyl group,
(xiii) a phosphono group optionally mono- or di-substituted by $C_{1-6}$ alkyl group(s), (xiv) a non-aromatic heterocyclyl-carbonyl group (e.g., morpholinylcarbonyl),
(xv) a cyano group, and
(xvi) a $C_{6-14}$ aryloxy group optionally substituted by 1 to 3 substituents selected from a carboxy group and a $C_{1-6}$ alkoxy-carbonyl group;
(3) a $C_{2-6}$ alkenyl group (e.g., ethenyl, 1-propenyl) optionally substituted by from 1 to 3 substituents selected from a halogen atom, a carboxy group, a $C_{1-6}$ alkoxy-carbonyl group and a carbamoyl group;
(4) a $C_{7-13}$ aralkyl group (e.g., benzyl) optionally substituted 1 to 3 substituents selected from a $C_{1-6}$ alkyl group optionally substituted by 1 to 3 halogen atoms, a hydroxy group, a $C_{1-6}$ alkoxy group and a halogen atom;
and the like can be mentioned.

As the "heterocyclic group" of the "optionally substituted heterocyclic group" for $R^3$, an aromatic heterocyclic group and a non-aromatic heterocyclic group can be mentioned.

As used herein, as the aromatic heterocyclic group, for example, a 4- to 7-membered (preferably 5- or 6-membered) monocyclic aromatic heterocyclic group containing, as a ring-constituting atom besides carbon atoms, 1 to 4 heteroatoms selected from an oxygen atom, a sulfur atom and a nitrogen atom, and a fused aromatic heterocyclic group can be mentioned.

The fused aromatic heterocyclic group include a group derived from a fused ring wherein a ring constituting the 4- to 7-membered monocyclic aromatic heterocyclic group, and 1 or 2 rings selected from a 5- or 6-membered aromatic heterocycle containing 1 or 2 nitrogen atoms, a 5-membered aromatic heterocycle containing one sulfur atom and a benzene ring are condensed, and the like.

Preferable examples of the aromatic heterocyclic group include monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 4-isothiazolyl), oxazolyl (e.g., 2-oxazolyl, 4-oxazolyl, 5-oxazolyl), isoxazolyl, oxadiazolyl (e.g., 1,2,4-oxadiazol-3-yl, 1,2,4-oxadiazol-5-yl, 1,3,4-oxadiazol-2-yl), thiadiazolyl (e.g., 1,3,4-thiadiazol-2-yl, 1,2,4-thiadiazol-3-yl, 1,2,4-thiadiazol-5-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like;
fused aromatic heterocyclic groups such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuryl (e.g., 2-benzofuryl, 3-benzofuryl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), imidazopyrazinyl (e.g., 1H-imidazo[4,5-b]pyrazin-2-yl), imidazothiazolyl (e.g., imidazo[2,1-b]thiazol-5-yl), pyrazolopyridinyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like;
and the like.

The non-aromatic heterocyclic group includes a 4- to 7-membered (preferably 5- or 6-membered) monocyclic non-aromatic heterocyclic group containing, as a ring-constituting atom besides carbon atoms, 1 to 4 heteroatoms selected from an oxygen atom, a sulfur atom and a nitrogen atom, and a fused non-aromatic heterocyclic group.

The fused non-aromatic heterocyclic group includes a group derived from a fused ring wherein a ring constituting the 4- to 7-membered monocyclic non-aromatic heterocyclic group, and 1 or 2 rings selected from a 5- or 6-membered heterocycle containing 1 or 2 nitrogen atoms, a 5-membered heterocycle containing one sulfur atom and a benzene ring are condensed, and the like.

Preferable examples of the non-aromatic heterocyclic group include monocyclic non-aromatic heterocyclic groups such as pyrrolidinyl (e.g., 1-pyrrolidinyl), piperidinyl (e.g., piperidino, 2-piperidinyl, 3-piperidinyl, 4-piperidinyl), morpholinyl (e.g., morpholino), thiomorpholinyl (e.g., thiomorpholino), piperazinyl (e.g., 1-piperazinyl, 2-piperazinyl, 3-piperazinyl), hexamethyleneiminyl (e.g., hexamethyleneimin-1-yl), oxazolidinyl (e.g., oxazolidin-2-yl), thiazolidinyl (e.g., thiazolidin-2-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), thiooxooxazolidinyl (e.g., 2-thioxo-1,3-oxazolidin-5-yl), pyranyl (e.g., 4-pyranyl), tetrahydropyranyl (e.g., 4-tetrahydropyranyl), thiopyranyl (e.g., 4-thiopyranyl), tetrahydrothiopyranyl (e.g., 4-tetrahydrothiopyranyl), 1-oxidotetrahydrothiopyranyl (e.g., 1-oxidotetrahydrothiopyran-4-yl), 1,1-dioxidotetrahydrothiopyranyl (e.g., 1,1-dioxidotetrahydrothiopyran-4-yl), pyrazolidinyl (e.g., pyrazolidin-1-yl), tetrahydropyrimidinyl, dioxanyl (e.g., 1,3-dioxan-2-yl, 1,3-dioxan-4-yl, 1,3-dioxan-5-yl, 1,4-dioxan-2-yl), dioxenyl (e.g., 4H-1,3-dioxin-2-yl, 4H-1,3-dioxin-4-yl, 4H-1,3-dioxin-5-yl, 4H-1,3-dioxin-6-yl, 2,3-dihydro-1,4-dioxin-2-yl, 2,3-dihydro-1,4-dioxin-5-yl) and the like; fused non-aromatic heterocyclic groups such as dihydroindolyl (e.g., 2,3-dihydro-1H-isoindol-1-yl), dihydroisoindolyl (e.g., 1,3-dihydro-2H-isoindol-2-yl), dihydrobenzofuranyl (e.g., 2,3-dihydro-1-benzofuran-5-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), tetrahydrobenzofuranyl (e.g., 4,5,6,7-tetrahydro-1-benzofuran-3-yl), chromenyl (e.g., 4H-chromen-2-yl, 2H-chromen-3-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl), hexahydropyrazinooxazinyl (e.g., hexahydropyrazino[2,1-c][1,4]oxazinyl) and the like fused non-aromatic heterocyclic group;
and the like.

The "heterocyclic group" of the aforementioned "optionally substituted heterocyclic group" optionally has 1 to 3 substituents at substitutable positions. As such substituents, those exemplified as the substituents which the $C_{3-10}$ cycloalkyl group and the like exemplified as the "hydrocarbon group" of the "optionally substituted hydrocarbon group" for $R^3$ optionally has, can be mentioned.

The "optionally substituted hydroxy group" for $R^3$ includes a hydroxyl group optionally substituted by a substituent selected from an optionally substituted hydrocarbon group, an optionally substituted $C_{1-6}$ alkyl-carbonyl group, an optionally substituted heterocyclic group and the like.

Here, each of the "optionally substituted hydrocarbon group" and "optionally substituted heterocyclic group" include those similar to the "optionally substituted hydrocarbon group" for $R^3$ and the "optionally substituted heterocyclic group" for $R^3$, respectively.

The aforementioned $C_{1-6}$ alkyl-carbonyl group optionally has 1 to 3 substituents at substitutable positions.

As the substituent, those exemplified as the substituents which the $C_{1-10}$ alkyl group and the like exemplified as the "hydrocarbon group" of the "optionally substituted hydrocarbon group" for $R^3$ optionally has, can be mentioned.

In the present specification, "a hydroxyl group substituted by optionally substituted hydrocarbon" is sometimes referred to as "optionally substituted hydrocarbon-oxy group".

The "optionally substituted amino group" for $R^3$ includes an amino group optionally mono- or di-substituted by substituent(s) selected from an optionally substituted hydrocarbon group, an optionally substituted $C_{1-10}$ alkoxy group, an optionally substituted heterocyclic group, an acyl group and the like.

Here, examples of the "optionally substituted hydrocarbon group" and "optionally substituted heterocyclic group" include those similar to the "optionally substituted hydrocarbon group" for $R^3$ and the "optionally substituted heterocyclic group" for $R^3$, respectively.

The $C_{1-10}$ alkoxy group of the aforementioned "optionally substituted $C_{1-10}$ alkoxy group" includes methoxy, ethoxy, propoxy, isopropoxy, butoxy, isobutoxy, sec-butoxy, tert-butoxy, pentyloxy, isopentyloxy, neopentyloxy, 1-ethylpropyloxy, hexyloxy, isohexyloxy, 1,1-dimethylbutyloxy, 2,2-dimethylbutyloxy, 3,3-dimethylbutyloxy, 2-ethylbutyloxy, heptyloxy, octyloxy, nonyloxy, decyloxy and the like.

The $C_{1-10}$ alkoxy group optionally has 1 to 3 substituents at substitutable positions.

As the substituent, those exemplified as the substituents which the $C_{1-10}$ alkyl group and the like exemplified as the "hydrocarbon group" of the "optionally substituted hydrocarbon group" for $R^3$ optionally has, can be mentioned.

As the "acyl group" exemplified as the substituent of the aforementioned "optionally substituted amino group", for example, a group represented by the formula: —$COR^a$, —CO—$OR^a$, —$SO_2R^a$, —$SOR^a$, —CO—$NR^{a'}R^{b'}$, —CS—$NR^{a'}R^{b'}$ or —$SO_2$—$NR^{a'}R^{b'}$ wherein $R^a$ is a hydrogen atom, an optionally substituted hydrocarbon group or an optionally substituted heterocyclic group, and $R^{a'}$ and $R^{b'}$ are the same or different and each is a hydrogen atom, an optionally substituted hydrocarbon group or an optionally substituted heterocyclic group, or $R^{a'}$ and $R^{b'}$ optionally form, together with the adjacent nitrogen atom, an optionally substituted nitrogen-containing heterocycle, and the like can be mentioned.

As the "optionally substituted hydrocarbon group" and "optionally substituted heterocyclic group" for $R^a$, $R^{a'}$ or $R^{b'}$, those similar to the "optionally substituted hydrocarbon group" for $R^3$ and "optionally substituted heterocyclic group" for $R^3$ can be mentioned, respectively.

As the "nitrogen-containing heterocycle" of the "optionally substituted nitrogen-containing heterocycle" formed by $R^{a'}$ and $R^{b'}$ together with the adjacent nitrogen atom, for example, a 5- to 7-membered nitrogen-containing heterocycle containing, as a ring-constituting atom besides carbon atoms, at least one nitrogen atom and optionally further containing one or two heteroatoms selected from an oxygen atom, a sulfur atom and a nitrogen atom can be mentioned.

As preferable examples of the nitrogen-containing heterocycle, pyrrolidine, imidazolidine, pyrazolidine, piperidine, piperazine, morpholine, thiomorpholine, oxopiperazine and the like can be mentioned.

The nitrogen-containing heterocycle optionally has 1 to 3 (preferably 1 or 2) substituents at substitutable positions.

As such substituents, those exemplified as the substituents which the $C_{3-10}$ cycloalkyl group and the like exemplified as the "hydrocarbon group" of the "optionally substituted hydrocarbon group" for $R^3$ optionally has, can be mentioned.

Preferable examples of the "acyl group" include
(1) a formyl group;
(2) a carboxy group;
(3) a carbamoyl group;
(4) a $C_{1-6}$ alkyl-carbonyl group;
(5) a $C_{1-6}$ alkoxy-carbonyl group optionally substituted by 1 to 3 substituents selected from (a) a carboxy group, (b) a carbamoyl group, (c) a thiocarbamoyl group, (d) a $C_{1-6}$ alkoxy-carbonyl group and (e) a $C_{1-6}$ alkyl-carbonyloxy group (e.g., methoxycarbonyl, ethoxycarbonyl, propoxycarbonyl, tertbutoxycarbonyl; carboxymethoxycarbonyl, carboxyethoxycarbonyl, carboxybutoxycarbonyl; carbamoylmethoxycarbonyl; thiocarbamoylmethoxycarbonyl; ethoxycarbonylmethoxycarbonyl, ethoxycarbonylethoxycarbonyl, methoxycarbonylbutoxycarbonyl, ethoxycarbonylbutoxycarbonyl; tertbutylcarbonyloxymethoxycarbonyl);
(6) a $C_{3-10}$ cycloalkyl-carbonyl group (e.g., cyclopentylcarbonyl, cyclohexylcarbonyl);
(7) a $C_{6-14}$ aryl-carbonyl group (e.g., benzoyl, 1-naphthoyl, 2-naphthoyl) optionally substituted by 1 to 3 substituents selected from (a) a halogen atom, (b) a cyano group, (c) a $C_{1-6}$ alkyl group optionally substituted by 1 to 3 halogen atoms,
(d) a $C_{1-6}$ alkoxy group, (e) a carboxy group, (f) a $C_{1-6}$ alkoxy-carbonyl group and (g) a carbamoyl group;
(8) a $C_{6-14}$ aryloxy-carbonyl group (e.g., phenyloxycarbonyl, naphthyloxycarbonyl) optionally substituted by 1 to 3 substituents selected from (a) a carboxy group, (b) a $C_{1-6}$ alkoxy-carbonyl group and (c) a carbamoyl group;
(9) a $C_{7-13}$ aralkyloxy-carbonyl group optionally substituted by 1 to 3 substituents selected from (a) a carboxy group, (b) a carbamoyl group, (c) a thiocarbamoyl group, (d) a $C_{1-6}$ alkoxycarbonyl group, (e) a halogen atom, (f) a cyano group, (g) a nitro group, (h) a $C_{1-6}$ alkoxy group, (i) a $C_{1-6}$ alkylsulfonyl group and (j) a $C_{1-6}$ alkyl group (e.g., benzyloxycarbonyl, phenethyloxycarbonyl; carboxybenzyloxycarbonyl; methoxycarbonylbenzyloxycarbonyl; biphenylylmethoxycarbonyl);
(10) a carbamoyl group mono- or di-substituted by $C_{1-6}$ alkyl group(s) optionally substituted by 1 to 3 substituents selected from a halogen atom and a $C_{1-6}$ alkoxy group (e.g., methylcarbamoyl, ethylcarbamoyl, dimethylcarbamoyl, diethylcarbamoyl, ethylmethylcarbamoyl, propylcarbamoyl, isopropylcarbamoyl, butylcarbamoyl, isobutylcarbamoyl, trifluoroethylcarbamoyl, N-methoxyethyl-N-methylcarbamoyl);
(11) a $C_{1-6}$ alkylsulfonyl group optionally substituted by 1 to 3 substituents selected from (a) a carboxy group, (b) a carbamoyl group and (c) a $C_{1-6}$ alkoxy-carbonyl group (e.g., methylsulfonyl, carboxymethylsulfonyl);
(12) a $C_{3-10}$ cycloalkylsulfonyl group (e.g., cyclopropylsulfonyl);
(13) a $C_{6-14}$ arylsulfonyl group (e.g., benzenesulfonyl) optionally substituted by 1 to 3 substituents selected from
  (a) a $C_{1-6}$ alkyl group optionally substituted by 1 to 3 halogen atoms, and
  (b) a $C_{1-6}$ alkoxy group optionally substituted by 1 to 3 halogen atoms;
(14) an aromatic heterocycle-sulfonyl group (e.g., thienylsulfonyl, imidazolylsulfonyl, pyridylsulfonyl) optionally substituted by 1 to 3 $C_{1-6}$ alkyl groups;
(15) a $C_{1-6}$ alkylsulfinyl group (e.g., methylsulfinyl);
(16) a thiocarbamoyl group;
(17) a $C_{7-13}$ aralkyl-carbonyl group (e.g., benzylcarbonyl, phenethylcarbonyl);
(18) an aromatic heterocycle-carbonyl group (e.g., furylcarbonyl, thienylcarbonyl, thiazolylcarbonyl, pyrazolylcarbonyl, pyridylcarbonyl, pyrazinylcarbonyl, benzofurylcarbonyl, benzothienylcarbonyl, quinoxalinylcarbonyl) optionally substituted by 1 to 3 substituents selected from
  (a) a $C_{1-6}$ alkyl group, (b) a $C_{6-14}$ aryl group, (c) a $C_{7-13}$ aralkyl group, (d) a $C_{1-6}$ alkoxy group,
  (e) a carboxy group, (f) a $C_{1-6}$ alkoxy-carbonyl group and (g) a carbamoyl group;
(19) a sulfamoyl group;
(20) a sulfamoyl group mono- or di-substituted by $C_{1-6}$ alkyl group(s) optionally substituted by 1 to 3 substituents selected from a halogen atom and a $C_{1-6}$ alkoxy group (e.g., methylsulfamoyl, ethylsulfamoyl, dimethylsulfamoyl);
and the like.

The "amino group" of the aforementioned "optionally substituted amino group" is optionally substituted by an amino group optionally mono- or di-substituted by substituent(s) selected from (1) a $C_{1-6}$ alkyl group, (2) a $C_{1-6}$ alkyl-carbonyl group (the $C_{1-6}$ alkyl-carbonyl group is optionally substituted by 1 to 3 substituents selected from a $C_{1-6}$ alkoxy group, a $C_{1-6}$ alkoxy-carbonyl group and the like), (3) a $C_{1-6}$ alkoxy-carbonyl-carbonyl group and the like, and the like.

$R^3$ of the "—$COR^3$" for $R^1$ is preferably an optionally substituted $C_{1-10}$ alkyl group (preferably, $C_{1-6}$ alkyl group), a hydroxy group optionally substituted by a $C_{1-10}$ alkyl group (preferably, $C_{1-6}$ alkyl group), an optionally substituted amino group or an optionally substituted heterocyclic group, more preferably,
(1) a $C_{1-10}$ alkyl group (preferably, a $C_{1-6}$ alkyl group) optionally substituted by 1 to 3 substituents selected from
  (a) a hydroxy group,
  (b) a halogen atom, and
  (c) an aromatic heterocyclyl-carbonylthio group (the aromatic heterocyclyl-carbonylthio group, preferably, is indolylcarbonylthio and the like and optionally substituted by 1 to 3 amino groups (the amino group is optionally mono- or di-substituted by substituent(s) selected from a $C_{1-6}$ alkyl group, an aromatic heterocyclyl-sulfonyl group (preferably, thienylsulfonyl etc.) and the like) and the like;
(2) a hydroxy group;
(3) a $C_{1-10}$ alkoxy group (preferably, $C_{1-6}$ alkoxy group);
(4) an amino group optionally mono- or di-substituted by substituent(s) selected from
  (a) a $C_{1-10}$ alkyl group (preferably, $C_{1-6}$ alkyl group) optionally substituted by 1 to 3 substituents selected from
    (i) a halogen atom,
    (ii) a hydroxy group,
    (iii) a $C_{1-6}$ alkylthio group (the $C_{1-6}$ alkylthio group is optionally substituted by 1 to 3 $C_{6-14}$ aryl groups and the like),
    (iv) a carbamoyl group (the carbamoyl group is optionally mono- or di-substituted with $C_{1-6}$ alkyl group(s) and the like,
    (v) a non-aromatic heterocyclic group (preferably, piperidinyl) optionally substituted by a $C_{7-20}$ aralkylthio group (preferably, benzylthio), and the like,
  (b) a $C_{1-10}$ alkoxy group (preferably, $C_{1-6}$ alkoxy group),
  (c) a $C_{6-14}$ aryl group,
  (d) a $C_{7-13}$ aralkyl group,
  (e) an aromatic heterocyclic group (preferably, thiazolyl, oxazolyl etc.),
  (f) an amino group optionally mono- or di-substituted by substituent(s) selected from
    (i) a $C_{1-6}$ alkyl-carbonyl group (the $C_{1-6}$ alkyl-carbonyl group optionally substituted by 1 to 3 substituents selected from a $C_{1-6}$ alkoxy group, a $C_{1-6}$ alkoxy-carbonyl group, etc.),
    (ii) a $C_{1-6}$ alkoxy-carbonyl-carbonyl group, and the like; or
(5) a heterocyclic group (preferably, aromatic heterocyclic group such as pyridyl, oxadiazolyl, thiadiazolyl, thiazolyl, oxazolyl, triazolyl, tetrazolyl, benzothiazolyl and the like; non-aromatic heterocyclic group such as pyrrolidinyl, piperidinyl, oxazolinyl, thiazolinyl and the like) optionally substituted by 1 to 3 substituents selected from
  (a) a $C_{1-6}$ alkyl group optionally substituted by 1 to 3 substituents selected from
    (i) a $C_{1-6}$ alkoxy group (the $C_{1-6}$ alkoxy group is optionally substituted by 1 to 3 substituents selected from a carboxy group, a $C_{1-6}$ alkoxy-carbonyl group and the like),
    (ii) a hydroxy group,
    (iii) a $C_{1-6}$ alkoxy-carbonyl group,
    (iv) a carboxy group,
    (v) a carbamoyl group (the carbamoyl group is optionally mono- or di-substituted by substituent(s) selected from a $C_{1-6}$ alkylsulfonyl group, an amino group and the like),
    (vi) a $C_{1-6}$ alkylsulfonyl group,
    (vii) an aromatic heterocyclic group (preferably, tetrazolyl etc.),
    (viii) a non-aromatic heterocyclic group (the non-aromatic heterocyclic group, preferably, is morpholinyl, dihydrooxadiazolyl and the like and optionally substituted by 1 to 3 oxo groups and the like),
    (ix) a non-aromatic heterocyclyl-carbonyl group (preferably, morpholinylcarbonyl etc.),
    (x) a cyano group,
    (xi) a $C_{6-14}$ aryloxy group (the $C_{6-14}$ aryloxy group is optionally substituted by 1 to 3 substituents selected from a carboxy group, a $C_{1-6}$ alkoxy-carbonyl group and the like),
    (xii) a $C_{1-6}$ alkylthio group (the $C_{1-6}$ alkylthio group is optionally substituted by 1 to 3 substituents selected from a hydroxy group, a carbamoyl group and the like) and the like,
  (b) an amino group optionally mono- or di-substituted by substituent(s) selected from
    (i) a $C_{1-6}$ alkyl group,
    (ii) a $C_{1-6}$ alkoxy-carbonyl group and the like,
  (c) a $C_{1-6}$ alkoxy-carbonyl group,
  (d) a carboxy group,
  (e) a formyl group, and the like; more preferably,
(1) a $C_{1-10}$ alkyl group (preferably, $C_{1-6}$ alkyl group), (2) a hydroxy group,
(3) a $C_{1-10}$ alkoxy group (preferably, $C_{1-6}$ alkoxy group), or
(4) an amino group optionally mono- or di-substituted by substituent(s) selected from
  (a) a $C_{1-10}$ alkyl group (preferably, $C_{1-6}$ alkyl group) optionally substituted by a non-aromatic heterocyclic group (preferably, piperidinyl) optionally substituted by a $C_{7-20}$ aralkylthio group (preferably, benzylthio);
  (b) a $C_{1-10}$ alkoxy group (preferably, $C_{1-6}$ alkoxy group); and
  (c) an amino group optionally mono-substituted by a $C_{1-6}$ alkoxy-carbonyl-carbonyl group.

The "5- to 7-membered heterocyclic group" of the "optionally substituted 5- to 7-membered heterocyclic group" for $R^1$ includes a 5- to 7-membered aromatic heterocyclic group and a 5- to 7-membered non-aromatic heterocyclic group.

The "5- to 7-membered aromatic heterocyclic group" includes a 5- to 7-membered ring from the groups exemplified as monocyclic aromatic heterocyclic group of the "optionally substituted heterocyclic group" for $R^3$.

The "5- to 7-membered aromatic heterocyclic group" optionally has 1 to 3 substituents at substitutable position(s). As such substituent, those exemplified as the substituents which the $C_{3-10}$ cycloalkyl group and the like exemplified as the "hydrocarbon group" of the "optionally substituted hydrocarbon group" for $R^3$ optionally have, can be mentioned.

The "5- to 7-membered non-aromatic heterocyclic group" includes a 5- to 7-membered ring from the groups exemplified as monocyclic non-aromatic heterocyclic group of the "optionally substituted heterocyclic group" for $R^3$.

The "5- to 7-membered non-aromatic heterocyclic group" optionally has 1 to 3 substituents at substitutable position(s). As such substituents, those exemplified as the substituents which the $C_{3-10}$ cycloalkyl group and the like exemplified as the "hydrocarbon group" of the "optionally substituted hydrocarbon group" for $R^3$ optionally have, can be mentioned.

Alternatively, the "5- to 7-membered non-aromatic heterocyclic group" may form a Spiro ring with the "optionally substituted ring" formed by two substituents bonded to each other, which are bonded to the same carbon atom on the ring.

The ring of the "optionally substituted ring" includes $C_{3-10}$ cycloalkane, $C_{3-10}$ cycloalkene, $C_{4-10}$ cycloalkadiene and 5- or 6-membered non-aromatic heterocycle.

As $C_{3-10}$ cycloalkane, $C_{3-10}$ cycloalkene and $C_{4-10}$ cycloalkadiene, rings corresponding to the $C_{3-10}$ cycloalkyl group, $C_{3-10}$ cycloalkenyl group and $C_{4-10}$ cycloalkadienyl group exemplified as the "hydrocarbon group" of the "optionally substituted hydrocarbon group" for $R^3$ can be mentioned. As the 5- or 6-membered non-aromatic heterocycle, a ring corresponding to the 5- or 6-membered ring group from the groups exemplified as the monocyclic non-aromatic heterocyclic group of the "optionally substituted heterocyclic group" for $R^3$ can be mentioned. Of these, piperidine and the like are preferable.

The "ring" of the "optionally substituted ring" optionally has 1 to 3 substituents at substitutable position(s). As such substituents, those exemplified as the substituents which the $C_{3-10}$ cycloalkyl group and the like exemplified as the "hydrocarbon group" of the "optionally substituted hydrocarbon group" for $R^3$ optionally have, can be mentioned.

The "optionally substituted 5- to 7-membered heterocyclic group" for $R^1$ is preferably an optionally substituted 5- to 7-membered (preferably, 5- or 6-membered) aromatic heterocyclic group (preferably, thiadiazolyl, more preferably, thiadiazol-2-yl) or an optionally substituted 5- to 7-membered (preferably, 5- or 6-membered) non-aromatic heterocyclic group (preferably, thiazolinyl, more preferably, thiazolin-2-yl), more preferably,
(1) a 5- to 7-membered (preferably 5- or 6-membered) aromatic heterocyclic group (preferably, thiadiazolyl, more preferably, thiadiazol-2-yl) optionally substituted by 1 to 3 substituents selected from
  (a) a $C_{1-6}$ alkoxy-carbonyl group, and
  (b) a $C_{1-6}$ alkyl group optionally substituted by 1 to 3 hydroxy groups; or
(2) a 5- to 7-membered (preferably 5- or 6-membered) non-aromatic heterocyclic group (preferably, thiazolinyl, more preferably, thiazolin-2-yl), which is
  (a) optionally substituted by a $C_{1-6}$ alkyl group optionally substituted by 1 to 3 $C_{1-6}$ alkoxy group, or which
  (b) optionally forms a spiro ring (preferably, 1-thia-3,8-diazaspiro[4.5]deca-2-en-2-yl) with a 5- or 6-membered non-aromatic heterocycle (preferably, piperidine) optionally substituted by a $C_{1-6}$ alkyl-carbonyl group.

$R^2$ is a hydrogen atom or a halogen atom.
$R^2$ is preferably a hydrogen atom.
$R^4$, $R^5$ and $R^6$ are each independently a hydrogen atom or a substituent. However, $R^4$, $R^5$ and $R^6$ are absent when an atom on ring A they are bonded to cannot have a substituent. For example, when ring A is the following

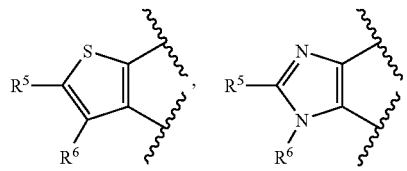

wherein each symbol is as defined above, $R^4$ is absent.

The substituent for $R^4$, $R^5$ or $R^6$ includes "optionally substituted hydrocarbon group", "optionally substituted heterocyclic group", "optionally substituted hydroxy group", "optionally substituted mercapto group", "optionally substituted amino group", "cyano group", "nitro group", "acyl group", "halogen atom" and the like.

The "optionally substituted hydrocarbon group", "optionally substituted heterocyclic group", "optionally substituted hydroxy group" and "optionally substituted amino group" for $R^4$, $R^5$ or $R^6$ include those similar to the "optionally substituted hydrocarbon group", "optionally substituted heterocyclic group", "optionally substituted hydroxy group" and "optionally substituted amino group" for $R^3$, respectively.

The "acyl group" for $R^4$, $R^5$ or $R^6$ includes those similar to the "acyl group" as the substituent of the "optionally substituted amino group" for $R^3$.

The "optionally substituted mercapto group" for $R^4$, $R^5$ or $R^6$ includes a mercapto group optionally substituted by substituent(s) selected from an optionally substituted hydrocarbon group, an optionally substituted $C_{1-6}$ alkyl-carbonyl group, a heterocyclic group and the like.

Here, the "optionally substituted hydrocarbon group" and "optionally substituted heterocyclic group" include those similar to the "optionally substituted hydrocarbon group" for $R^3$ and the "optionally substituted heterocyclic group" for $R^3$, respectively.

The aforementioned $C_{1-6}$ alkyl-carbonyl group optionally has 1 to 3 substituents at substitutable position(s).

As such substituents, those exemplified as the substituents which the $C_{1-10}$ alkyl group and the like exemplified as the "hydrocarbon group" of the "optionally substituted hydrocarbon group" for $R^3$ optionally have can be mentioned.

$R^4$ is preferably an optionally substituted hydrocarbon group, more preferably a $C_{1-6}$ alkyl group or a $C_{7-13}$ aralkyl group (preferably, benzyl group).

However, $R^4$ is absent when an atom on ring A it is bonded to cannot have a substituent.

$R^5$ is preferably a hydrogen atom or an optionally substituted hydrocarbon group, more preferably, a hydrogen atom or a $C_{1-6}$ alkyl group. However, $R^5$ is absent when an atom on ring A it is bonded to cannot have a substituent.

$R^6$ is preferably an optionally substituted hydrocarbon group, an optionally substituted hydroxy group or an optionally substituted amino group, more preferably, an optionally substituted $C_{1-6}$ alkyl group, an optionally substituted hydrocarbon-oxy group or an optionally substituted amino group, still more preferably, an optionally substituted amino group. Preferable specific examples of $R^6$ include an amino group optionally mono- or di-substituted by substituent(s) selected from
  (a) a $C_{1-10}$ alkyl group,
  (b) a $C_{7-13}$ aralkyloxy-carbonyl group (preferably, benzyloxycarbonyl), and
  (c) an aromatic heterocyclic sulfonyl group (preferably, thienylsulfonyl).

$R^6$ is absent when an atom on ring A it is bonded to cannot have a substituent.

Ring A is a 5-membered ring.

The "5-membered ring" for ring A includes a 5-membered aromatic ring, a 5-membered non-aromatic ring and the like.

The 5-membered aromatic ring includes 5-membered aromatic heterocycle and the like.

The 5-membered aromatic heterocycle includes rings constituting the 5-membered aromatic heterocyclic group exemplified as the "heterocyclic group" of the "optionally substituted heterocyclic group" for $R^3$, specifically, furan, thiophene, pyrrole, imidazole, pyrazole, thiazole, isothiazole, oxazole, isoxazole, 1,2,3-oxadiazole, furazan, 1,2,3-thiadiazole, 1,2,3-triazole and the like.

The 5-membered non-aromatic ring includes 5-membered non-aromatic cyclic hydrocarbon, 5-membered non-aromatic heterocycle and the like.

The 5-membered non-aromatic cyclic hydrocarbon includes cyclopentene, cyclopentadiene and the like.

The 5-membered non-aromatic heterocycle includes a ring constituting a 5-membered non-aromatic heterocyclic group exemplified as the "heterocyclic group" in the "optionally substituted heterocyclic group" for $R^3$, for example, 2-pyrroline, 3-pyrroline, 1,2-dihydrofuran, 2,5-dihydrofuran, 1,2-dihydrothiophene, 2,5-dihydrothiophene, imidazoline, pyrazoline, oxazoline, isoxazoline, thiazoline, isothiazoline and the like can be mentioned.

Ring A is preferably 5-membered aromatic heterocycle, more preferably, thiophene ring, pyrrole ring, imidazole ring.

As compound (I), the following compounds are preferable.

[Compound (A)]

A compound wherein
ring A is 5-membered aromatic heterocycle (preferably, thiophene ring, pyrrole ring, imidazole ring),
$R^1$ is
(1) a 5- to 7-membered (preferably 5- or 6-membered) aromatic heterocyclic group (preferably, thiadiazolyl, more preferably, thiadiazol-2-yl) optionally substituted by 1 to 3 substituents selected from
  (a) a $C_{1-6}$ alkoxy-carbonyl group, and
  (b) a $C_{1-6}$ alkyl group optionally substituted by 1 to 3 hydroxy groups; or (2) a 5- to 7-membered (preferably 5- or 6-membered) non-aromatic heterocyclic group (preferably, thiazolinyl, more preferably, thiadiazolin-2-yl), which is
  (a) optionally substituted by a $C_{1-6}$ alkyl group optionally substituted by 1 to 3 $C_{1-6}$ alkoxy groups, or which
  (b) optionally forms a spiro ring (preferably, 1-thia-3,8-diazaspiro[4.5]deca-2-en-2-yl) with a 5- or 6-membered non-aromatic heterocycle (preferably, piperidine) optionally substituted by a $C_{1-6}$ alkyl-carbonyl group; or
—$COR^3$ wherein $R^3$ is preferably
(1) a $C_{1-10}$ alkyl group (preferably, $C_{1-6}$ alkyl group),
(2) a hydroxy group,
(3) a $C_{1-10}$ alkoxy group (preferably, $C_{1-6}$ alkoxy group), or
(4) an amino group optionally mono- or di-substituted by substituent(s) selected from
  (a) a $C_{1-10}$ alkyl group (preferably, $C_{1-6}$ alkyl group) optionally substituted by a non-aromatic heterocyclic group (preferably, piperidinyl) optionally substituted by a $C_{7-20}$ aralkylthio group (preferably, benzylthio);
  (b) a $C_{1-10}$ alkoxy group (preferably, $C_{1-6}$ alkoxy group); and
  (c) an amino group optionally mono-substituted by a $C_{1-6}$ alkoxy-carbonyl-carbonyl group, $R^2$ is a hydrogen atom,
$R^4$ is a $C_{1-6}$ alkyl group or a $C_{7-13}$ aralkyl group (preferably, benzyl),
$R^5$ is a hydrogen atom or a $C_{1-6}$ alkyl group,
$R^6$ is an amino group optionally mono- or di-substituted by substituent(s) selected from
  (a) a $C_{1-10}$ alkyl group,
  (b) a $C_{7-13}$ aralkyloxy-carbonyl group (preferably, benzyloxycarbonyl), and
  (c) an aromatic heterocycle-sulfonyl group (preferably, thienylsulfonyl)
(provided that $R^4$, $R^5$ and $R^6$ are absent when an atom on ring A they are bonded to cannot have a substituent).

[Compound (B)]

ethyl 3-benzyl-2-methyl-3,4-dihydropyrrolo[2,3-d]imidazol-5-carboxylate (Example 1);

N-[5-(4,5-dihydro-1,3-thiazol-2-yl)-2-methyl-4H-thieno[3,2-b]pyrrol-3-yl]-N-methylthiophen-2-sulfonamide (Example 5);

N-[5-(8-acetyl-1-thia-3,8-diazaspiro[4.5]deca-2-en-2-yl)-2-methyl-4H-thieno[3,2-b]pyrrol-3-yl]-N-methylthiophen-2-sulfonamide (Example 8);

N-[5-(4,5-dihydro-1,3-thiazol-2-yl)-1-ethyl-1,4-dihydropyrrolo[3,2-b]pyrrol-3-yl]-N-methylthiophen-2-sulfonamide (Example 17);

ethyl 4-benzyl-6-[methyl(2-thienylsulfonyl)amino]-1,4-dihydropyrrolo[3,2-b]pyrrol-2-carboxylate (Example 18); or a salt thereof.

Of compounds (I), a compound wherein
A) when $R^1$ is —$COR^3$ ($R^3$ is as defined above), then $R^6$ is an optionally substituted amino group, an optionally substituted $C_{1-6}$ alkyl group or an optionally substituted hydrocarbon-oxy group, or
B) when $R^1$ is —$COR^3$ ($R^3$ is as defined above) and ring A is a thiophene ring or a furan ring, then $R^6$ is an optionally substituted amino group or an optionally substituted hydrocarbon-oxy group
[excluding the following compounds:
methyl 3-{[2'-(methoxycarbonyl)biphenyl-4-yl]methyl}-2-propyl-3,4-dihydropyrrolo[2,3-d]imidazol-5-carboxylate,
methyl 2-butyl-3-{[2'-(methoxycarbonyl)biphenyl-4-yl]methyl}-3,4-dihydropyrrolo[2,3-d]imidazol-5-carboxylate,
ethyl 3-[4-(ethoxycarbonyl)benzyl]-2-propyl-3,4-dihydropyrrolo[2,3-d]imidazol-5-carboxylate, ethyl 2-butyl-3-[4-(ethoxycarbonyl)benzyl]-3,4-dihydropyrrolo[2,3-d]imidazol-5-carboxylate,
ethyl 3-methyl-3,4-dihydropyrrolo[2,3-d]imidazol-5-carboxylate, and
ethyl 3,6-dimethyl-1,4,5,6-tetrahydrocyclopenta[b]pyrrol-2-carboxylate]
is novel.

Furthermore, of compounds (I), a compound wherein $R^6$ is an optionally substituted amino group is also novel.

When compound (I) is a salt, as such salts, for example, a salt with inorganic base, a salt with organic base, a salt with inorganic acid, a salt with organic acid, a salt with basic or acidic amino acid and the like can be mentioned.

Preferable examples of salts with inorganic base include alkali metal salts such as sodium salt, potassium salt and the like; alkaline earth metal salts such as calcium salt, magnesium salt and the like; and aluminum salts; ammonium salts and the like.

As preferable examples of the salts with organic bases, salts with trimethylamine, triethylamine, pyridine, picoline, ethanolamine, diethanolamine, triethanolamine, dicyclohexylamine, N,N-dibenzylethylenediamine and the like can be mentioned.

As preferable examples of the salts with inorganic acids, salts with hydrochloric acid, hydrobromic acid, nitric acid, sulfuric acid, phosphoric acid and the like can be mentioned.

As preferable examples of the salts with organic acids, salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like can be mentioned.

As preferable examples of the salts with basic amino acid, salts with arginine, lysine, ornithine and the like can be mentioned.

As preferable examples of the salts with acidic amino acids, salts with aspartic acid, glutamic acid and the like can be mentioned.

A prodrug of compound (I) means a compound which is converted to the present invention with a reaction due to an enzyme, an gastric acid, etc. under the physiological condition in the living body, that is, a compound which is converted to compound (I) with oxidation, reduction, hydrolysis, etc. according to an enzyme; a compound which is converted to compound (I) by hydrolysis etc. due to gastric acid, etc. A prodrug of compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation); a compound obtained by subjecting a hydroxy group in compound (I) to an acylation, alkylation, phosphorylation or boration (e.g., a compound obtained by subjecting an hydroxy group in compound (I) to an acetylation, palmitoylation, propanoylation, pivaloylation, succinylation, fumarylation, alanylation or dimethylaminomethylcarbonylation); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like. Any of these compounds can be produced from compound (I) by a method known per se.

A prodrug of compound (I) may also be one which is converted into the present invention under a physiological condition, such as those described in IYAKUHIN NO KAIHATSU (Development of Pharmaceuticals), Vol. 7, Design of Molecules, p. 163-198, published by HIROKAWA SHOTEN (1990).

Compound (I) may be labeled with an isotope (e.g., $^3H$, $^{14}C$, $^{35}S$, $^{125}I$, etc.) and the like.

Furthermore, compound (I) may be a non-hydrate or hydrate.

Furthermore, a deuterium converted form wherein $^1H$ is converted to $^2H(D)$ is also encompassed in compound (I).

Compound (I) or a prodrug thereof (hereinafter sometimes to be abbreviated as the compound of the present invention) shows low toxicity and can be used as an agent for the prophylaxis or treatment of various diseases to be mentioned later for mammals (e.g., humans, mice, rats, rabbits, dogs, cats, bovines, horses, pigs, monkeys) as they are or by admixing with a pharmacologically acceptable carrier and the like to give a pharmaceutical composition.

Here, various organic or inorganic carriers conventionally used as materials for pharmaceutical preparations are used as a pharmacologically acceptable carrier, which are added as excipient, lubricant, binder and disintegrant for solid preparations; or solvent, solubilizing agent, suspending agent, isotonicity agent, buffer and soothing agent for liquid preparations, and the like. Where necessary, an additive for pharmaceutical preparations such as preservative, antioxidant, colorant, sweetening agent and the like can be used.

Preferable examples of the excipient include lactose, sucrose, D-mannitol, D-sorbitol, starch, a-starch, dextrin, crystalline cellulose, low-substituted hydroxypropylcellulose, sodium carboxymethylcellulose, gum acacia, pullulan, light anhydrous silicic acid, synthetic aluminum silicate, magnesium aluminate metasilicate and the like.

Preferred examples of the lubricant include magnesium stearate, calcium stearate, talc, colloidal silica and the like.

Preferable examples of the binder include α-starch, saccharose, gelatin, gum acacia, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose, polyvinylpyrrolidone and the like.

Preferable examples of the disintegrant include lactose, sucrose, starch, carboxymethylcellulose, calcium carboxymethylcellulose, sodium croscarmellose, sodium carboxymethyl starch, light anhydrous silicic acid, low-substituted hydroxypropylcellulose and the like.

Preferable examples of the solvent include water for injection, physiological brine, Ringer's solution, alcohol, propylene glycol, polyethylene glycol, sesame oil, corn oil, olive oil, cottonseed oil and the like.

Preferred examples of the solubilizing agents include polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate and the like.

Preferred examples of the suspending agent include surfactants such as stearyltriethanolamine, sodium lauryl sulfate, lauryl aminopropionate, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates, polyoxyethylene hydrogenated castor oil and the like.

Preferred examples of the isotonicity agent include sodium chloride, glycerol, D-mannitol, D-sorbitol, glucose and the like.

Preferred examples of the buffer include buffers such as phosphate, acetate, carbonate, citrate and the like.

Preferred examples of the soothing agent include benzyl alcohol and the like.

Preferred examples of the preservative include paraoxybenzoates, chlorobutanol, benzyl alcohol, phenethyl alcohol, dehydroacetate, sorbic acid and the like.

Preferred examples of the antioxidant include sulfite, ascorbate and the like.

Preferable examples of the colorant include aqueous edible tar pigments (e.g., foodcolors such as Food Color Red Nos. 2 and 3, Food Color Yellow Nos. 4 and 5, Food Color Blue Nos. 1 and 2 and the like), water insoluble lake pigments (e.g., aluminum salt of the aforementioned aqueous edible tar pigment), natural pigments (e.g., beta carotene, chlorophil, red iron oxide) and the like.

Preferable examples of the sweetening agent include saccharin sodium, dipotassium glycyrrhizinate, aspartame, stevia and the like.

Examples of the dosage form of the aforementioned pharmaceutical composition include oral preparation such as tablet (containing sugar-coated tablet, film-coated tablet, sublingual tablet, orally disintegrating tablet), capsule (containing soft capsule, microcapsule), granule, powder, troche, syrup, emulsion, suspension, films (e.g., orally disintegrable films) and the like; and parenteral agent such as injection (e.g., subcutaneous injection, intravenous injection, intramuscular injection, intraperitoneal injection, drip infusion), external preparation (e.g., dermal preparation, ointment), suppository (e.g., rectal suppository, vaginal suppository), pellet, nasal preparations, pulmonary preparation (inhalant), eye drop, etc. and the like. These may be administered safely via an oral or parenteral route (e.g., topical, rectal, intravenous administration).

In addition, these agents may be controlled-release preparations such as rapid-release preparations and sustained-release preparations (e.g., sustained-release microcapsules).

The pharmaceutical composition can be produced according to a method conventionally used in the field of pharmaceutical preparation, such as the method described in Japan Pharmacopoeia and the like. Specific production methods of the preparation are described in detail in the following.

While the content of the compound of the present invention in the pharmaceutical composition varies depending on the dosage form, dose of the compound of the present invention and the like, it is, for example, about 0.1 to 100 wt %.

The compound of the present invention has a superior GK activating action, and can be used as an agent for the prophylaxis or treatment of various diseases for mammals (e.g., human, bovine, horse, dog, cat, monkey, mouse, rat, specifically human). In addition, as the compound of the present invention has a selective GK activating action, it shows low toxicity (e.g., acute toxicity, chronic toxicity, cardiotoxicity, carcinogenic, genetic toxicity), which causes fewer side effects.

The compound of the present invention can be used as an agent for the prophylaxis or treatment of diabetes (e.g., type 1 diabetes, type 2 diabetes, gestational diabetes, obese diabetes); an agent for the prophylaxis or treatment of hyperlipidemia (e.g., hypertriglyceridemia, hypercholesterolemia, hypo-HDL-emia, postprandial hyperlipidemia); an agent for the prophylaxis or treatment of arteriosclerosis; an agent for the prophylaxis or treatment of impaired glucose tolerance (IGT); and an agent for preventing progression of impaired glucose tolerance into diabetes.

For diagnostic criteria of diabetes, Japan Diabetes Society reported new diagnostic criteria in 1999.

According to this report, diabetes is a condition showing any of a fasting blood glucose level (glucose concentration of venous plasma) of not less than 126 mg/dl, a 75 g oral glucose tolerance test (75 g OGTT) 2 h level (glucose concentration of venous plasma) of not less than 200 mg/dl, and a non-fasting blood glucose level (glucose concentration of venous plasma) of not less than 200 mg/dl. A condition not falling under the above-mentioned diabetes and different from "a condition showing a fasting blood glucose level (glucose concentration of venous plasma) of less than 110 mg/dl or a 75 g oral glucose tolerance test (75 g OGTT) 2 h level (glucose concentration of venous plasma) of less than 140 mg/dl" (normal type) is called a "borderline type".

In addition, ADA (American Diabetes Association) and WHO reported new diagnostic criteria of diabetes.

According to these reports, diabetes is a condition showing a fasting blood glucose level (glucose concentration of venous plasma) of not less than 126 mg/dl or a 75 g oral glucose tolerance test 2 h level (glucose concentration of venous plasma) of not less than 200 mg/dl.

According to the reports of ADA and WHO, impaired glucose tolerance is a condition showing a 75 g oral glucose tolerance test 2 h level (glucose concentration of venous plasma) of not less than 140 mg/dl and less than 200 mg/dl. According to the report of ADA, a condition showing a fasting blood glucose level (glucose concentration of venous plasma) of not less than 100 mg/dl and less than 126 mg/dl is called IFG (Impaired Fasting Glucose). According to WHO, among the IFG (Impaired Fasting Glucose), a condition showing a fasting blood glucose level (glucose concentration of venous plasma) of not less than 110 mg/dl and less than 126 mg/dl is called IFG (Impaired Fasting Glycemia).

The compound of the present invention can also be used as an agent for the prophylaxis or treatment of diabetes, borderline type, impaired glucose tolerance, IFG (Impaired Fasting Glucose) and IFG (Impaired Fasting Glycemia), as determined according to the above-mentioned new diagnostic criteria. Moreover, the compound of the present invention can prevent progress of borderline type, impaired glucose tolerance, IFG (Impaired Fasting Glucose) or IFG (Impaired Fasting Glycemia) into diabetes.

The compound of the present invention can also be used as an agent for the prophylaxis or treatment of, for example, diabetic complications [e.g., neuropathy, nephropathy, retinopathy, cataract, macroangiopathy, osteopenia, hyperosmolar diabetic coma, infectious disease (e.g., respiratory infection, urinary tract infection, gastrointestinal infection, dermal soft tissue infections, inferior limb infection), diabetic foot (e.g., gangrene, ulcer), xerostomia, hypacusis, cerebrovascular disorder, peripheral blood circulation disorder, diabetic diarrhea], obesity, osteoporosis, cachexia (e.g., cancerous cachexia, tuberculous cachexia, diabetic cachexia, blood disease cachexia, endocrine disease cachexia, infectious disease cachexia or cachexia due to acquired immunodeficiency syndrome), fatty liver, hypertension, polycystic ovary syndrome, kidney disease (e.g., diabetic nephropathy, glomerular nephritis, glomerulosclerosis, nephrotic syndrome, hypertensive nephrosclerosis, end stage kidney disease, pyelonephritis, hydronephrosis), muscular dystrophy, myocardial infarction, angina pectoris, cerebrovascular accident (e.g., cerebral infarction, cerebral apoplexy), abnormal sugar metabolism, abnormal lipid metabolism, insulin resistance syndrome, Syndrome X, metabolic syndrome (according to the aforementioned report of WHO, state concurrently associated with at least one of type 2 diabetes, impaired glucose tolerance and insulin resistance, and at least two from obesity, abnormal lipid metabolism, hypertension and trace albumin urine), Cushing's syndrome, hyperinsulinemia, hyperinsulinemia-induced sensory disorder, tumor (e.g., leukemia, breast cancer, prostate cancer, skin cancer), irritable bowel syndrome, acute or chronic diarrhea, inflammatory diseases (e.g., chronic rheumatoid arthritis, spondylitis deformans, osteoarthritis, lumbago, gout, postoperative or traumatic inflammation, swelling, neuralgia, pharyngolaryngitis, cystitis, hepatitis (inclusive of non-alcoholic steatohepatitis), pneumonia, pancreatitis, inflammatory bowel disease, ulcerative colitis, stomach mucous membrane injury (including stomach mucous membrane injury caused by aspirin)), visceral fat syndrome, Alzheimer's disease, cerebrovascular dementia, depression and the like.

The compound of the present invention can also be used for improvement of insulin resistance, promotion or increase of insulin secretion, decrease of visceral fat, suppression of accumulation of visceral fat, improvement of sugar metabolism, improvement of lipid metabolism (including suppression of oxidative LDL production, improvement of lipoprotein metabolism, and lowering of blood remnant), improvement of coronary metabolism, prophylaxis or treatment of cardiovascular complication, prophylaxis or treatment of heart failure complication, prophylaxis or treatment of anovulation, prophylaxis or treatment of hirsutism, prophylaxis or treatment of hyperandrogenism, improvement of pancreatic (β cell) function, regeneration of pancreas (β cell), promotion of regeneration of pancreas (β cell) and the like.

The compound of the present invention can also be used for the secondary prevention and suppression of progression of various diseases mentioned above (e.g., cardiovascular event such as myocardial infarction etc.).

The compound of the present invention is particularly useful as an agent for the prophylaxis or treatment of type 2 diabetes, obese diabetes and the like.

While the dose of the compound of the present invention varies depending on the administration subject, administration route, target disease, condition and the like, the compound of the present invention is generally given in a single dose of about 0.01-100 mg/kg body weight, preferably 0.05-30 mg/kg body weight, more preferably 0.1-10 mg/kg body weight, in the case of, for example, oral administration to adult diabetic patients. This dose is desirably given 1 to 3 times a day.

The compound of the present invention can be used in combination with drugs such as a therapeutic agent for diabetes, a therapeutic agent for diabetic complications, a therapeutic agent for hyperlipidemia, an antihypertensive agent, an antiobestic agent, a diuretic, a chemotherapeutic agent, an immunotherapeutic agent, an antithrombotic agent, a therapeutic agent for osteoporosis, a antidementia agent, an erectile dysfunction improver, a therapeutic agent for pollakiuria or urinary incontinence, a therapeutic agent for dysuria and the like (hereinafter to be referred to as a combination drug). In this case, the timing of administration of the compound of the present invention and a combination drug is not limited. These may be simultaneously administered to an administration subject or administered in a staggered manner. Moreover, the compound of the present invention and a combination drug may be administered as two kinds of preparations each containing an active ingredient, or may be administered as a single preparation containing both active ingredients.

The dose of the combination drug can be selected as appropriate based on the dose clinically employed. The proportion of the compound of the present invention and the combination drug can be appropriately selected depending on the administration subject, administration route, target disease, condition, combination and the like. When, for example, the administration subject is human, the combination drug is used in an amount of 0.01-100 parts by weight per 1 part by weight of the compound of the present invention.

Examples of the therapeutic agents for diabetes include insulin preparations (e.g., animal insulin preparations extracted from pancreas of bovine and swine; human insulin preparations genetically synthesized using *Escherichia coli*, yeast; zinc insulin; protamine zinc insulin; fragment or derivative of insulin (e.g., INS-1 etc.), oral insulin preparation and the like), insulin sensitizers (e.g., pioglitazone or a salt thereof (preferably hydrochloride), rosiglitazone or a salt thereof (preferably maleate), Tesaglitazar, Ragaglitazar, Muraglitazar, Edaglitazone, Metaglidasen, Naveglitazar, AMG-131, THR-0921), α-glucosidase inhibitor (e.g., voglibose, acarbose, miglitol, emiglitate), biguanide (e.g., metformin, buformin or a salt thereof (e.g., hydrochloride, fumarate, succinate)), insulin secretagogue [sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or a calcium salt hydrate thereof], dipeptidyl peptidase IV inhibitor (e.g., Vildagliptin, Sitagliptin, Saxagliptin, T-6666, TS-021), β3 agonist (e.g., AJ-9677), GPR40 agonist, GLP-1 receptor agonist [e.g., GLP-1, GLP-1MR agent, NN-2211, AC-2993 (exendin-4), BIM-51077, Aib(8,35)hGLP-1(7,37)NH$_2$, CJC-1131], amylin agonist (e.g., pramlintide), phosphotyrosine phosphatase inhibitors (e.g., sodium vanadate), gluconeogenesis inhibitor (e.g., glycogen phosphorylase inhibitor, glucose-6-phosphatase inhibitors, glucagon antagonists), SGLT (sodium-glucose cotransporter) inhibitor (e.g., T-1095), 11β-hydroxysteroid dehydrogenase inhibitor (e.g., BVT-3498), adiponectin or an agonist thereof, IKK inhibitor (e.g., AS-2868), leptin resistance improving drugs, somatostatin receptor agonists, glucokinase activators (e.g., Ro-28-1675), GIP (Glucose-dependent insulinotropic peptide) and the like.

Examples of the therapeutic agents for diabetic complications include aldose reductase inhibitors (e.g., Tolrestat, Epalrestat, Zenarestat, Zopolrestat, Minalrestat, Fidarestat, CT-112, ranirestst (AS-3201)), neurotrophic factors and increasing drugs thereof (e.g., NGF, NT-3, BDNF, neurotrophin production-secretion promoters described in WO01/14372 (e.g., 4-(4-chlorophenyl)-2-(2-methyl-1-imidazolyl)-5-[3-(2-methylphenoxy)propyl]oxazole)), stimulators (e.g., Y-128), PKC inhibitors (e.g., ruboxistaurin mesylate), AGE inhibitors (e.g., ALT-946, pimagedine, N-phenacylthiazolium bromide (ALT-766), ALT-711, EXO-226, Pyridorin, Pyridoxamine), active oxygen scavengers (e.g., thioctic acid), cerebral vasodilators (e.g., tiapuride, mexiletine), somatostatin receptor agonists (BIM23190), apoptosis signal regulating kinase-1 (ASK-1) inhibitors and the like.

Examples of the therapeutic agents for hyperlipidemia include HMG-CoA reductase inhibitors (e.g., pravastatin, simvastatin, lovastatin, atorvastatin, fluvastatin, pitavastatin, rosuvastatin and salts thereof (e.g., sodium is salt, calcium salt)), squalene synthase inhibitors (e.g., compounds described in WO97/10224, such as N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid), fibrate compounds (e.g., bezafibrate, clofibrate, simfibrate, clinofibrate), ACAT inhibitors (e.g., Avasimibe, Eflucimibe), anion exchange resins (e.g., colestyramine), probucol, nicotinic acid drugs (e.g., nicomol, niceritrol), ethyl icosapentate, phytosterols (e.g., soysterol, γ-oryzanol) and the like.

Examples of the antihypertensive agents include angiotensin converting enzyme inhibitors (e.g., captopril, enalapril, delapril), angiotensin II antagonists (e.g., candesartan cilexetil, losartan, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid), calcium antagonists (e.g., manidipine, nifedipine, amlodipine, efonidipine, nicardipine), potassium channel openers (e.g., levcromakalim, L-27152, AL 0671, NIP-121), clonidine and the like.

Examples of the antiobesity agents include antiobesity agents acting on the central nervous system (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compounds described in WO01/82925 and WO01/87834); neuropeptide γ antagonists (e.g., CP-422935); cannabinoid receptor antagonists (e.g., SR-141716, SR-147778); ghrelin antagonists); pancreatic lipase inhibitors (e.g., orlistat, ATL-962), β3 agonists (e.g., AJ-9677), peptide anorexiants (e.g., leptin, CNTF (Ciliary Neurotropic Factor)), cholecystokinin agonists (e.g., lintitript, FPL-15849), feeding deterrents (e.g., P-57) and the like.

Examples of the diuretics include xanthine derivatives (e.g., sodium salicylate and theobromine, calcium salicylate and theobromine), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide), antialdosterone preparations (e.g., spironolactone, triamterene), carbonate dehydratase inhibitors (e.g., acetazolamide), chlorobenzenesulfonamide preparations (e.g., chlortalidone, mefruside, indapamide), azosemide, isosorbide, etacrynic acid, piretanide, bumetanide, furosemide and the like.

Examples of the chemotherapeutic agents include alkylating agents (e.g., cyclophosphamide, ifosfamide), metabolic antagonists (e.g., methotrexate, 5-fluorouracil and derivatives thereof), antitumor antibiotics (e.g., mitomycin, adriamycin), plant-derived antitumor agents (e.g., vincristine, vindesine, Taxol), cisplatin, carboplatin, etoposide and the like. Of these, Furtulon or NeoFurtulon, which are 5-fluorouracil derivatives, and the like are preferable.

Examples of the immunotherapeutic agents include microorganism or bacterial components (e.g., muramyl dipeptide derivatives, Picibanil), polysaccharides having immunity potentiating activity (e.g., lentinan, schizophyllan, krestin), cytokines obtained by genetic engineering techniques (e.g., interferon, interleukin (IL)), colony stimulating factors (e.g., granulocyte colony stimulating factor, erythropoietin) and the like, with preference given to interleukins such as IL-1, IL-2, IL-12 and the like.

Examples of the antithrombotic agents include heparin (e.g., heparin sodium, heparin calcium, dalteparin sodium), warfarins (e.g., warfarin potassium), anti-thrombin drugs (e.g., aragatroban), thrombolytic agents (e.g., urokinase, tisokinase, alteplase, nateplase, monteplase, pamiteplase), platelet aggregation inhibitors (e.g., ticlopidine hydrochloride, cilostazol, ethyl icosapentate, beraprost sodium, sarpogrelate hydrochloride) and the like.

Examples of the therapeutic agents for osteoporosis include alfacalcidol, calcitriol, elcatonin, calcitonin salmon, estriol, ipriflavone, risedronate disodium, pamidronate disodium, alendronate sodium hydrate, incadronate disodium and the like.

Examples of the antidementia agents include tacrine, donepezil, rivastigmine, galanthamine and the like.

Examples of the erectile dysfunction improvers include apomorphine, sildenafil citrate and the like.

Examples of the therapeutic agents for pollakiuria or urinary incontinence include flavoxate hydrochloride, oxybutynin hydrochloride, propiverine hydrochloride and the like.

Examples of the therapeutic agents for dysuria include acetylcholine esterase inhibitors (e.g., distigmine) and the like.

Furthermore, drugs having a cachexia-improving action established in animal models and clinical situations, such as cyclooxygenase inhibitors (e.g., indomethacin), progesterone derivatives (e.g., megestrol acetate), glucosteroids (e.g., dexamethasone), metoclopramide agents, tetrahydrocannabinol agents, fat metabolism improving agents (e.g., eicosapentanoic acid), growth hormones, IGF-1, or antibodies to a cachexia-inducing factor such as TNF-α, LIF, IL-6, oncostatin M and the like, can be used in combination with the compound of the present invention.

The combination drug is preferably insulin preparation, insulin sensitizer, α-glucosidase inhibitor, biguanide, insulin secretagogue (preferably sulfonylurea) and the like.

Two or more kinds of the above-mentioned combination drugs may be used in an appropriate ratio.

When the compound of the present invention is used in combination with a combination drug, the amount thereof can be reduced within a safe range in consideration of counteraction of these agents. Particularly, the dose of an insulin sensitizer, an insulin secretagogue (preferably a sulfonylurea) and a biguanide can be reduced as compared with the normal dose. Therefore, an adverse effect which may be caused by these agents can be prevented safely. In addition, the dose of the therapeutic agent for diabetic complications, therapeutic agent for hyperlipemia and antihypertensive agent can be reduced whereby an adverse effect which may be caused by these agents can be prevented effectively.

Compound (I) can be produced by, for example, the methods shown in the following reaction schemes 1 to 7.

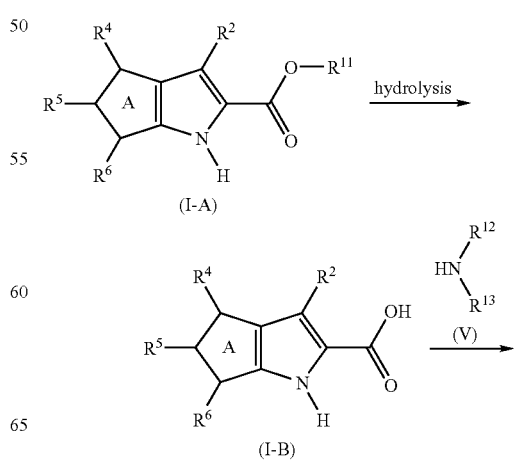

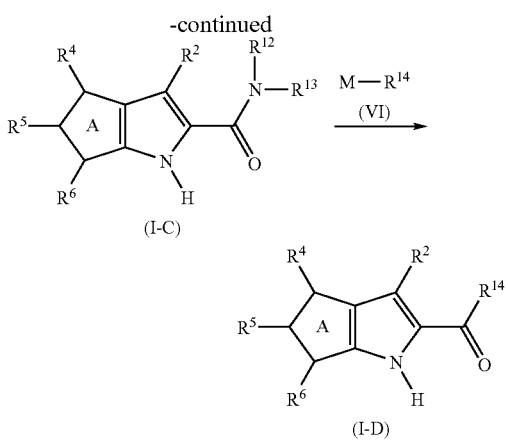

wherein $R^{11}$ is alkyl group, $R^{12}$ and $R^{13}$ are each independently hydrogen atom or substituent, $R^{14}$ is optionally substituted hydrocarbon group, M is metal (e.g., potassium, sodium, lithium, magnesium, copper, mercury, zinc, thallium, boron, tin and the like, which may form a complex), and other symbols are as defined above.

As the "substituent" for $R^{12}$ or $R^{13}$, those exemplified as the substituent of the "optionally substituted amino group" for $R^3$ can be mentioned.

Examples of the "optionally substituted hydrocarbon group" for $R^{14}$ include those exemplified as the "optionally substituted hydrocarbon group" for $R^3$.

Compound (I-B) can be produced by subjecting compound (I-A) to a hydrolysis. The hydrolysis is performed according to a conventional method using an acid or base.

Examples of the acid include mineral acids such as hydrochloric acid, sulfuric acid and the like; Lewis acids such as boron trichloride, boron tribromide and the like; organic acids such as trifluoroacetic acid, p-toluenesulfonic acid, etc. and the like. The Lewis acid can also be used in combination with thiol or sulfide.

Examples of the base include alkali metal hydroxide such as lithium hydroxide, sodium hydroxide, potassium hydroxide, barium hydroxide and the like; alkali metal carbonate such as sodium carbonate, potassium carbonate and the like; alkali metal $C_{1-6}$ alkoxide such as sodium methoxide, sodium ethoxide, potassium tert-butoxide and the like; organic bases such as triethylamine, imidazole, formamidine, etc. and the like.

The amount of these acids and bases to be used is generally about 0.5 to 10 mol, preferably about 0.5 to 6 mol, per 1 mol of compound (I-A).

The hydrolysis is performed without solvent or in a solvent inert to the reaction. Such solvent is not particularly limited as long as the reaction proceeds. For example, alcohols such as methanol, ethanol, propanol and the like; aromatic hydrocarbons such as benzene, toluene and the like; saturated hydrocarbons such as cyclohexane, hexane and the like; organic acids such as formic acid, acetic acid and the like; ethers such as tetrahydrofuran, 1,4-dioxane, 1,2-dimethoxyethane and the like; amides such as N,N-dimethylformamide, N,N-dimethylacetamide and the like; halogenated hydrocarbons such as dichloromethane, chloroform, carbon tetrachloride, 1,2-dichloroethane and the like; nitriles such as acetonitrile, propionitrile and the like; ketones such as acetone, methylethylketone and the like; sulfoxides such as dimethylsulfoxide and the like; water and the like can be mentioned. Two or more kinds of these solvents may be mixed at appropriate ratios for use.

The reaction time is generally from 10 min to 60 hr, preferably from 10 min to 12 hr. The reaction temperature is generally from −10° C. to 200° C., preferably from 0° C. to 120° C.

Compound (I-C) can be produced by reacting compound (I-B) or a reactive derivative in carboxy group thereof or a salt thereof with compound (V).

Examples of the reactive derivative in a carboxy group of compound (I-B) include
1) acid chloride;
2) acid azide;
3) mixed acid anhydride with acid (e.g., substituted phosphoric acid such as dialkylphosphoric acid, phenylphosphoric acid, diphenylphosphoric acid, dibenzylphosphoric acid, halogenated phosphoric acid and the like; dialkylphosphorous acid; sulfurous acid; thiosulfuric acid; sulfuric acid; sulfonic acid such as methanesulfonic acid and the like; aliphatic carboxylic acid such as formic acid, acetic acid, propionic acid, butyric acid, isobutyric acid, pivalic acid, pentanoic acid, isopentanoic acid, trichloroacetic acid and the like; aromatic carboxylic acid such as benzoic acid and the like);
4) symmetric acid anhydride;
5) activated amide with imidazole, 4-substituted imidazole, dimethylpyrazole, triazole or tetrazole;
6) activated ester (for example, cyanomethyl ester, methoxymethyl ester, dimethyliminomethyl ester, vinyl ester, propargyl ester, p-nitrophenyl ester, trichlorophenyl ester, pentachlorophenyl ester, mesylphenyl ester, phenylazophenyl ester, phenyl thioester, p-nitrophenyl ester, p-cresyl thioester, carboxymethyl thioester, pyranyl ester, pyridyl ester, piperidyl ester, 8-quinolyl thioester and the like);
7) ester with N-hydroxy compound (e.g., N,N-dimethylhydroxyamine, 1-hydroxy-2-(1H)-pyridone, N-hydroxysuccinimide, N-hydroxyphthalimide, 1-hydroxy-1H-benzotriazole); and the like. These reactive derivatives can be freely selected according to the kind of compound (I-B) to be used.

Preferable salts of the reactive derivative of compound (I-B) include basic salts such as alkali metal salt such as sodium salt, potassium salt and the like; alkaline earth metal salt such as calcium salt, magnesium salt and the like; ammonium salt; organic base salt such as trimethylamine salt, triethylamine salt, pyridine salt, picoline salt, dicyclohexylamine salt, N,N-dibenzylethylenediamine salt and the like; and the like.

This reaction is preferably performed in a solvent inert to the reaction. Such solvent is not particularly limited as long as the reaction proceeds and, for example, ethers such as 1,4-dioxane, tetrahydrofuran, diethyl ether, tert-butyl methyl ether, diisopropyl ether, 1,2-dimethoxyethane and the like; esters such as ethyl formate, ethyl acetate, n-butyl acetate and the like; halogenated hydrocarbons such as dichloromethane, chloroform, carbon tetrachloride, trichloroethylene and the like; hydrocarbons such as hexane, benzene, toluene and the like; amides such as formamide, N,N-dimethylformamide, N,N-dimethylacetamide and the like; nitriles such as acetonitrile, propionitrile, etc. and the like; sulfoxides such as dimethylsulfoxide and the like; sulfolane; hexamethylphosphoramide and the like can be mentioned. Two or more kinds of these solvents may be mixed at appropriate ratios for use.

In this reaction, when compound (I-B) is used in the form of a free acid or a salt thereof, the reaction is desirably performed in the presence of a conventionally-used condensation agent, for example, carbodiimide such as N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide and the like; N,N'-carbonylbis(2-methylimidazole); trialkyl phosphite; polyphosphate such as ethyl polyphosphate, isopropyl polyphosphate and the like; phosphorus oxychloride; diphenylphosphoryl azide; thionyl chloride; oxalyl chloride; lower alkyl haloformate such as ethyl chloroformate, isopropyl chloroformate and the like; triphenylphosphine; N-hydroxybenzotriazole; 1-(p-chlorobenzenesulfonyloxy)-6-chloro-1H-benzotriazole; a so-called Vilsmeier reagent prepared by a reaction of N,N'-dimethylformamide and thionyl chloride, phosgene, trichloromethyl chloroformate, phosphorus oxychloride and the like, and the like.

Where desired, this reaction may be performed in the presence of a base.

Examples of the base include alkali metal hydrides such as sodium hydride, potassium hydride and the like; alkali metal hydroxides such as lithium hydroxide, sodium hydroxide, potassium hydroxide and the like; alkaline earth metal hydroxides such as magnesium hydroxide, calcium hydroxide and the like; alkaline metal carbonates such as sodium carbonate, potassium carbonate and the like; alkali metal hydrogen carbonates such as sodium hydrogen carbonate, potassium hydrogen carbonate and the like; alkali metal alkoxides having 1 to 6 carbon atoms such as sodium methoxide, sodium ethoxide, sodium tert-butoxide and the like; organic bases such as trimethylamine, triethylamine, diisopropylethylamine, pyridine, 4-dimethylaminopyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like; organic lithiums such as methyllithium, n-butyllithium, sec-butyllithium, tert-butyllithium and the like; lithium amides such as lithium diisopropylamide, etc. and the like.

The amount of compound (V) to be used is generally 1 to 10 mol, preferably 1 to 3 mol, per 1 mol of compound (I-B). The amount of the base to be used is generally 1 to 10 mol, preferably 1 to 3 mol, per 1 mol of compound (I-B).

The reaction temperature is generally from −30° C. to 100° C. The reaction time is generally 0.5 hr to 20 hr.

When a mixed acid anhydride is used as a reactive derivative of compound (I-B), compound (I-B) and chloroformate (e.g., methyl chloroformate, ethyl chloroformate isobutyl chloroformate) may be reacted in the presence of a base (e.g., triethylamine, N-methylmorpholine, N,N-dimethylaniline, sodium hydrogen carbonate, sodium carbonate, potassium carbonate) and then further reacted with compound (V).

This reaction is preferably performed in a solvent inert to the reaction. Such solvent is not particularly limited as long as the reaction proceeds. For example, ethers such as 1,4-dioxane, tetrahydrofuran, diethyl ether, tert-butyl methyl ether, diisopropyl ether, 1,2-dimethoxyethane and the like; esters such as ethyl formate, ethyl acetate, n-butyl acetate and the like; halogenated hydrocarbons such as dichloromethane, chloroform, carbon tetrachloride, trichloroethylene and the like; hydrocarbons such as hexane, benzene, toluene and the like; amides such as formamide, N,N-dimethylformamide, N,N-dimethylacetamide and the like; nitriles such as acetonitrile, propionitrile, etc. and the like; sulfoxides such as dimethylsulfoxide and the like; sulfolane; hexamethylphosphoramide and the like can be mentioned. Two or more kinds of these solvents may be mixed at appropriate ratios for use.

The amount of compound (V) to be used is generally, 1 to 10 mol, preferably 1 to 3 mol, per 1 mol of compound (I-B).

The reaction temperature is generally from −30° C. to 100° C. The reaction time is generally 0.5 hr to 20 hr.

Compound (I-D) can be produced by reacting compound (I-C) with compound (VI).

Preferable examples of compound (VI) include organic lithiums such as methyl lithium, n-butyl lithium, phenyl lithium and the like; Grignard reagents such as methyl magnesium bromide, methyl magnesium chloride, phenyl magnesium bromide and the like.

This reaction is preferably performed in a solvent inert to the reaction. Such solvent is not particularly limited as long as the reaction proceeds. For example, ethers such as 1,4-dioxane, tetrahydrofuran, diethyl ether, tert-butyl methyl ether, diisopropyl ether, 1,2-dimethoxyethane and the like; hydrocarbons such as n-hexane, benzene, toluene, etc. and the like can be mentioned. Two or more kinds of these solvents may be mixed at appropriate ratios for use.

In addition, when compound (I-C) has an acidic proton in the molecule, it may be sometimes preferable to convert acidic proton to alkali metal salt by treating compound (I-C) with an alkali metal base before reaction with compound (VI). Examples of the base include alkali metal hydroxides such as lithium hydroxide, sodium hydroxide, potassium hydroxide, barium hydroxide and the like; alkaline metal carbonates such as sodium carbonate, potassium carbonate and the like; alkali metal $C_{1-6}$ alkoxides such as sodium methoxide, sodium ethoxide, potassium tert-butoxide and the like; alkali metal hydrides such as sodium hydride, etc. and the like.

The amount of compound (VI) to be used is generally 1 to 10 mol, preferably 1 to 3 mol, per 1 mol of compound (I-C).

The reaction temperature is generally from −30° C. to 100° C. The reaction time is generally 0.5 hr to 20 hr.

Compound (I-A) to be used as a starting material in Reaction Scheme 1 can be produced according to a method known per se or the method shown in the aforementioned Reaction Scheme 6. Compounds (V) and (VI) can be produced according to a method known per se.

Reaction scheme 2

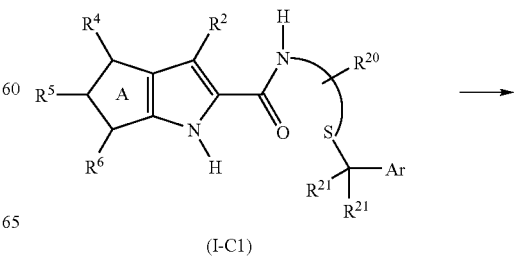

(I-C1)

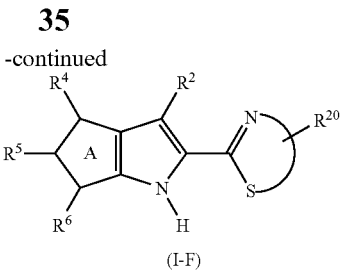

(I-F)

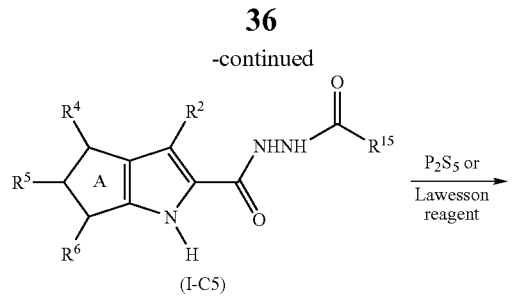

(I-C5)

wherein R[20] is a hydrogen atom or a substituent, R[21] is a hydrogen atom or a phenyl group, Ar is a phenyl group or a 4-methoxyphenyl group, and other symbols are as defined above.

Examples of the "substituent" for R[20] include those exemplified as the substituents of the "optionally substituted 5- to 7-membered heterocyclic group" for R[1]. R[20] may have 1 to 6 substituents at any positions, and when two or more R[20] are present, respective R[20] may be of the same or different kind. When two R[20] are present on the same carbon atom on the ring, the two R[20] may be bonded to each other to form an "optionally substituted ring". Examples of the "optionally substituted ring" include those similar to the "optionally substituted ring" formed by two substituents bonded to each other on the ring of the "optionally substituted 5- to 7-membered heterocyclic group" for R[1].

Compound (I-F) can be produced according to the method described in *Angew. Chem., Int. Ed.,* 2003, vol. 42, page 83, Tetrahedron, 1999, vol. 55, page 10271 and the like, by reacting compound (I-C1) with triphenylphosphine oxide and trifluoromethanesulfonic anhydride, or phosphorus pentachloride.

This reaction is performed without solvent or in a solvent inert to the reaction. Such solvent is not particularly limited as long as the reaction proceeds. For example, ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; nitriles such as acetonitrile, propionitrile, etc. and the like can be mentioned. Two or more kinds of these solvents may be mixed at appropriate ratios for use.

The amount of compound (I-C1), triphenylphosphine oxide, and trifluoromethanesulfonic anhydride or phosphorus pentachloride to be used is generally 1 to 10 mol, preferably 1 to 6 mol, per 1 mol of compound (I-C1).

The reaction temperature is generally −30° C. to 100° C. The reaction time is generally 0.5 hr to 20 hr.

Compound (I-C1) to be used as a starting material in reaction scheme 2 can be produced, for example, in the same manner as in the step to produce compound (I-C) in the aforementioned reaction scheme 1.

Reaction scheme 3

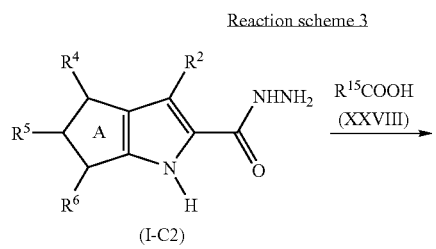

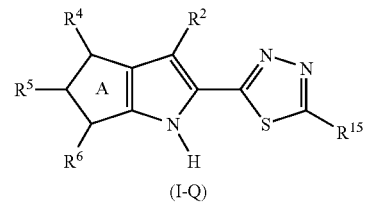

(I-Q)

wherein R[15] is a hydrogen atom or a substituent, and other symbols are as defined above.

Examples of the "substituent" for R[15] include those exemplified as the substituents of the "optionally substituted 5- to 7-membered heterocyclic group" for R[1].

Compound (I-C5) can be produced by reacting compound (I-C2) with compound (XXVIII) or a reactive derivative thereof.

Examples of the reactive derivative of compound (XXVIII) include those exemplified as the reactive derivative of the carboxy group of compound (I-B).

In addition, this reaction is performed in the same manner as in the reaction of compound (I-B) or a reactive derivative at the carboxy group thereof or a salt thereof with compound (V) in reaction scheme 1.

Compound (I-Q) can be produced by reacting compound (I-C5) with diphosphorus pentasulfide or Lawesson reagent.

This reaction is performed without solvent or in a solvent inert to the reaction. Such solvent is not is particularly limited as long as the reaction proceeds. For example, ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane, etc. and the like. Two or more kinds of these solvents may be mixed at appropriate ratios for use.

The amount of the diphosphorus pentasulfide or Lawesson reagent to be used is generally 1 to 10 mol, preferably 1 to 3 mol, per 1 mol of compound (I-C5).

The reaction temperature is generally −30° C. to 100° C. The reaction time is generally 0.5 hr to 20 hr.

Compound (XXVIII) to be used as a starting material in reaction scheme 3 can be produced according to a method known per se.

Compound (I-C2) to be used as a starting material in reaction scheme 3 can be produced, for example, from compound (I-B) in the same manner as in the production step of compound (I-C) in the aforementioned reaction scheme 1.

Reaction scheme 4

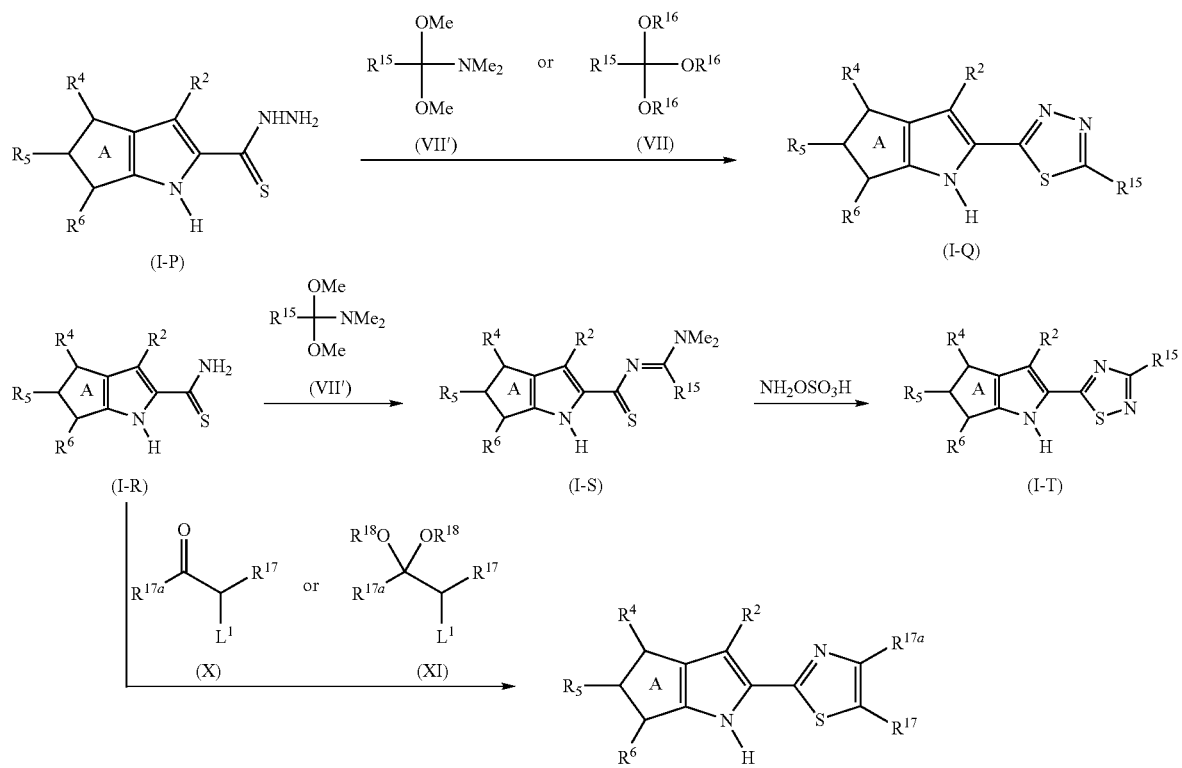

wherein $R^{16}$ is a $C_{1-6}$ alkyl group, $R^{17a}$ and $R^{17}$ are each independently a hydrogen atom or a substituent, $R^{18}$ is a $C_{1-6}$ alkyl group, $L^1$ is a leaving group, and other symbols are as defined above.

Examples of the substituent for $R^{17a}$ or $R^{17}$ include those exemplified as the substituents of the "optionally substituted 5- to 7-membered heterocyclic group" for $R^1$.

Examples of the "leaving group" for $L^1$ include a halogen atom; an optionally halogenated $C_{1-6}$ alkylsulfonyloxy group (e.g., methanesulfonyloxy, ethanesulfonyloxy, trichloromethanesulfonyloxy, trifluoromethanesulfonyloxy); a $C_{6-10}$ arylsulfonyloxy group optionally having 1 to 3 substituents selected from $C_{1-6}$ alkyl group, a $C_{1-6}$ alkoxy group and a nitro group (e.g., phenylsulfonyloxy, m-nitrophenylsulfonyloxy, p-toluenesulfonyloxy); a $C_{1-6}$ alkoxysulfonyloxy group; a $C_{6-10}$ aryloxysulfonyloxy group; a $C_{1-6}$ alkoxy group; a di-$C_{1-6}$ alkylamino group and the like.

Compound (I-Q) can be produced by reacting compound (I-P) with compound (VII') or compound (VII).

This reaction is performed without solvent or in a solvent inert to the reaction. Such solvent is not particularly limited as long as the reaction proceeds. For example, ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoric triamide, etc. and the like can be mentioned. Two or more kinds of these solvents may be mixed at appropriate ratios for use.

In this reaction, the reaction can be promoted by generally using an acid catalyst. Examples of the acid catalyst include mineral acid such as hydrochloric acid, sulfuric acid and the like; Lewis acid such as boron trihalide (e.g., boron trichloride, boron trifluoride), titanium tetrahalide (e.g., titanium tetrachloride, titanium tetrabromide), aluminum halide (e.g., aluminum chloride, aluminum bromide) and the like; organic acid such as acetic acid, formic acid, trifluoroacetic acid, etc. and the like.

The amount of compound (VII') or compound (VII) and acid catalyst to be used is generally 1 to 10 mol, preferably 1 to 3 mol, per 1 mol of compound (I-P), respectively.

The reaction temperature is generally −30° C. to 100° C. The reaction time is generally 0.5 hr to 20 hr.

Compound (I-T) can be produced in two steps from compound (I-R) according to a method described in Journal of Organic Chemistry (J. Org. Chem.), 1984, vol. 49, page 4800.

In Step 1, compound (I-S) can be produced by reacting compound (I-R) with compound (VII') without solvent or in a solvent inert to the reaction.

As the solvent to be used for this reaction, those exemplified for the aforementioned reaction of compound (I-P) with compound (VII') or compound (VII) can be mentioned.

The amount of compound (VII') to be used is generally 1 to 10 mol, preferably 1 to 3 mol, per 1 mol of compound (I-R).

The reaction temperature is generally from −30° C. to 100° C. The reaction time is generally 0.5 hr to 20 hr.

In step 2, compound (I-T) can be produced by reacting compound (I-S) with hydroxylamine-O-sulfonic acid.

When desired, this reaction is performed in the presence of an acid catalyst or a base. Examples of the acid catalyst include mineral acid such as hydrochloric acid, sulfuric acid and the like; organic acid such as acetic acid, formic acid, trifluoroacetic acid and the like. Examples of the base include alkali metal hydroxide such as lithium hydroxide, sodium hydroxide, potassium hydroxide and the like; alkaline earth metal hydroxide such as magnesium hydroxide, calcium hydroxide and the like; alkali metal carbonate such as sodium carbonate, potassium carbonate and the like; alkali metal hydrogen carbonate such as sodium hydrogen carbonate, potassium hydrogen carbonate and the like; alkali metal $C_{1-6}$ alkoxide such as sodium methoxide, sodium ethoxide, potassium tert-butoxide and the like; organic bases such as trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene, etc. and the like.

This reaction is performed without solvent or in a solvent inert to the reaction. As such solvent, those exemplified for the reaction of compound (I-P) with compound (VII') or compound (VII) can be mentioned.

The amount of hydroxylamine-O-sulfonic acid and base to be used is each generally 1 to 10 mol, preferably 1 to 3 mol, per 1 mol of compound (I-S).

The reaction temperature is generally from −30° C. to 100° C. The reaction time is generally 0.5 hr to 20 hr.

Compound (I-U) can be produced by reacting compound (I-R) with compound (X) or compound (XI).

When desired, this reaction is performed in the presence of a base. Examples of the base include organic base such as triethylamine, pyridine, 4-dimethylaminopyridine, diisopropylethylamine and the like; inorganic base such as sodium hydroxide, potassium hydroxide, sodium carbonate, potassium carbonate, etc. and the like.

This reaction is performed without solvent or in a solvent inert to the reaction. As such solvent, those exemplified for the reaction of compound (I-P) with compound (VII') or compound (VII) can be mentioned.

The amount of compound (X) or compound (XI), and base to be used is generally 1 to 10 mol, preferably 1 to 3 mol, per 1 mol of compound (I-R).

The reaction temperature is generally from −30° C. to 100° C. The reaction time is generally 0.5 hr to 20 hr.

Compounds (I-P) and (I-R) to be used as starting materials in reaction scheme 4 can be produced, for example, according to the method shown in reaction scheme 5. In addition, compounds (VII'), (VII) (X) and (XI) can be produced according to a method known per se.

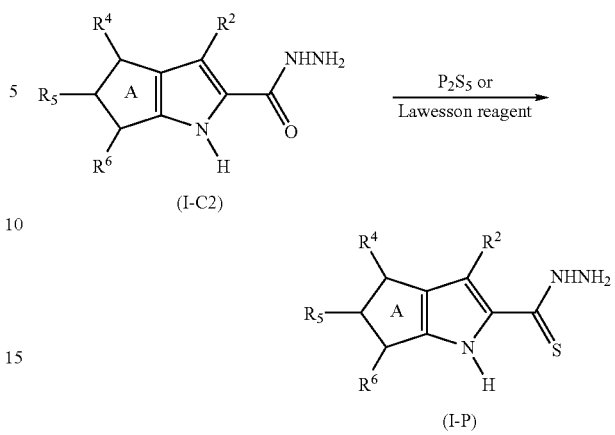

wherein each symbol is as defined above.

Compound (I-R) can be produced by reacting compound (I-C3) with diphosphorus pentasulfide or Lawesson reagent.

This reaction is performed without solvent or in a solvent inert to the reaction. Such solvent is not particularly limited as long as the reaction proceeds. For example, ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane, etc. and the like can be mentioned. Two or more kinds of these solvents may be mixed at appropriate ratios for use.

The amount of diphosphorus pentasulfide or Lawesson reagent to be used is generally 1 to 10 mol, preferably 1 to 3 mol, per 1 mol of compound (I-C3).

The reaction temperature is generally from −30° C. to 100° C. The reaction time is generally 0.5 hr to 20 hr.

Compound (I-C3) can be produced, for example, by a method similar to the step for producing compound (I-C) in the aforementioned reaction scheme 1.

Compound (I-P) can be produced by reacting compound (I-C2) with diphosphorus pentasulfide or Lawesson reagent. This reaction is performed in the same manner as in the aforementioned reaction of compound (I-C3) with diphosphorus pentasulfide or Lawesson reagent.

Reaction scheme 5

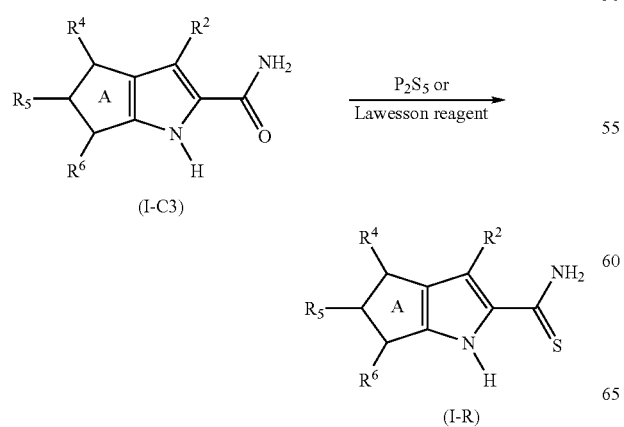

Reaction scheme 6

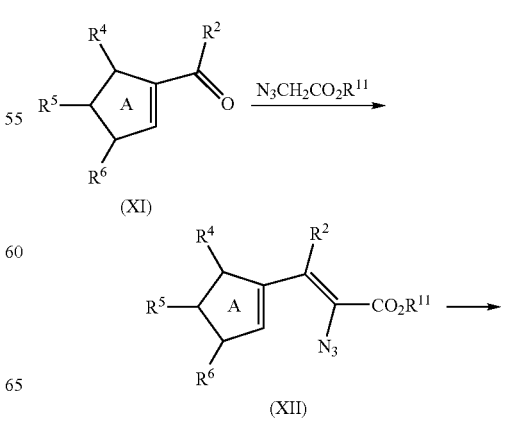

-continued

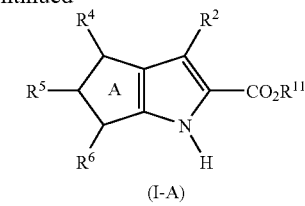

(I-A)

wherein each symbol is as defined above.

Compound (XII) can be produced by reacting compound (XI) with azidoacetic acid ester.

When desired, this reaction is performed in the presence of a base. Examples of the base include alkali metal hydroxide such as lithium hydroxide, sodium hydroxide, potassium hydroxide and the like; alkaline earth metal hydroxide such as magnesium hydroxide, calcium hydroxide and the like; alkali metal carbonate such as sodium carbonate, potassium carbonate and the like; alkali metal hydrogen carbonate such as sodium hydrogen carbonate, potassium hydrogen carbonate and the like; alkali metal $C_{1-6}$ alkoxide such as sodium methoxide, sodium ethoxide, sodium tert-butoxide and the like; organic bases such as trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene, etc. and the like.

This reaction is performed without solvent or in a solvent inert to the reaction. Such solvent is not particularly limited as long as the reaction proceeds. For example, alcohols such as methanol, ethanol, propanol and the like; aromatic hydrocarbons such as benzene, toluene and the like; saturated hydrocarbons such as cyclohexane, hexane and the like; ethers such as tetrahydrofuran, 1,4-dioxane, 1,2-dimethoxyethane and the like; amides such as N,N-dimethylformamide, N,N-dimethylacetamide and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like; water and the like can be mentioned. Two or more kinds of these solvents may be mixed at appropriate ratios for use.

The reaction time is generally 10 min to 60 hr, preferably 10 min to 12 hr. The reaction temperature is generally –70° C. to 200° C., preferably –30° C. to 120° C.

The amount of the azidoacetic acid ester to be used is generally 1 to 10 mol, preferably 1 to 5 mol, per 1 mol of compound (XI).

Compound (I-A) can be produced by subjecting compound (XII) to ring closing reaction.

This reaction is performed without solvent or in a solvent inert to the reaction. Such solvent is not particularly limited as long as the reaction proceeds. For example, alcohols such as methanol, ethanol, propanol and the like; aromatic hydrocarbons such as benzene, toluene and the like; saturated hydrocarbons such as cyclohexane, hexane and the like; organic acids such as formic acid, acetic acid and the like; ethers such as tetrahydrofuran, 1,4-dioxane, 1,2-dimethoxyethane and the like; amides such as N,N-dimethylformamide, N,N-dimethylacetamide and the like; halogenated hydrocarbons such as dichloromethane, chloroform, carbon tetrachloride, 1,2-dichloroethane and the like; nitriles such as acetonitrile, propionitrile and the like; ketones such as acetone, methylethyl ketone and the like; sulfoxides such as dimethylsulfoxide and the like; water and the like. Two or more kinds of these solvents may be mixed at appropriate ratios for use.

The reaction time is generally 10 min to 60 hr, preferably 10 min to 12 hr. The reaction temperature is generally –10° C. to 200° C., preferably 0° C. to 120° C.

Compound (XI) can be produced according to a method known per se or reaction scheme 7.

Reaction scheme 7

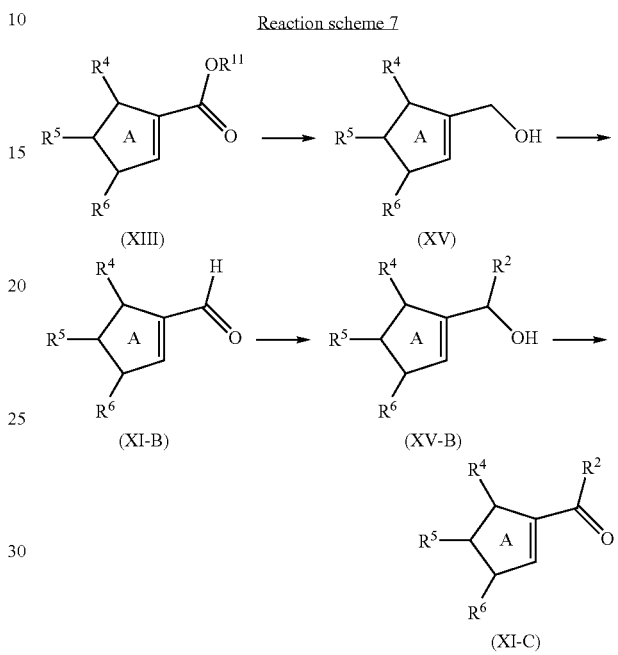

wherein each symbol is as defined above.

Compound (XV) can be produced by subjecting compound (XIII) to a reduction reaction. The reduction reaction is performed using a reducing agent according to a conventional method. Examples of the reducing agent include metal hydride such as aluminum hydride, diisobutylaluminum hydride, tributyltin hydride and the like; metal hydride complex compound such as lithium aluminum hydride, sodium borohydride and the like; borane complex such as borane tetrahydrofuran complex, borane dimethylsulfide complex and the like; alkyl boranes such as thexyl borane, disiamyl borane and the like; diborane; metals such as zinc, aluminum, tin, iron and the like; alkali metal such as sodium, lithium, etc./liquid ammonia (Birch reduction) and the like. The amount of the reducing agent to be used is appropriately determined according to the kind of the reducing agent. For example, the amount of metal hydride or metal hydride complex compound to be used is about 0.25 to about 10 mol, preferably about 0.5 to about 5 mol, per 1 mol of compound (XIII), the amount of borane complex, alkyl boranes or diborane to be used is generally about 1 to about 10 mol, preferably about 1 to about 5 mol, per 1 mol of compound (XIII), and the amount of metals (including alkali metal to be used for Birch reduction) to be used is about 1 to about 20 equivalents, preferably about 1 to about 5 equivalents, per 1 equivalent of compound (XIII).

The reduction reaction is advantageously performed using a solvent inert to the reaction. Such solvent is not particularly limited as long as the reaction proceeds. For example, solvents such as alcohols such as methanol, ethanol, 1-propanol, 2-propanol, tert-butyl alcohol and the like; ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like; organic acids such as formic acid, acetic acid, propionic acid, trifluoroacetic acid, methanesulfonic acid, and the like or mixed solvent thereof is preferable.

The reaction time is generally about 1 hr to about 100 hr, preferably about 1 hr to about 50 hr. The reaction temperature is generally about −20° C. to about 120° C., preferably about 0° C. to about 80° C.

Compound (XI-B) can be produced by subjecting compound (XV) to oxidation reaction. The oxidation reaction is performed using an oxidant according to a conventional method. Examples of the oxidant include activated manganese dioxide, pyridinium chlorochromate (PCC), pyridinium dichromate (PDC), 1,1,1-tris(acetyloxy)-1,1-dihydro-1,2-benziodoxol-3-(1H)-one (Dess-Martin Periodinane), dimethyl sulfoxide-acid anhydride (acetic anhydride, trifluoroacetic anhydride and the like), dimethyl sulfoxide-thionyl chloride, dimethyl sulfoxide-sulfuryl chloride, dimethyl sulfoxide-oxalyl chloride, dimethyl sulfoxide-chlorine, and dimethylsulfoxide-dicyclohexylcarbodiimide (DCC) in the presence of an acid (phosphoric acid, trifluoroacetic acid, dichloroacetic acid and the like) and the like.

The amount of the oxidant to be used is about 0.25 to about 10 mol, preferably about 0.5 to about 5 mol, per 1 mol of compound (XV).

The oxidation reaction is advantageously performed in a solvent inert to the reaction. Such solvent is not particularly limited as long as the reaction proceeds. For example, ethers such as 1,4-dioxane, tetrahydrofuran, diethyl ether, tert-butyl methyl ether, diisopropyl ether, 1,2-dimethoxyethane and the like; esters such as ethyl formate, ethyl acetate, n-butyl acetate and the like; halogenated hydrocarbons such as dichloromethane, chloroform, carbon tetrachloride, trichloroethylene and the like; hydrocarbons such as hexane, benzene, toluene and the like; amides such as formamide, N,N-dimethylformamide, N,N-dimethylacetamide and the like; nitriles such as acetonitrile, propionitrile, etc. and the like; sulfoxides such as dimethylsulfoxide and the like; sulfolane; hexamethylphosphoramide and the like; organic acids such as formic acid, acetic acid, propionic acid, trifluoroacetic acid, methanesulfonic acid, etc. and the like can be mentioned. Two or more kinds of these solvents may be mixed at appropriate ratios for use.

While the reaction time varies depending on the kind and amount of an oxidant to be used, it is generally about 1 hr to about 100 hr, preferably about 1 hr to about 50 hr. The reaction temperature is generally about −70° C. to about 120° C., preferably about −70° C. to about 80° C.

Compound (XV-B) can be produced by reacting compound (XI-B) with an organic metal reagent.

Preferable examples of the organic metal reagent include organic lithiums such as methyllithium, n-butyllithium, phenyllithium and the like; Grignard reagents such as methylmagnesium bromide, methylmagnesium chloride, phenylmagnesium bromide and the like.

This reaction is preferably performed in a solvent inert to the reaction. Such solvent is not particularly limited as long as the reaction proceeds. For example, ethers such as 1,4-dioxane, tetrahydrofuran, diethyl ether, tert-butyl methyl ether, diisopropyl ether, 1,2-dimethoxyethane and the like; hydrocarbons such as hexane, benzene, toluene, etc. and the like can be mentioned. Two or more kinds of these solvents may be mixed at appropriate ratios for use.

The amount of the organic metal reagent to be used is about 1 to about 10 mol, preferably about 1 to about 5 mol, per 1 mol of compound (XI-B).

The reaction time is generally about 1 hr to about 100 hr, preferably about 1 hr to about 50 hr. The reaction temperature is generally about −70° C. to about 120° C., preferably about −70° C. to about 80° C.

Compound (XI-C) can be produced by subjecting compound (XV-B) to oxidation reaction. This reaction is performed in the same manner as in the aforementioned oxidation reaction of compound (XV).

Compound (XIII) can be produced according to a method known per se.

In each of the above-mentioned production methods, when the starting material compound or the compound of the present invention has an amino group, carboxy group, hydroxy group or mercapto group, a protecting group conventionally used in peptide chemistry may be introduced into these groups, where the protecting group can be removed by a conventional deprotection method during any step of each reaction scheme.

Compound (I) can also be produced by subjecting the object compound obtained by each of the above-mentioned production methods to a substituent conversion reaction known per se.

The compound of the present invention obtained by each of the above-mentioned production methods can be isolated and purified by a known means such as concentration, concentration under reduced pressure, solvent extraction, crystallization, recrystallization, phase transfer, chromatography and the like. In addition, each starting material compound used for each of the above-mentioned production methods can be isolated and purified by a known means similar to the aforementioned means. On the other hand, these starting material compounds may be directly used in the form of a reaction mixture without isolation, as a starting material for the next step.

For production of the compound of the present invention, when the starting material compound can form a salt, the compound may be used as a salt. As such salt, for example, those recited as examples of the salt of the compound of the present invention can be mentioned.

When the compound of the present invention contains an optical isomer, steric isomer, positional isomer or rotamer, they are encompassed in the compound of the present invention and can be each obtained as single products by a synthetic means or separation means known per se. For example, when the compound of the present invention contains an optical isomer, an optical isomer resolved from the compound is also encompassed in the compound of the present invention.

The compound of the present invention may be a crystal.

A crystal of the compound of the present invention (hereinafter sometimes to be abbreviated as the crystal of the present invention) can be produced by crystallizing the compound of the present invention by applying a crystallization method known per se.

In the present specification, the melting point means a value measured, for example, using a trace melting point measurement device (YANACO, type MP-500D or Buchi, B-545) or DSC (differential scanning calorimetry analysis) apparatus (SEIKO, EXSTAR6000) and the like.

In general, the melting point may vary depending on the measurement device, measurement condition and the like. In the present specification, the crystal may have a melting point different from that described in the present specification, as long as the difference is within the general range of error.

The crystal of the present invention is superior in the physicochemical properties (e.g., melting point, solubility, stability) and biological properties (e.g., in vivo kinetics (absorbability, distribution, metabolism, excretion), efficacy expression) and is extremely useful as a pharmaceutical agent.

EXAMPLES

The present invention is explained in detail in the following by referring to the following Reference Examples, Examples, Experimental Examples and Formulation Examples, which are not to be construed as limitative. In addition, the present invention may be modified without departing from the scope of the invention.

The "room temperature" in the following Reference Examples and Examples indicates the range of generally from about 10° C. to about 35° C. As for "%", the yield is in mol/mol %, the solvent used for chromatography is in % by volume and other "%" is in % by weight. OH proton, NH proton etc. on proton NMR spectrum that could not be confirmed due to broad peak are not included in the data.

Other symbols used herein mean the following:
s: singlet
d: doublet
t: triplet
q: quartet
m: multiplet
br: broad
J: coupling constant
Hz: Hertz
CDCl$_3$: deuterated chloroform
DMSO-d$_6$: dimethyl sulfoxide-d$_6$
$^1$H-NMR: proton nuclear magnetic resonance
TFA: trifluoroacetic acid In the following Reference Examples and Examples, mass spectrum (MS) and nuclear magnetic resonance spectrum (NMR) were measured under the following conditions.
MS measurement tools: Waters Corporation ZMD, Waters Corporation ZQ2000 or Micromass Ltd., platform II
Ionization method: Electron Spray Ionization (ESI) or Atmospheric Pressure Chemical Ionization (APCI). Unless specifically indicated, ESI was used.
NMR measurement tools: Varian Inc. Varian Gemini 200 (200 MHz), Varian Gemini 300 (300 MHz), Bruker BioSpin Corp. AVANCE 300.

Reference Example 1

1-benzyl-2-methyl-1H-imidazole-4-carbaldehyde

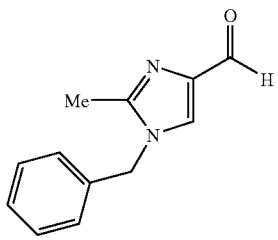 [SMILES: Cc1nc(C=O)cn1Cc1ccccc1]

To a solution of 2-methyl-1H-imidazole-4-carbaldehyde (5.50 g) in N,N-dimethylformamide (100 mL) was slowly added sodium hydride (60%, oily, 2.4 g) at 0° C., and the mixture was stirred at room temperature for 30 min. Benzyl bromide (7.1 mL) was slowly added to the reaction mixture, and the mixture was stirred overnight at room temperature. Water was added to the reaction mixture, and the mixture was extracted with ethyl acetate. The ethyl acetate layer was washed with saturated brine, dried (MgSO$_4$) and concentrated. The residue was subjected to silica gel column chromatography to give 1-benzyl-2-methyl-1H-imidazole-4-carbaldehyde (3.8 g, yield 38%) as colorless crystals from a fraction eluted with ethyl acetate-hexane (1:1, volume ratio). melting point 61° C.

Reference Example 2

4-bromo-5-methylthiophene-2-carbaldehyde

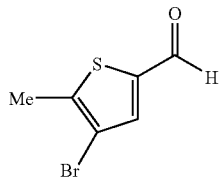

To a solution of 5-methylthiophene-2-carbaldehyde (50.0 g) in acetic acid (400 mL) was added dropwise a solution of bromine (25 mL) in acetic acid (200 mL) at room temperature over 6 hr. After the dropwise addition, the reaction mixture was stirred overnight, neutralized with saturated aqueous sodium hydrogen carbonate solution, and extracted with ethyl acetate. The ethyl acetate layer was washed with saturated brine, dried (MgSO$_4$) and concentrated. The obtained residue was dissolved in toluene (50 mL), and the mixture was stirred at 110° C. for 2 hr and concentrated. The residue was subjected to silica gel column chromatography, eluted with ethyl acetate-hexane (1:5, volume ratio) and concentrated to give 4-bromo-5-methylthiophene-2-carbaldehyde (40.0 g, yield 50%) as yellow crystals. melting point 60° C.

Reference Example 3

2-(4-bromo-5-methyl-2-thienyl)-1,3-dioxolane

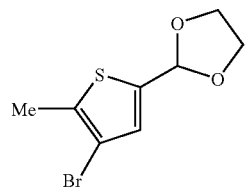 [SMILES: Cc1sc(C2OCCO2)cc1Br]

A mixture of 4-bromo-5-methylthiophene-2-carbaldehyde (6.0 g), ethylene glycol (100 mL), p-toluenesulfonic acid (2 mL) and toluene (100 mL) was heated under reflux for 5 hr with a Dean-Stark trap. The reaction mixture was washed with water and saturated brine, and the obtained organic layer was dried (MgSO$_4$) and concentrated. The residue was subjected to silica gel column chromatography to give 2-(4-bromo-5-methyl-2-thienyl)-1,3-dioxolane (6.96 g, yield 93%) as a yellow oil from a fraction eluted with ethyl acetate-hexane (1:5, volume ratio).

$^1$H-NMR (CDCl$_3$) δ: 2.37 (3H, s), 3.97-4.18 (4H, m), 5.99 (1H, s), 6.96 (1H, s).

Reference Example 4

5-formyl-2-methylthiophene-3-carboxylic acid

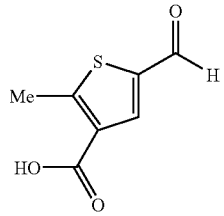 [SMILES: Cc1sc(C=O)cc1C(=O)O]

To a solution of 2-(4-bromo-5-methyl-2-thienyl)-1,3-dioxolane (5.0 g) in tetrahydrofuran (50 mL) was added dropwise n-butyl lithium (1.6M hexane solution, 12.5 mL) at −78° C. and, after the dropwise addition, the mixture was stirred for 1 hr. Carbon dioxide was blown into the reaction solution for 30 min. The reaction mixture was warmed to room temperature, saturated aqueous sodium hydrogen carbonate solution was added, and the mixture was extracted with ethyl acetate. The aqueous layer was acidified with 1N hydrochloric acid, and the mixture was extracted with ethyl acetate. The ethyl acetate layer was washed with saturated brine, dried (MgSO$_4$) and concentrated. The obtained residue was dissolved in tetrahydrofuran (50 mL), 1N hydrochloric acid (50 mL) was added, and the mixture was stirred at 50° C. for 1 hr. The reaction mixture was concentrated and extracted with ethyl acetate. The ethyl acetate layer was washed with saturated brine, dried (MgSO$_4$) and concentrated. The residue was subjected to silica gel column chromatography to give 5-formyl-2-methylthiophene-3-carboxylic acid (1.2 g, yield 36%) as yellow crystals from a fraction eluted with ethyl acetate-hexane (1:1, volume ratio). melting point 173° C.

Reference Example 5 benzyl(5-formyl-2-methyl-3-thienyl)carbamate

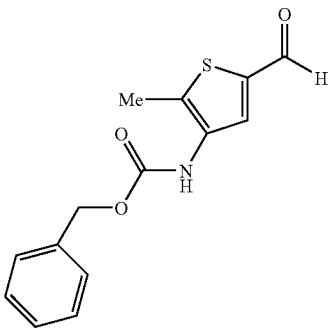 [SMILES: Cc1sc(C=O)cc1NC(=O)OCc1ccccc1]

A mixture of 5-formyl-2-methylthiophene-3-carboxylic acid (1.25 g), triethylamine (1.4 mL), diphenylphosphoryl azide (2.2 mL) and N,N-dimethylformamide (20 mL) was stirred for 1 hr under ice-cooling. Water was added to the reaction mixture, and the mixture was extracted with ethyl acetate. The ethyl acetate layer was washed with saturated brine, dried (MgSO$_4$) and concentrated. The obtained residue was dissolved in toluene (20 mL), and benzyl alcohol (0.7 mL) was added. The reaction mixture was stirred at 110° C. for 2 hr and concentrated. The residue was subjected to silica gel column chromatography to give benzyl (5-formyl-2-methyl-3-thienyl)carbamate (1.6 g, yield 80%) as yellow crystals from a fraction eluted with is ethyl acetate-hexane (1:3, volume ratio). melting point 120° C.

Reference Example 6 benzyl(5-formyl-2-methyl-3-thienyl)methylcarbamate

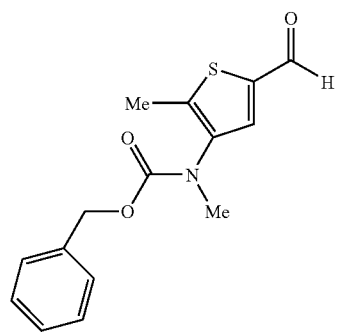 [SMILES: Cc1sc(C=O)cc1N(C)C(=O)OCc1ccccc1]

To a solution of benzyl (5-formyl-2-methyl-3-thienyl)carbamate (1.6 g) in N,N-dimethylformamide (20 mL) was slowly added sodium hydride (60%, oily, 0.3 g) at 0° C., and the mixture was stirred at room temperature for 30 min. Methyl iodide (0.47 mL) was added to the reaction mixture, and the mixture was stirred at room temperature for 1 hr. Water was added to the reaction mixture, and the mixture was extracted with ethyl acetate. The ethyl acetate layer was washed with saturated brine, dried (MgSO$_4$) and concentrated. The residue was subjected to silica gel column chromatography to give benzyl (5-formyl-2-methyl-3-thienyl)methylcarbamate (0.72 g, yield 43%) as a yellow oil from a fraction eluted with ethyl acetate-hexane (1:3, volume ratio).

$^1$H-NMR (CDCl$_3$) δ: 2.29 (3H, s), 3.22 (3H, s), 5.12 (2H, s), 7.21-7.50 (6H, m), 9.76 (1H, s).

Reference Example 7 methyl 5-methyl-4-nitrothiophene-2-carboxylate

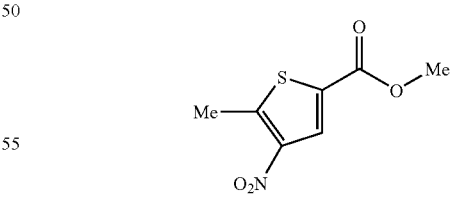

To nitric acid (specific gravity 1.42, 400 mL) cooled to −5° C. was dropwise added sulfuric acid (230 mL), and the mixture was stirred at −5° C. for 1 hr after the dropwise addition. 5-Methyl-thiophene-2-carboxylic acid (100 g) was added in small portions to the reaction mixture over 30 min. The reaction mixture was stirred for 1 hr, poured into ice and the precipitated crystals were collected by filtration. The crystals were washed with water and dried. The obtained crystals were dissolved in methanol (500 mL), sulfuric acid (100 mL) was added, and the mixture was heated under reflux overnight. The reaction mixture was concentrated, water was added, and the precipitated crystals were collected by filtration. The crystals were washed with water and dried to give methyl 5-methyl-4-nitrothiophene-2-carboxylate (95 g, yield 63%) as yellow crystals. melting point 81° C.

Reference Example 8 methyl 4-amino-5-methylthiophene-2-carboxylate

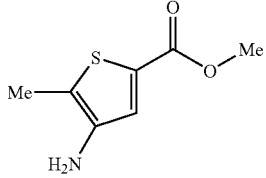 [SMILES: COC(=O)c1cc(N)c(C)s1]

A mixture of methyl 5-methyl-4-nitrothiophene-2-carboxylate (95 g) and 10% palladium-carbon (50% containing water, 10 g) in tetrahydrofuran (250 mL)-methanol (250 mL) was stirred at 50° C. for 8 hr under a hydrogen atmosphere (0.3 MPa). The catalyst was filtered off, and the filtrate was concentrated under reduced pressure. The obtained residue was crystallized from diethyl ether to give methyl 4-amino-5-methylthiophene-2-carboxylate (58 g, yield 72%) as yellow crystals. melting point 91° C.

Reference Example 9 methyl 5-methyl-4-[(2-thienylsulfonyl)amino]thiophene-2-carboxylate

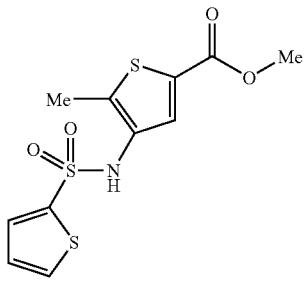 [SMILES: COC(=O)c1cc(NS(=O)(=O)c2cccs2)c(C)s1]

To a mixture of methyl 4-amino-5-methylthiophene-2-carboxylate (20 g) and pyridine (100 mL) was added 2-thiophensulfonyl chloride (23.5 g) at 0° C., and the mixture was stirred at room temperature for 2 hr. The reaction mixture was concentrated, water was added, and the mixture was extracted with ethyl acetate. The ethyl acetate layer was washed with saturated brine, dried (MgSO$_4$) and concentrated. The residue was subjected to silica gel column chromatography to give methyl 5-methyl-4-[(2-thienylsulfonyl)amino]thiophene-2-carboxylate (35.7 g, yield 96%) as pale-yellow crystals from a fraction eluted with ethyl acetate-hexane (1:3, volume ratio).

$^1$H-NMR (CDCl$_3$) δ: 2.20 (3H, s), 3.85 (3H, s), 6.46 (1H, brs), 7.60 (1H, dd, J=5.1 Hz, 3.9 Hz), 7.43-7.45 (2H, m), 7.61 (1H, dd, J=5.1 Hz, 1.5 Hz).

Reference Example 10 methyl 5-methyl-4-[methyl(2-thienylsulfonyl)amino]thiophene-2-carboxylate

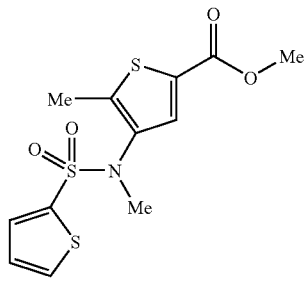 [SMILES: COC(=O)c1cc(N(C)S(=O)(=O)c2cccs2)c(C)s1]

To a solution of methyl 5-methyl-4-[(2-thienylsulfonyl)amino]thiophene-2-carboxylate (35.7 g) in N,N-dimethylformamide (200 mL) was slowly added sodium hydride (60%, oily, 5.2 g) at 0° C., and the mixture was stirred at room temperature for 30 min. Methyl iodide (8.0 mL) was added to the reaction mixture, and the mixture was stirred at room temperature for 1 hr. Water was added to the reaction mixture, and the mixture was extracted with ethyl acetate. The ethyl acetate layer was washed with saturated brine, dried (MgSO$_4$) and concentrated. The residue was subjected to silica gel column chromatography to give methyl 5-methyl-4-[methyl(2-thienylsulfonyl)amino]thiophene-2-carboxylate (37.5 g, yield 99%) as yellow crystals from a fraction eluted with ethyl acetate-hexane (1:3, volume ratio).

$^1$H-NMR (CDCl$_3$) δ: 2.48 (3H, s), 3.13 (3H, s), 3.82 (3H, s), 7.10 (1H, s), 7.13 (1H, dd, J=5.1 Hz, 3.6 Hz), 7.43 (1H, dd, J=3.6 Hz, 1.2 Hz), 7.65 (1H, dd, J=5.1 Hz, 1.2 Hz).

Reference Example 11

N-[5-(hydroxymethyl)-2-methyl-3-thienyl]-N-methylthiophene-2-sulfonamide

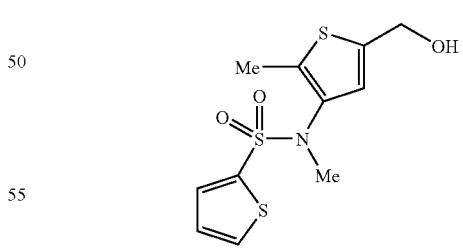

To a solution of methyl 5-methyl-4-[methyl(2-thienylsulfonyl)amino]thiophene-2-carboxylate (37.5 g) in tetrahydrofuran (200 mL) was slowly added lithium aluminum hydride (4.4 g) in small portions. The reaction mixture was stirred at room temperature for 1 hr, and water (4.4 mL), 15% aqueous sodium hydroxide solution (4.4 mL) and water (13.2 mL) were successively added to the reaction mixture under ice-cooling. The reaction mixture was stirred for 1 hr, and the insoluble material was filtered off. The filtrate was concentrated and crystallized from diethyl ether to give N-[5-(hydroxymethyl)-2-methyl-3-thienyl]-N-methylthiophene-2-sulfonamide (31.1 g, yield 91%) as yellow crystals.

$^1$H-NMR (CDCl$_3$) δ: 2.32 (3H, s), 3.12 (3H, s), 4.60 (2H, s), 6.35 (1H, s), 7.10 (1H, dd, J=5.1 Hz, 3.6 Hz), 7.43 (1H, dd, J=3.6 Hz, 1.2 Hz), 7.61 (1H, dd, J=5.1 Hz, 1.2 Hz).

Reference Example 12

N-(5-formyl-2-methyl-3-thienyl)-N-methylthiophene-2-sulfonamide

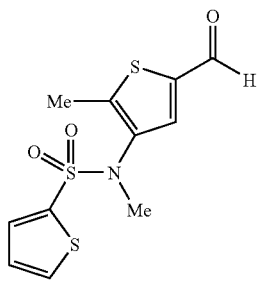 [SMILES: Cc1sc(C=O)cc1N(C)S(=O)(=O)c1cccs1]

To a solution of N-[5-(hydroxymethyl)-2-methyl-3-thienyl]-N-methylthiophene-2-sulfonamide (31.1 g) in tetrahydrofuran (300 mL) was added manganese dioxide (43 g), and the mixture was stirred at room temperature overnight. The manganese dioxide was filtered off and the filtrate was concentrated and crystallized from diethyl ether to give N-(5-formyl-2-methyl-3-thienyl)-N-methylthiophene-2-sulfonamide (26.4 g, yield 86%) as yellow crystals.

$^1$H-NMR (CDCl$_3$) δ: 2.50 (3H, s), 3.19 (3H, s), 7.19 (1H, s), 7.15 (1H, dd, J=5.1 Hz, 3.6 Hz), 7.44 (1H, dd, J=3.6 Hz, 1.2 Hz), 7.67 (1H, dd, J=5.1 Hz, 1.2 Hz), 9.66 (1H, s).

Reference Example 13 ethyl 4-amino-1-ethyl-1H-pyrrole-2-carboxylate

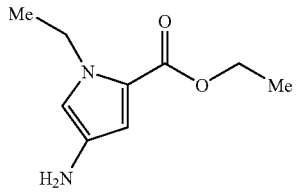 [SMILES: CCOC(=O)c1cc(N)cn1CC]

To a solution of ethyl 4-nitro-1H-pyrrol-2-carboxylate (10 g) in N,N-dimethylformamide (100 mL) was slowly added sodium hydride (60%, oily, 2.4 g) at 0° C., and the mixture was stirred at room temperature for 30 min. Ethyl iodide (4.8 mL) was slowly added to the reaction mixture, and the mixture was stirred at room temperature overnight. Water was added to the reaction mixture, and the mixture was extracted with ethyl acetate. The ethyl acetate layer was washed with saturated brine, dried (MgSO$_4$) and concentrated. A mixture of the residue and 10% palladium-carbon (50% containing water, 1.0 g) in tetrahydrofuran (20 mL)-ethanol (20 mL) was stirred at room temperature for 12 hr under a hydrogen atmosphere. The catalyst was filtered off, and the filtrate was concentrated under reduced pressure. The obtained residue was subjected to silica gel column chromatography to give ethyl 4- amino-1-ethyl-1H-pyrrole-2-carboxylate (7.1 g, yield 78%) as a brown oil from a fraction eluted with ethyl acetate-hexane (1:3, volume ratio).

$^1$H-NMR (CDCl$_3$) δ: 1.30-1.44 (6H, m), 2.96 (2H, brs), 4.18-4.28 (4H, m), 6.42 (1H, d, J=2.1 Hz), 6.47 (1H, d, J=2.1 Hz).

Reference Example 14 ethyl 1-ethyl-4-[methyl(2-thienylsulfonyl)amino]-1H-pyrrole-2-carboxylate

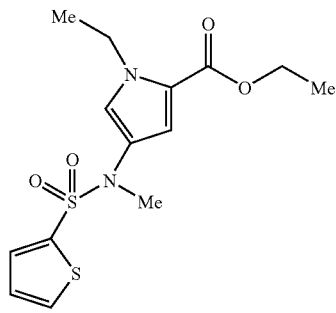 [SMILES: CCOC(=O)c1cc(N(C)S(=O)(=O)c2cccs2)cn1CC]

To a mixture of ethyl 4-amino-1-ethyl-1H-pyrrole-2-carboxylate (7.1 g) and pyridine (50 mL) was added 2-thiophensulfonyl chloride (8.4 g) at 0° C., and the mixture was stirred at room temperature for 2 hr. The reaction mixture was concentrated, water was added, and the mixture was extracted with ethyl acetate. The ethyl acetate layer was washed with saturated brine, dried (MgSO$_4$) and concentrated. To a solution of the residue in N,N-dimethylformamide (50 mL) was slowly added sodium hydride (60%, oily, 1.7 g) at 0° C., and the mixture was stirred at room temperature for 30 min. Methyl iodide (2.7 mL) was added to the reaction mixture, and the mixture was stirred at room temperature for 1 hr. Water was added to the reaction mixture, and the mixture was extracted with ethyl acetate. The ethyl acetate layer was washed with saturated brine, dried (MgSO$_4$) and concentrated. The residue was subjected to silica gel column chromatography to give ethyl 1-ethyl-4-[methyl(2-thienylsulfonyl)amino]-1H-pyrrole-2-carboxylate (11.9 g, yield 88%) as a yellow oil from a fraction eluted with ethyl acetate-hexane (1:1, volume ratio).

$^1$H-NMR (CDCl$_3$) δ: 1.31 (3H, t, J=7.5 Hz), 1.38 (3H, t, J=7.5 Hz), 3.13 (3H, s), 4.23 (2H, q, J=7.5 Hz), 4.31 (2H, q, J=7.5 Hz), 6.60 (1H, d, J=2.4 Hz), 6.89 (1H, d, J=2.4 Hz), 7.06 (1H, dd, J=4.8 Hz, 3.6 Hz), 7.38 (1H, dd, J=3.6 Hz, 1.5 Hz), 7.55 (1H, dd, J=4.8 Hz, 1.5 Hz).

Reference Example 15

N-(1-ethyl-5-formyl-1H-pyrrol-3-yl)-N-methylthiophene-2-sulfonamide

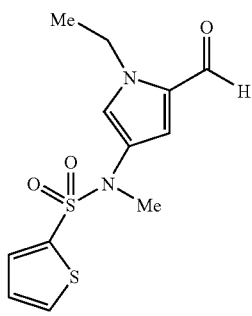 [SMILES: CCn1cc(N(C)S(=O)(=O)c2cccs2)cc1C=O]

To a solution of ethyl 1-ethyl-4-[methyl(2-thienylsulfonyl)amino]-1H-pyrrole-2-carboxylate (11.9 g) in tetrahydrofuran (200 mL) was slowly added lithium aluminum hydride (1.46 g) in small portions. The reaction mixture was stirred at room temperature for 1 hr, and water (1.5 mL), 15% aqueous sodium hydroxide solution (1.5 mL) and water (4.5 mL) were successively added to the reaction mixture under ice-cooling. The reaction mixture was stirred for 1 hr, the insoluble material was filtered off, and the filtrate was concentrated. To a solution of the residue in tetrahydrofuran (200 mL) was added manganese dioxide (12 g), and the mixture was stirred at room temperature overnight. The manganese dioxide was filtered off and the filtrate was concentrated. The residue was subjected to silica gel column chromatography to give N-(1-ethyl-5-formyl-1H-pyrrol-3-yl)-N-methylthiophene-2-sulfonamide (9.5 g, yield 91%) as a yellow oil from a fraction eluted with ethyl acetate-hexane (1:1, volume ratio).

$^1$H-NMR (CDCl$_3$) δ: 1.31 (3H, t, J=7.5 Hz), 3.14 (3H, s), 4.32 (2H, q, J=7.5 Hz), 6.58 (1H, s), 7.02 (1H, s), 7.09 (1H, dd, J=5.1 Hz, 3.6 Hz), 7.40 (1H, dd, J=3.6 Hz, 1.2 Hz), 7.59 (1H, dd, J.=5.1 Hz, 1.2 Hz), 9.41 (1H, s).

Reference Example 16 ethyl 1-benzyl-4-nitro-1H-pyrrole-2-carboxylate

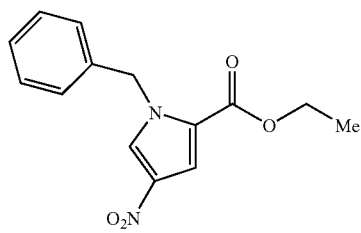 [SMILES: CCOC(=O)c1cc([N+](=O)[O-])cn1Cc1ccccc1]

To a solution of ethyl 4-nitro-1H-pyrrole-2-carboxylate (10 g) in N,N-dimethylformamide (100 mL) was slowly added sodium hydride (60%, oily, 2.4 g) at 0° C., and the mixture was stirred at room temperature for 30 min. Benzylbromide (8.0 mL) was slowly added to the reaction mixture, and the mixture was stirred at room temperature for 2 hr. Water was added to the reaction mixture, and the mixture was extracted with ethyl acetate. The ethyl acetate layer was washed with saturated brine, dried (MgSO$_4$) and concentrated. The obtained residue was subjected to silica gel column chromatography to give ethyl 1-benzyl-4-nitro-1H-pyrrole-2-carboxylate (14.3 g, yield 97%) as yellow crystals from a fraction eluted with ethyl acetate-hexane (1:3, volume ratio). melting point 73° C.

Reference Example 17 ethyl 1-benzyl-4-[(2-thienylsulfonyl)amino]-1H-pyrrole-2-carboxylate

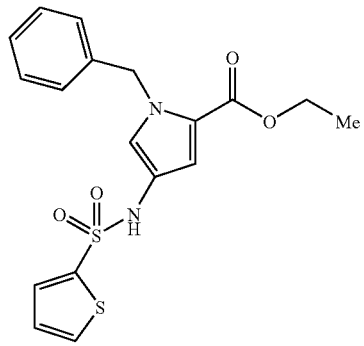 [SMILES: CCOC(=O)c1cc(NS(=O)(=O)c2cccs2)cn1Cc1ccccc1]

A mixture of ethyl 1-benzyl-4-nitro-1H-pyrrole-2-carboxylate (14.3 g) and 10% palladium-carbon (50% containing water, 1.5 g) in tetrahydrofuran (100 mL)-ethanol (100 mL) was stirred at room temperature for 12 hr under a hydrogen atmosphere. The catalyst was filtered off, and the filtrate was concentrated under reduced pressure. The obtained residue was subjected to silica gel column chromatography to give a brown oil from a fraction eluted with ethyl acetate-hexane (1:3, volume ratio). To a mixture of the oil and pyridine (100 mL) was added 2-thiophenesulfonyl chloride (10 g) at 0° C., and the mixture was stirred at room temperature for 2 hr. The reaction mixture was concentrated, water was added, and the mixture was extracted with ethyl acetate. The ethyl acetate layer was washed with saturated brine, dried (MgSO$_4$) and concentrated. The residue was subjected to silica gel column chromatography to give ethyl 1-benzyl-4-[(2-thienylsulfonyl)amino]-1H-pyrrole-2-carboxylate (19.5 g, yield 96%) as a brown oil from a fraction eluted with ethyl acetate-hexane (1:3, volume ratio).

$^1$H-NMR (CDCl$_3$) δ: 1.24 (3H, t, J=7.2 Hz), 4.18 (2H, q, J=7.2 Hz), 5.48 (2H, s), 6.24 (1H, s), 6.68 (1H, d, J=2.4 Hz), 6.90 (1H, d, J=2.4 Hz), 7.00-7.05 (3H, m), 7.25-7.29 (3H, m), 7.45 (1H, dd, J=3.9 Hz, 1.5 Hz), 7.54 (1H, dd, J=5.1 Hz, 1.5 Hz).

Reference Example 18

N-(1-benzyl-5-formyl-1H-pyrrol-3-yl)-N-methylthiophene-2-sulfonamide

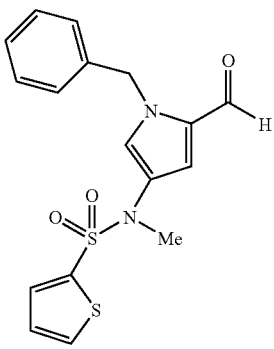 [SMILES: CN(c1cc(C=O)n(Cc2ccccc2)c1)S(=O)(=O)c1cccs1]

To a solution of ethyl 1-benzyl-4-[(2-thienylsulfonyl)amino]-1H-pyrrole-2-carboxylate (19.5 g) in N,N-dimethylformamide (100 mL) was slowly added sodium hydride (60%, oily, 2.2 g) at 0° C., and the mixture was stirred at room temperature for 30 min. Methyl iodide (3.4 mL) was added to the reaction mixture, and the mixture was stirred at room temperature for 1 hr. Water was added to the reaction mixture, and the mixture was extracted with ethyl acetate. The ethyl acetate layer was washed with saturated brine, dried (MgSO$_4$) and concentrated. The residue was subjected to silica gel column chromatography to give a yellow oil from a fraction eluted with ethyl acetate-hexane (1:1, volume ratio). To a solution of the yellow oil in tetrahydrofuran (150 mL) was slowly added lithium aluminum hydride (2.2 g) in small portions. The reaction mixture was stirred at room temperature for 1 hr, and water (2.2 mL), 15% aqueous sodium hydroxide solution (2.2 mL) and water (6.6 mL) were successively added to the reaction mixture under ice-cooling. The reaction mixture was stirred for 1 hr, and the insoluble material was filtered off. The filtrate was concentrated, manganese dioxide (30 g) was added to a solution of the residue in tetrahydrofuran (200 mL), and the mixture was stirred at room temperature overnight. The manganese dioxide was filtered off and the filtrate was concentrated. The residue was subjected to silica gel column chromatography to give N-(1-benzyl-5-formyl-1H-pyrrol-3-yl)-N-methylthiophene-2-sulfonamide (10.3 g, yield 57%) as a yellow oil from a fraction eluted with ethyl acetate-hexane (1:1, volume ratio).

$^1$H-NMR (CDCl$_3$) δ: 3.14 (3H, s), 5.51 (2H, s), 6.67 (1H, d, J=1.8 Hz), 7.00-7.15 (4H, m), 7.26-7.37 (4H, m), 7.55 (1H, dd, J=5.1 Hz, 1.2 Hz), 9.44 (1H, s).

Reference Example 19

({[2,2-dimethoxy-1-(nitromethyl)ethyl]thio}methyl)benzene

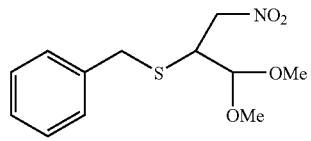 [SMILES: COC(OC)C(C[N+](=O)[O-])SCc1ccccc1]

A solution of (1E)-3,3-dimethoxy-1-nitroprop-1-ene (3.03 g, prepared according to Tetrahedron 2002, 58, 5773-5778), benzyl mercaptan (2.54 mL) and piperidine (0.25 mL) in toluene (20 mL) was stirred at room temperature for 48 hr. Water was added to the reaction mixture, and the mixture was extracted with ethyl acetate. The extract was washed with saturated brine, dried over anhydrous magnesium sulfate and concentrated under reduced pressure. The residue was purified by silica gel column chromatography (ethyl acetate:hexane=0:100-20:80) to give the title compound (4.78 g, yield 86%) as a yellow oil.

$^1$H-NMR (CDCl$_3$) δ: 3.27 (3 H, s), 3.37 (3 H, s), 3.39-3.47 (1 H, m), 3.74-3.87 (2 H, m), 4.19 (1 H, d, J=3.8 Hz), 4.38 (1 H, dd, J=13.8, 7.9 Hz), 4.68 (1 H, dd, J=13.8, 5.7 Hz), 7.24-7.37 (5 H, m).

Reference Example 20

2-(benzylthio)-3,3-dimethoxypropan-1-amine

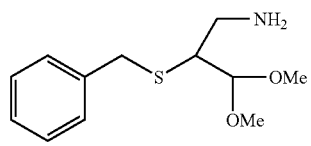

To a suspension of lithium aluminum hydride (13.0 g) in tetrahydrofuran (60 mL) was added dropwise a solution (76 mL) of ({[2,2-dimethoxy-1-(nitromethyl)ethyl]thio}methyl)benzene (18.6 g) in tetrahydrofuran at 0° C. The reaction mixture was warmed to room temperature, and stirred at room temperature for 1 hr. Water and 2N aqueous sodium hydroxide solution were added to the reaction mixture, and the mixture was diluted with ethyl acetate. The mixture was filtered through celite, and the filtrate was concentrated under reduced pressure. The residue was purified by NH silica gel column chromatography (ethyl acetate:hexane=30:70-100:0) to give the title compound (12.6 g, yield 76%) as a yellow oil.

$^1$H-NMR (CDCl$_3$) δ: 2.63-2.78 (2 H, m), 2.86-2.94 (1 H, m), 3.37 (3 H, s), 3.38 (3 H, s), 3.75-3.87 (2 H, m), 4.31 (1 H, d, J=5.5 Hz), 7.20-7.40 (5 H, m).

Reference Example 21 tert-butyl 4-(benzylthio)-4-(nitromethyl)piperidine-1-carboxylate

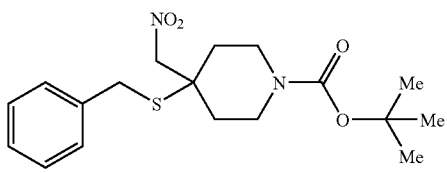 [SMILES: CC(C)(C)OC(=O)N1CCC(CN)(SCc2ccccc2)CC1]

A mixture of tert-butyl 4-oxopiperidine-1-carboxylate (1.00 g), benzyl mercaptan (2.48 g), nitromethane (3.05 g), ethylenediamine (0.3 g) and acetonitrile (15 mL) was heated under reflux for 8 hr. The reaction solution was concentrated under, reduced pressure, and the obtained residue was purified by silica gel column chromatography (ethyl acetate:hexane=1:9-3:1) to give the title compound (1.3 g, yield 71%) as colorless crystals.

$^1$H-NMR (CDCl$_3$) δ: 1.45 (9H, s), 1.79 (4H, q, J=3.7 Hz), 3.13-3.37 (2H, m), 3.72 (2H, m), 3.80-4.00 (2H, m), 4.51 (2H, s), 7.20-7.45 (5H, m).

Reference Example 22 tert-butyl 4-(aminomethyl)-4-(benzylthio)piperidine-1-carboxylate

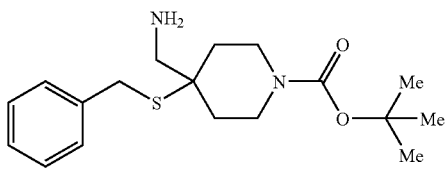

To a mixture of lithium aluminum hydride (0.4 g) and diethyl ether (20 mL) was added a solution of tert-butyl 4-(benzylthio)-4-(nitromethyl)piperidine-1-carboxylate (1.28 g) in diethyl ether (5 mL) at 0° C. The reaction mixture was heated under reflux for 1 hr. Ethyl acetate was added to decompose excess lithium aluminum hydride, and then water was added. The reaction mixture was diluted with a mixed solvent of tetrahydrofuran and ethyl acetate, and the inorganic salt was removed by filtration. The filtrate was washed with saturated brine, dried (MgSO$_4$) and concentrated. The obtained residue was subjected to silica gel column chromatography to give the title compound (0.33 g, yield 28%) as a colorless oil from a fraction eluted with ethyl acetate-methanol (2:1, volume ratio).

$^1$H-NMR (CDCl$_3$) δ: 1.35-1.80 (13H, s), 2.66 (2H, s), 3.17-3.37 (2H, m), 3.60 (2H, s), 3.65-3.92 (2H, m), 7.16-7.45 (5H, m).

Example 1 ethyl 3-benzyl-2-methyl-3,4-dihydropyrrolo[2,3-d]imidazole-5-carboxylate

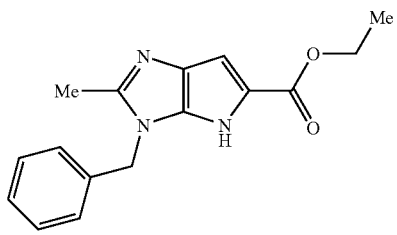 [SMILES: CCOC(=O)c1cc2nc(C)n(Cc3ccccc3)c2[nH]1]

To a solution (50 mL) of sodium ethoxide (5.4 g) in ethanol was added dropwise a mixture of 1-benzyl-2-methyl-1H-imidazole-4-carbaldehyde (3.8 g) and ethyl azidoacetate (10.3 g) under ice-cooling. After the completion of the dropwise addition, the mixture was stirred for 1 hr. Saturated aqueous ammonium chloride solution was added to the reaction mixture, and the mixture was concentrated. The obtained residue was extracted with ethyl acetate. The ethyl acetate layer was is washed with saturated brine, dried (MgSO$_4$) and concentrated. The obtained residue was dissolved in toluene (50 mL), and the mixture was stirred at 110° C. for 2 hr. The reaction mixture was concentrated, and the residue was subjected to silica gel column chromatography to give ethyl 3-benzyl-2-methyl-3,4-dihydropyrrolo[2,3-d]imidazole-5-carboxylate (0.35 g, yield 6.5%) as colorless crystals from a fraction eluted with ethyl acetate-hexane (1:1, volume ratio). melting point 193° C.

$^1$H-NMR (DMSO-d$_6$) δ: 1.28 (3H, t, J=7.2 Hz), 2.31 (3H, s), 4.23 (2H, q, J=7.2 Hz), 5.33 (2H, s), 6.69 (1H, s), 7.08-7.19 (2H, m), 7.22-7.43 (3H, m), 11.80 (1H, s).

Example 2 ethyl 3-{[(benzyloxy)carbonyl](methyl)amino}-2-methyl-4H-thieno[3,2-b]pyrrole-5-carboxylate

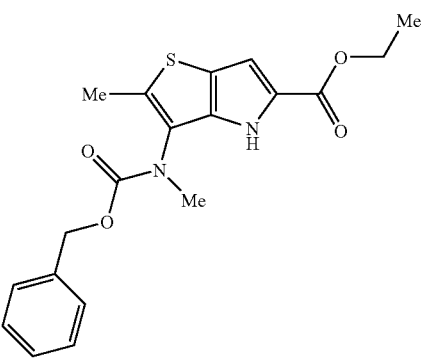 [SMILES: CCOC(=O)c1cc2sc(C)c(N(C)C(=O)OCc3ccccc3)c2[nH]1]

To a solution (20 mL) of sodium ethoxide (0.68 g) in ethanol was added dropwise a mixture of benzyl (5-formyl- 2-methyl-3-thienyl)methylcarbamate (0.72 g) and ethyl azidoacetate (1.3 g) under ice-cooling. After the completion of the dropwise addition, the mixture was stirred for 1 hr. Saturated aqueous ammonium chloride solution was added to the reaction mixture, and the mixture was concentrated. The obtained residue was extracted with ethyl acetate. The ethyl acetate layer was washed with saturated brine, dried (MgSO$_4$) and concentrated. The obtained residue was dissolved in toluene (20 mL), and the mixture was stirred at 110° C. for 2 hr. The reaction mixture was concentrated, and the residue was subjected to silica gel column chromatography to give ethyl 3-{[(benzyloxy)carbonyl](methyl)amino}-2-methyl-4H-thieno[3,2-b]pyrrole-5-carboxylate (91 mg, yield 10%) as colorless crystals from a fraction eluted with ethyl acetate-hexane (1:3, volume ratio). melting point 122° C.

Example 3 ethyl 2-methyl-3-[methyl(2-thienylsulfonyl)amino]-4H-thieno[3,2-b]pyrrole-5-carboxylate

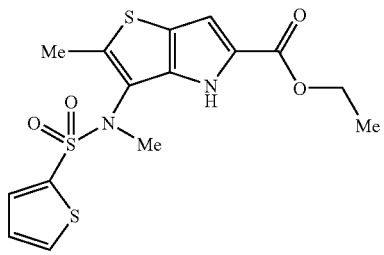 [SMILES: CCOC(=O)c1cc2sc(C)c(N(C)S(=O)(=O)c3cccs3)c2[nH]1]

To a solution (250 mL) of sodium ethoxide (17.2 g) in ethanol was added dropwise a mixture of N-(5-formyl-2-methyl-3-thienyl)-N-methylthiophene-2-sulfonamide (19 g) and ethyl azidoacetate (32.5 g) at −25° C. After the completion of the dropwise addition, the mixture was gradually warmed to room temperature. Saturated aqueous ammonium chloride solution was added to the reaction mixture, and the mixture was concentrated. The obtained residue was extracted with ethyl acetate. The ethyl acetate layer was washed with saturated brine, dried (MgSO$_4$) and concentrated. The obtained residue was subjected to silica gel column chromatography and a fraction eluted with ethyl acetate-hexane (1:1, volume ratio) was concentrated. The obtained yellow oil was dissolved in toluene (50 mL), and the mixture was stirred at 110° C. for 2 hr. The reaction mixture was concentrated, and the residue was subjected to silica gel column chromatography to give ethyl 2-methyl-3-[methyl(2-thienylsulfonyl)amino]-4H-thieno[3,2-b]pyrrole-5-carboxylate (6.54 g, yield 27%) as colorless crystals from a fraction eluted with ethyl acetate-hexane (1:3, volume ratio). melting point 161° C.

Example 4

2-methyl-3-[methyl(2-thienylsulfonyl)amino]-4H-thieno[3,2-b]pyrrole-5-carboxylic acid

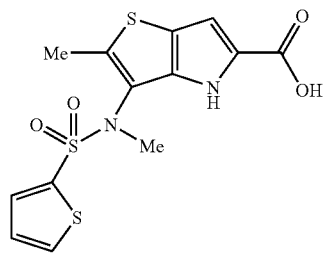 [SMILES: Cc1sc2cc(C(=O)O)[nH]c2c1N(C)S(=O)(=O)c1cccs1]

To a mixture of ethyl 2-methyl-3-[methyl(2-thienylsulfonyl)amino]-4H-thieno[3,2-b]pyrrole-5-carboxylate (8.39 g), tetrahydrofuran (50 mL) and ethanol (50 mL) was added 8N aqueous sodium hydroxide solution (10 mL), and the mixture was stirred at 60° C. overnight. The reaction mixture was concentrated, 6N hydrochloric acid was added to the obtained residue, and the mixture was extracted with ethyl acetate. The ethyl acetate layer was washed with saturated brine, dried (MgSO$_4$) and concentrated. Crystallization from diethyl ether gave 2-methyl-3-[methyl(2-thienylsulfonyl)amino]-4H-thieno[3,2-b]pyrrole-5-carboxylic acid (7.07 g, yield 91%) as brown crystals.

$^1$H-NMR (DMSO-d$_6$) δ: 2.01 (3H, s), 3.27 (3H, s), 6.94 (1H, s), 7.22 (1H, dd, J=5.1 Hz, 3.6 Hz), 7.59 (1H, dd, J=3.6 Hz, 1.5 Hz), 7.99 (1H, dd, J=5.1 Hz, 1.5 Hz), 11.64 (1H, brs), 12.44 (1H, brs).

Example 5

N-[5-(4,5-dihydro-1,3-thiazol-2-yl)-2-methyl-4H-thieno[3,2-b]pyrrol-3-yl]-N-methylthiophene-2-sulfonamide

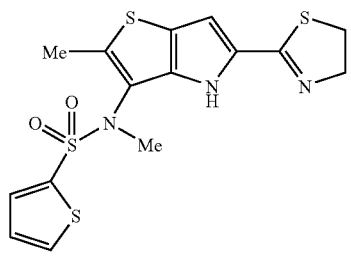 [SMILES: Cc1sc2cc(C3=NCCS3)[nH]c2c1N(C)S(=O)(=O)c1cccs1]

To a mixture of 2-methyl-3-[methyl(2-thienylsulfonyl)amino]-4H-thieno[3,2-b]pyrrole-5-carboxylic acid (0.35 g), 2-(tritylthio)ethaneamine hydrochloride (0.43 g), 1H-1,2,3-benzotriazol-1-ol (0.19 g), triethylamine (0.2 mL) and N,N-dimethylformamide (10 mL) was added N-[3-(dimethylamino)propyl]-N'-ethylcarbodiimide hydrochloride (0.23 g), and the mixture was stirred at room temperature overnight. Water was added to the reaction mixture, and the mixture was extracted with ethyl acetate. The ethyl acetate layer was washed with saturated brine, dried (MgSO$_4$) and concentrated to give a colorless oil. To a solution of triphenylphosphine oxide (0.83 g) in dichloromethane (20 mL) was slowly added trifluoromethanesulfonic anhydride (0.25 mL) at 0° C., the mixture was stirred for 10 min. The colorless oil was added to the mixture and the mixture was stirred at room temperature for 3 hr and concentrated. Saturated aqueous sodium hydrogen carbonate was added, and the mixture was extracted with ethyl acetate. The ethyl acetate layer was washed with saturated brine, dried (MgSO$_4$) and concentrated. The residue was subjected to silica gel column chromatography to give N-[5-(4,5-dihydro-1,3-thiazol-2-yl)-2-methyl-4H-thieno[3,2-b]pyrrol-3-yl]-N-methylthiophene-2-sulfonamide (111 mg, yield 29%) as colorless crystals from a fraction eluted with ethyl acetate-hexane (1:20→1:1, volume ratio). melting point 140° C.

$^1$H-NMR (DMSO-d$_6$) δ: 1.99 (3H, s), 3.26 (3H, s), 3.39 (2H, q, J=8.1 Hz), 4.31 (2H, q, J=8.1 Hz), 6.73 (1H, d, J=1.7 Hz), 7.22 (1H, dd, J=4.9 Hz, 3.8 Hz), 7.60 (1H, dd, J=3.8 Hz, 1.3 Hz), 7.99 (1H, dd, J=5.0 Hz, 1.3 Hz), 11.69 (1H, brs).

Example 6

N-{[4-(benzylthio)piperidin-4-yl]methyl}-2-methyl-3-[methyl(2-thienylsulfonyl)amino]-4H-thieno[3,2-b]pyrrole-5-carboxamide

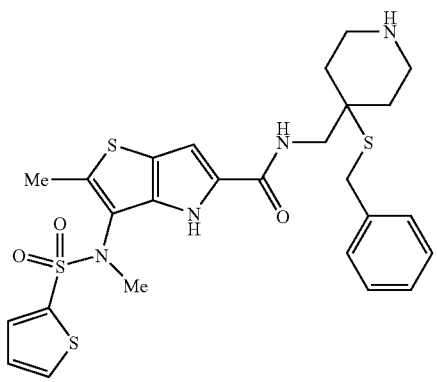 [SMILES: Cc1sc2cc(C(=O)NCC3(SCc4ccccc4)CCNCC3)[nH]c2c1N(C)S(=O)(=O)c1cccs1]

To a mixture of 2-methyl-3-[methyl(2-thienylsulfonyl)amino]-4H-thieno[3,2-b]pyrrole-5-carboxylic acid (1.0 g), tert-butyl 4-(aminomethyl)-4-(benzylthio)piperidine-1-carboxylate (944 mg), 1H-1,2,3-benzotriazol-1-ol (0.6 g), tetrahydrofuran (20 mL) and acetonitrile (20 mL) was added N-[3-(dimethylamino)propyl]-N'-ethylcarbodiimide hydrochloride (0.8 g), and the mixture was stirred at room temperature for 30 min. Saturated aqueous sodium hydrogen carbonate solution was added to the reaction mixture, and the mixture was extracted with ethyl acetate. The ethyl acetate layer was washed with saturated brine, dried (MgSO$_4$) and concentrated to give a colorless oil. To a solution of triphenylphosphine oxide (2.34 g) in acetonitrile (20 mL) was slowly added trifluoromethanesulfonic anhydride (0.71 mL) at 0° C., the mixture was stirred for 10 min, and the colorless oil was added. The reaction mixture was stirred at room temperature for 3 hr and concentrated. Saturated aqueous sodium hydrogen carbonate was added thereto, and the mixture was extracted with ethyl acetate. The ethyl acetate layer was washed with saturated brine, dried (MgSO$_4$) and concentrated. The residue was subjected to silica gel column chromatography to give N-{[4-(benzylthio)piperidin-4-yl]methyl}-2-methyl-3-[methyl(2-thienylsulfonyl)amino]-4H-thieno[3,2-b]pyrrole-5-carboxamide (1.03 g, yield 79%) as colorless crystals from a fraction eluted with ethyl acetate-hexane (1:20→1:1, volume ratio). melting point 222° C.

Example 7

N-methyl-N-[2-methyl-5-(1-thia-3,8-diazaspiro[4.5]deca-2-en-2-yl)-4H-thieno[3,2-b]pyrrol-3-yl]thiophene-2-sulfonamide

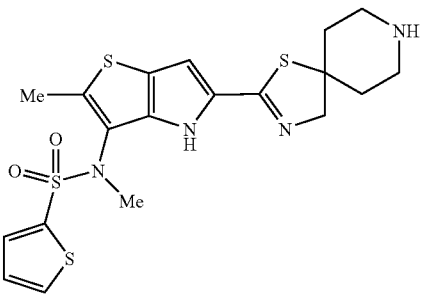 [SMILES: Cc1sc2cc(C3=NCC4(CCNCC4)S3)[nH]c2c1N(C)S(=O)(=O)c1cccs1]

To a solution of triphenylphosphine oxide (1.5 g) in dichloromethane (20 mL) was slowly added trifluoromethanesulfonic anhydride (0.45 mL) at 0° C., and the mixture was stirred for 10 min. N-{[4-(Benzylthio)piperidin-4-yl]methyl}-2-methyl-3-[methyl(2-thienylsulfonyl)amino]-4H-thieno[3,2-b]pyrrole-5-carboxamide (1.03 g) was added, and the mixture was stirred at room temperature for 3 hr and concentrated. Saturated aqueous sodium hydrogen carbonate was added, and the mixture was extracted with ethyl acetate. The ethyl acetate layer was washed with saturated brine, dried (MgSO$_4$) and concentrated. The residue was subjected to silica gel column chromatography to give N-methyl-N-[2-methyl-5-(1-thia-3,8-diazaspiro[4.5]deca-2-en-2-yl)-4H-thieno[3,2-b]pyrrol-3-yl]thiophene-2-sulfonamide (240 mg, yield 29%) as colorless crystals from a fraction eluted with ethyl acetate-hexane (1:1, volume ratio). melting point 196° C.

Example 8

N-[5-(8-acetyl-1-thia-3,8-diazaspiro[4.5]deca-2-en-2-yl)-2-methyl-4H-thieno[3,2-b]pyrrol-3-yl]-N-methylthiophene-2-sulfonamide

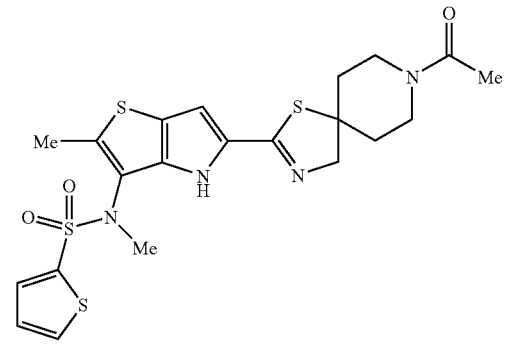 [SMILES: CC(=O)N1CCC2(CC1)CN=C(c1cc3sc(C)c(N(C)S(=O)(=O)c4cccs4)c3[nH]1)S2]

To a mixture of N-methyl-N-[2-methyl-5-(1-thia-3,8-diazaspiro[4.5]deca-2-en-2-yl)-4H-thieno[3,2-b]pyrrol-3-yl]thiophene-2-sulfonamide (180 mg), triethylamine (78 μL)

and tetrahydrofuran (5 mL) was added acetyl chloride (32 μL), and the mixture was stirred at room temperature for 10 min. The reaction mixture was concentrated, 1N hydrochloric acid was added, and the mixture was extracted with ethyl acetate. The ethyl acetate layer was washed with saturated brine, dried (MgSO$_4$) and concentrated. The residue was subjected to silica gel column chromatography to give N-[5-(8-acetyl-1-thia-3,8-diazaspiro[4.5]deca-2-en-2-yl)-2-methyl-4H-thieno[3,2-b]pyrrol-3-yl]-N-methylthiophene-2-sulfonamide (115 mg, yield 57%) as colorless crystals from a fraction eluted with ethyl acetate-hexane (1:1, volume ratio). melting point 231° C.

$^1$H-NMR (DMSO-d$_6$) δ: 1.65-1.80 (1H, m), 1.81-1.93 (3H, m), 1.97 (3H, s), 2.02 (3H, s), 2.71-2.91 (1H, m), 3.07-3.23 (1H, m), 3.26 (3H, s), 3.70-3.95 (1H, m), 4.11 (2H, s), 4.15-4.30 (1H, m), 6.72 (1H, s), 7.22 (1H, dd, J=4.9 Hz, 3.8 Hz), 7.59 (1H, dd, J=3.8 Hz, 1.3 Hz), 7.99 (1H, dd, J=4.9 Hz, 1.3 Hz), 11.68 (1H, s).

Example 9 ethyl [2-({2-methyl-3-[methyl(2-thienylsulfonyl)amino]-4H-thieno[3,2-b]pyrrol-5-yl}carbonyl)hydrazino](oxo)acetate

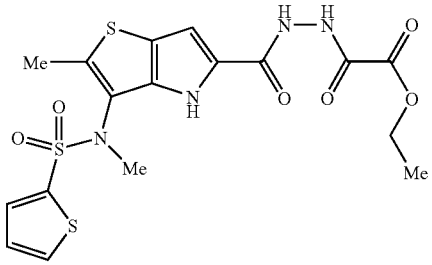 [SMILES: CCOC(=O)C(=O)NNC(=O)c1cc2sc(C)c(N(C)S(=O)(=O)c3cccs3)c2[nH]1]

To a mixture of 2-methyl-3-[methyl(2-thienylsulfonyl)amino]-4H-thieno[3,2-b]pyrrole-5-carboxylic acid (2.0 g), hydrazine monohydrate (2 mL), 1H-1,2,3-benzotriazol-1-ol (920 mg), tetrahydrofuran (20 mL) and acetonitrile (20 mL) was added N-[3-(dimethylamino)propyl]-N'-ethylcarbodiimide hydrochloride (1.15 g), and the mixture was stirred at room temperature for 30 min. Saturated aqueous sodium hydrogen carbonate solution was added to the reaction mixture, and the mixture was extracted with ethyl acetate. The ethyl acetate layer was washed with saturated brine, dried (MgSO$_4$) and concentrated to give a colorless oil. The colorless oil was dissolved in N,N-dimethylacetamide (10 mL), and ethyl 3-chloro-3-oxopropanoate (0.67 mL) was added. The reaction mixture was stirred at room temperature for 1 hr, 1N hydrochloric acid was added, and the mixture was extracted with ethyl acetate. The ethyl acetate layer was washed with saturated brine, dried (MgSO$_4$) and concentrated. Crystallization from diethyl ether gave ethyl [2-({2-methyl-3-[methyl(2-thienylsulfonyl)amino]-4H-thieno[3,2-b]pyrrol-5-yl}carbonyl)hydrazino](oxo)acetate (1.7 g, yield 65%) as colorless crystals. melting point 135° C.

Example 10 ethyl 5-{2-methyl-3-[methyl(2-thienylsulfonyl)amino]-4H-thieno[3,2-b]pyrrol-5-yl}-1,3,4-thiadiazole-2-carboxylate

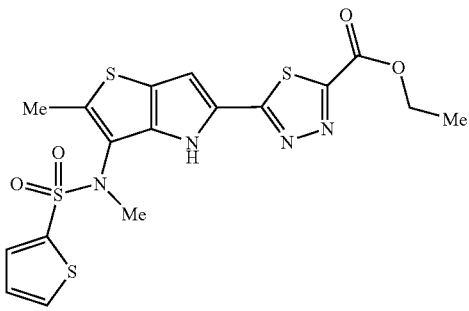 [SMILES: CCOC(=O)c1nnc(-c2cc3sc(C)c(N(C)S(=O)(=O)c4cccs4)c3[nH]2)s1]

To a solution of ethyl [2-({2-methyl-3-[methyl(2-thienylsulfonyl)amino]-4H-thieno[3,2-b]pyrrol-5-yl}carbonyl)hydrazino](oxo)acetate (1.61 g) in tetrahydrofuran (20 mL) was added Lawesson reagent (1.38 g), and the mixture was stirred at 60° C. overnight. The reaction mixture was concentrated and crystallized from toluene and diethyl ether to give ethyl 5-{2-methyl-3-[methyl(2-thienylsulfonyl)amino]-4H-thieno[3,2-b]pyrrol-5-yl}-1,3,4-thiadiazole-2-carboxylate (1.31 g, yield 82%) as yellow crystals. melting point 209° C.

Example 11

N-{5-[5-(hydroxymethyl)-1,3,4-thiadiazol-2-yl]-2-methyl-4H-thieno[3,2-b]pyrrol-3-yl}-N-methylthiophene-2-sulfonamide

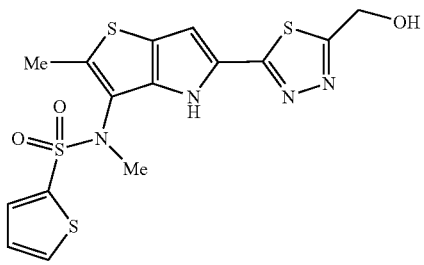 [SMILES: Cc1sc2cc(-c3nnc(CO)s3)[nH]c2c1N(C)S(=O)(=O)c1cccs1]

To a solution of ethyl 5-{2-methyl-3-[methyl(2-thienylsulfonyl)amino]-4H-thieno[3,2-b]pyrrol-5-yl}-1,3,4-thiadiazole-2-carboxylate (1.3 g) in tetrahydrofuran (20 mL) was slowly added lithium aluminum hydride (114 mg) in small portions. The mixture was stirred at room temperature for 1 hr, and water (0.15 mL), 15% aqueous sodium hydroxide solution (0.15 mL) and water (0.45 mL) were successively added to the reaction mixture under ice-cooling. The mixture was stirred for 1 hr, and the insoluble material was filtered off. The filtrate was concentrated and crystallized from diethyl ether to give N-{5-[5-(hydroxymethyl)-1,3,4-thiadiazol-2-yl]-2-methyl-4H-thieno[3,2-b]pyrrol-3-yl}-N-methylthiophene-2-sulfonamide (370 mg, yield 31%) as brown crystals.

Example 12

N-{5-[5-(dimethoxymethyl)-4,5-dihydro-1,3-thiazol-2-yl]-2-methyl-4H-thieno[3,2-b]pyrrol-3-yl}-N-methylthiophene-2-sulfonamide

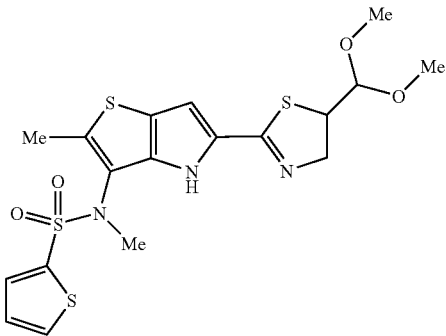 [SMILES: COC(OC)C1CN=C(c2cc3sc(C)c(N(C)S(=O)(=O)c4cccs4)c3[nH]2)S1]

To a mixture of 2-methyl-3-[methyl(2-thienylsulfonyl)amino]-4H-thieno[3,2-b]pyrrole-5-carboxylic acid (1.0 g), 2-(benzylthio)-3,3-dimethoxypropan-1-amine (720 mg), 1H-1,2,3-benzotriazol-1-ol (450 mg), tetrahydrofuran (10 mL) and acetonitrile (10 mL) was added N-[3-(dimethylamino)propyl]-N'-ethylcarbodiimide hydrochloride (570 mg), and the mixture was stirred at room temperature for 30 min. Saturated aqueous sodium hydrogen carbonate solution was added to the reaction mixture, and the mixture was extracted with ethyl acetate. The ethyl acetate layer was washed with saturated brine, dried (MgSO$_4$) and concentrated to give a colorless oil. To a solution of triphenylphosphine oxide (252 mg) in dichloromethane (3 mL) was slowly added trifluoromethanesulfonic anhydride (76 µL) at 0° C., the mixture was stirred for 10 min, and the colorless oil was added. The mixture was stirred at room temperature for 3 hr and concentrated. Saturated aqueous sodium hydrogen carbonate was added, and the mixture was extracted with ethyl acetate. The ethyl acetate layer was washed with saturated brine, dried (MgSO$_4$) and concentrated. The residue was subjected to silica gel column chromatography to give N-{5-[5-(dimethoxymethyl)-4,5-dihydro-1,3-thiazol-2-yl]-2-methyl-4H-thieno[3,2-b]pyrrol-3-yl}-N-methylthiophene-2-sulfonamide (245 mg, yield 27%) as colorless crystals from a fraction eluted with ethyl acetate-hexane (1:1, volume ratio). melting point 185° C.

Example 13

N-methoxy-N,2-dimethyl-3-[methyl(2-thienylsulfonyl)amino]-4H-thieno[3,2-b]pyrrole-5-carboxamide

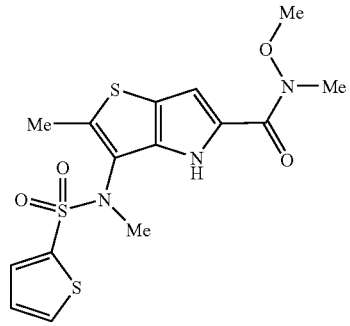 [SMILES: CON(C)C(=O)c1cc2sc(C)c(N(C)S(=O)(=O)c3cccs3)c2[nH]1]

To a mixture of 2-methyl-3-[methyl(2-thienylsulfonyl)amino]-4H-thieno[3,2-b]pyrrole-5-carboxylic acid (0.30 g), N-methoxymethylamine hydrochloride (100 mg), 1H-1,2,3-benzotriazol-1-ol (150 mg), triethylamine (0.15 mL) and N,N-dimethylformamide (10 mL) was added N-[3-(dimethylamino)propyl]-N'-ethylcarbodiimide hydrochloride (190 mg), and the mixture was stirred at room temperature overnight. Water was added to the reaction mixture, and the mixture was extracted with ethyl acetate. The ethyl acetate layer was washed with saturated brine, dried (MgSO$_4$) and concentrated. Crystallization from diethyl ether gave N-methoxy-N,2-dimethyl-3-[methyl(2-thienylsulfonyl)amino]-4H-thieno[3,2-b]pyrrole-5-carboxamide (262 mg, yield 80%) as colorless crystals. melting point 187° C.

Example 14

N-(5-acetyl-2-methyl-4H-thieno[3,2-b]pyrrol-3-yl)-N-methylthiophene-2-sulfonamide

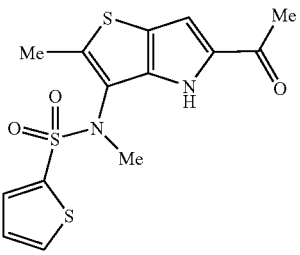 [SMILES: CC(=O)c1cc2sc(C)c(N(C)S(=O)(=O)c3cccs3)c2[nH]1]

To a solution of N-methoxy-N,2-dimethyl-3-[methyl(2-thienylsulfonyl)amino]-4H-thieno[3,2-b]pyrrole-5-carboxamide (230 mg) in N,N-dimethylformamide (5 mL) was added sodium hydride (60%, oily, 25 mg), and the mixture was stirred at room temperature for 30 min. Chloromethyl methyl ether (51 mg) was added to the reaction mixture, and the mixture was stirred at room temperature overnight. Water was added to the reaction mixture, and the mixture was extracted with ethyl acetate. The ethyl acetate layer was washed with saturated brine, dried (MgSO$_4$) and concentrated. The residue was dissolved in tetrahydrofuran (5 mL), methyl magnesium bromide (ca. 3.0M diethyl ether solution, 0.4 mL) was added thereto, and the mixture was stirred at room temperature for 30 min. Water was added to the reaction mixture, and the mixture was extracted with ethyl acetate. The ethyl acetate layer was washed with saturated brine, dried (MgSO$_4$) and concentrated. The residue was dissolved in tetrahydrofuran (5 mL), 6N hydrochloric acid (5.0°mL) was added thereto, and the mixture was stirred at 80° C. overnight. Water was added to the reaction mixture, and the mixture was extracted with ethyl acetate. The ethyl acetate layer was washed with saturated brine, dried (MgSO$_4$) and concentrated. The residue was subjected to silica gel column chromatography to give N-(5-acetyl-2-methyl-4H-thieno[3,2-b]pyrrol-3-yl)-N-methylthiophene-2-sulfonamide (55.2 mg, yield 26%) as gray crystals from a fraction eluted with ethyl acetate-hexane (1:1, volume ratio). melting point 220° C.

Example 15 ethyl 4-ethyl-6-[methyl(2-thienylsulfonyl)amino]-1,4-dihydropyrrolo[3,2-b]pyrrole-2-carboxylate

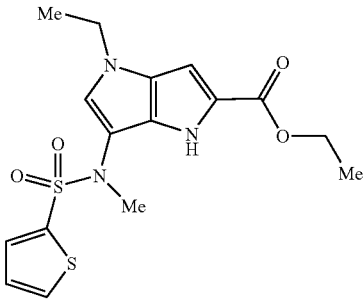 [SMILES: CCOC(=O)c1cc2c([nH]1)c(N(C)S(=O)(=O)c1cccs1)cn2CC]

To a solution (150 mL) of sodium ethoxide (8.3 g) in ethanol was added dropwise a mixture of N-(1-ethyl-5-formyl-1H-pyrrol-3-yl)-N-methylthiophene-2-sulfonamide (8.5 g) and ethyl azidoacetate (16.5 g) under ice-cooling. After the completion of the dropwise addition, the mixture was stirred for 2 hr. Saturated aqueous ammonium chloride solution was added to the reaction mixture, and the mixture was concentrated. The obtained residue was extracted with ethyl acetate. The ethyl acetate layer was washed with saturated brine, dried ($MgSO_4$) and concentrated. The obtained residue was subjected to silica gel column chromatography and eluted with ethyl acetate-hexane (1:1, volume ratio). The obtained yellow oil was dissolved in toluene (50 mL), and the mixture was stirred at 110° C. for 1 hr. The reaction mixture was concentrated, and the residue was subjected to silica gel column chromatography to give ethyl 4-ethyl-6-[methyl(2-thienylsulfonyl)amino]-1,4-dihydropyrrolo[3,2-b]pyrrole-2-carboxylate (1.12 g, yield 32%) as colorless crystals from a fraction eluted with ethyl acetate-hexane (1:1, volume ratio). melting point 122° C.

Example 16

4-ethyl-6-[methyl(2-thienylsulfonyl)amino]-1,4-dihydropyrrolo[3,2-b]pyrrole-2-carboxylic acid

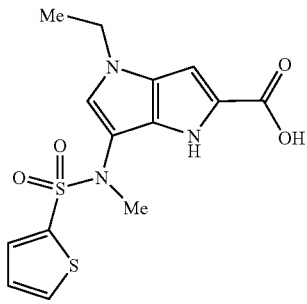 [SMILES: CCn1cc(N(C)S(=O)(=O)c2cccs2)c2[nH]c(C(=O)O)cc21]

To a mixture of ethyl 4-ethyl-6-[methyl(2-thienylsulfonyl)amino]-1,4-dihydropyrrolo[3,2-b]pyrrole-2-carboxylate (1.0 g), tetrahydrofuran (8 mL) and ethanol (8 mL) was added 8N aqueous sodium hydroxide solution (3 mL), and the mixture was stirred at room temperature for 4 days. The reaction mixture was concentrated, 6N hydrochloric acid was added to the obtained residue, and the mixture was extracted with ethyl acetate. The ethyl acetate layer was washed with saturated brine, dried ($MgSO_4$) and concentrated. The obtained residue was crystallized from diethyl ether to give 4-ethyl-6-[methyl(2-thienylsulfonyl)amino]-1,4-dihydropyrrolo[3,2-b]pyrrole-2-carboxylic acid (780 mg, yield 85%) as colorless crystals.

$^1$H-NMR (DMSO-$d_6$) δ: 1.30 (3H, t, J=7.5 Hz), 3.20 (3H, s), 3.92 (2H, q, J=7.5 Hz), 6.63 (1H, d, J=1.5 Hz), 6.87 (1H, s), 7.19 (1H, dd, J=3.9 Hz, 5.1 Hz), 7.59 (1H, dd, J=3.9 Hz, 1.5 Hz), 7.99 (1H, dd, J=5.1 Hz, 1.5 Hz), 10.63 (1H, brs), 12.08 (1H, brs).

Example 17

N-[5-(4,5-dihydro-1,3-thiazol-2-yl)-1-ethyl-1,4-dihydropyrrolo[3,2-b]pyrrol-3-yl]-N-methylthiophene-2-sulfonamide

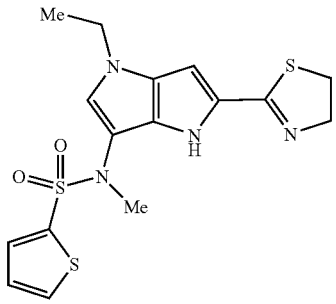 [SMILES: CCn1cc(N(C)S(=O)(=O)c2cccs2)c2[nH]c(C3=NCCS3)cc21]

To a mixture of 4-ethyl-6-[methyl(2-thienylsulfonyl)amino]-1,4-dihydropyrrolo[3,2-b]pyrrole-2-carboxylic acid (780 mg), 2-(tritylthio)ethaneamine hydrochloride (850 mg), 1H-1,2,3-benzotriazol-1-ol (370 mg), triethylamine (0.5 mL) and N,N-dimethylformamide (15 mL) was added N-[3-(dimethylamino)propyl]-N'-ethylcarbodiimide hydrochloride (460 mg), and the mixture was stirred at room temperature overnight. Water was added to the reaction mixture, and the mixture was extracted with ethyl acetate. The ethyl acetate layer was washed with saturated brine, dried ($MgSO_4$) and concentrated to give a colorless oil. To a solution of triphenylphosphine oxide (1.8 g) in dichloromethane (20 mL) was slowly added trifluoromethanesulfonic anhydride (555 μL) at 0° C., the mixture was stirred for 10 min, and the colorless oil was added. The reaction mixture was stirred at room temperature for 2 hr and concentrated. Saturated aqueous sodium hydrogen carbonate was added thereto, and the mixture was extracted with ethyl acetate. The ethyl acetate layer was washed with saturated brine, dried ($MgSO_4$) and concentrated. The residue was subjected to silica gel column chromatography to give N-[5-(4,5-dihydro-1,3-thiazol-2-yl)-1-ethyl-1,4-dihydropyrrolo[3,2-b]pyrrol-3-yl]-N-methylthiophene-2-sulfonamide (260 mg, yield 30%) as colorless crystals from a fraction eluted with ethyl acetate-hexane (1:20 to 1:3, volume ratio). melting point 163° C.

$^1$H-NMR (DMSO-$d_6$) δ: 1.30 (3H, t, J=7.3 Hz), 3.19 (3H, s), 3.35 (2H, t, J=8.0 Hz), 3.92 (2H, q, J=7.3 Hz), 4.27 (2H, t, J=8.0 Hz), 6.41 (1H, d, J=1.7 Hz), 6.79 (1H, s), 7.18 (1H, dd, J=3.8 Hz, 4.9 Hz), 7.47 (1H, dd, J=1.5 Hz, 3.8 Hz), 7.94 (1H, dd, J=5.1 Hz, 1.5 Hz), 10.45 (1H, brs).

Example 18 ethyl 4-benzyl-6-[methyl(2-thienylsulfonyl)amino]-1,4-dihydropyrrolo[3,2-b]pyrrole-2-carboxylate

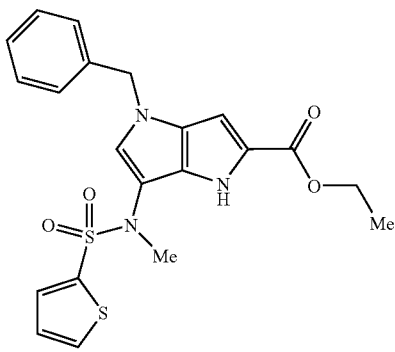 [SMILES: CCOC(=O)c1cc2c([nH]1)c(N(C)S(=O)(=O)c1cccs1)cn2Cc1ccccc1]

To a solution (150 mL) of sodium ethoxide (7.8 g) in ethanol was added dropwise a mixture of N-(1-benzyl-5-formyl-1H-pyrrol-3-yl)-N-methylthiophene-2-sulfonamide (10.3 g) and ethyl azidoacetate (15 g) under ice-cooling. After the completion of the dropwise addition, the mixture was stirred for 2 hr. Saturated aqueous ammonium chloride solution was added to the reaction mixture, and the mixture was concentrated. The obtained residue was extracted with ethyl acetate. The ethyl acetate layer was washed with saturated brine, dried ($MgSO_4$) and concentrated. The obtained residue was subjected to silica gel column chromatography and eluted with ethyl acetate-hexane (1:1, volume ratio). The obtained yellow oil was dissolved in toluene (50 mL), and the mixture was stirred at 110° C. for 1 hr. The reaction mixture was concentrated, and the residue was subjected to silica gel column chromatography, eluted with ethyl acetate-hexane (1:1, volume ratio) and concentrated to give ethyl 4-benzyl-6-[methyl(2-thienylsulfonyl)amino]-1,4-dihydropyrrolo[3,2-b]pyrrole-2-carboxylate (13 mg, yield 0.1%) as colorless crystals. melting point 120° C.

$^1$H-NMR ($CDCl_6$) δ: 1.26 (3H, t, J=7.2 Hz), 3.14 (3H, s), 4.20 (2H, q, J=7.2 Hz), 5.51 (2H, s), 6.72 (1H, d, J=2.1 Hz), 6.92 (1H, d, J=2.1 Hz), 7.02-7.12 (3H, m), 7.22-7.35 (3H, m), 7.37 (1H, dd, J=1.1 Hz, 3.8 Hz), 7.54 (1H, dd, J=1.1 Hz, 5.0 Hz), 9.91 (1H, brs).

Reference Example 1A

Construction of Glucokinase (GK) Expression Vector

Plasmid DNA to be used for the expression of a protein containing GST (Glutathione S-transferase) added to the amino terminal of human liver type GK in *Escherichia coli* (GST-hLGK1) was prepared as shown below.

First, PCR was performed using human liver cDNA (Clontech Laboratories, Inc. Marathon Ready cDNA) as a template and two kinds of synthetic DNAs (5'-CAGCTCTCCATC-CAAGCAGCCGTTGCT-3' (SEQ ID No:1) and 5'-GGCG-GCCTGGGTCCTGACAAG-3') (SEQ ID No:2). The obtained DNA fragment was cloned using a TOPO TA Cloning Kit (Invitrogen Corporation). PCR was performed using the obtained plasmid DNA as a template, a synthetic DNA (5'-GGATCCATGCCCAGACCAAGATC-CCAACTCCCACAACCCAACTCCCAGGTA-GAGCAGATCCTGG CAGAG-3') (SEQ ID No:3) with a BamHI site added to immediately before the initiation codon, and a synthetic DNA (5'-GAATTCCTGGCCCAGCATA-CAGGC-3') (SEQ ID No:4) with an EcoRI site added to immediately after the stop codon. The obtained DNA fragment was subcloned to pGEX6P-2 (Amersham Biosciences K.K.) cleaved with BamHI and EcoRI to give a plasmid (pGEX6P-2/hLGK1) for expression of human liver GK.

Reference Example 2A

Expression and Purification of GST-hLGK1

BL21 strain (Stratagene) transformed with pGEX6P-2/hLGK1 obtained in Reference Example 1A was cultured with shaking in 200 ml Erlenmeyer flask containing 100 μg/ml ampicillin-containing LB medium (50 ml) at 37° C. for 14 hr. The culture medium (25 ml) was diluted with 100 μg/ml ampicillin-containing LB medium (225 ml), and further cultured with shaking in 1 L Erlenmeyer flask at 37° C. for 1 hr. After culture, the Erlenmeyer flask was cooled on ice, 100 mM Isopropyl-Thio-β-D-Galactopyranoside (IPTG) (125 μL) was added (final concentration 50 μm), and the cells were cultured at 17° C. for 20 hr. The culture medium was centrifuged, and the obtained fungus was disrupted by ultrasonication and the object protein (GST-hLGK1) was purified from the supernatant using Glutathione Sepharose 4B (Amersham Biosciences).

Experimental Example 1

Determination of GK Activity Value

A solution (5 μL) of test compound in 50% dimethyl sulfoxide was added to each well of 384 well black plate (Nalge Nunc International K.K.). Then, a solution (35 μL) obtained by diluting GST-hLGK1 obtained in Reference Example 2A with measurement buffer (containing 50 mM HEPES (pH 7.4), 200 mM KCl, 5 mM $MgCl_2$, 2.5 mM DTT and 50 μM 2'-(or -3')—O—(N-methylanthraniloyl) adenosine 5'-triphosphate (Mant-ATP) (Jena Bioscience GmbH)) to 6 μg/mL was added to each well.

Each well was stood at 37° C. for 10 min, and 25 mM D-glucose solution (10 μL) was added to start the reaction.

Each well after the reaction was stood at 37° C. for 60 min, and the reaction was quenched by adding 25 μL of a quenching solution (containing 200 mM HEPES (pH 7.4), 20 mM $MgCl_2$, 200 mM EDTA, 0.03% Triton-X 100, 0.3% Coating 3 reagent (Caliper Life Sciences, Inc.)).

2'-(or -3')-O—(N-methylanthraniloyl)adenosine 5'-triphosphate (Mant-ATP, substrate) and Mant-ADP (reaction resultant product) were separated from each well after the reaction by a microchip type capillary electrophoresis apparatus 250 HTS (Caliper Life Sciences, Inc.). The reaction rate [(reaction resultant product peak height)/(reaction resultant product peak height+substrate peak height)×100(%)] was calculated from the ratio of the substrate peak height and reaction resultant product peak height obtained by fluorescence detection (excitation wavelength 355 nm, measurement wavelength 460 nm) and used as the index of GK activity.

As a control group, the reaction rate was calculated in the same manner as above except that "solution in 50% dimethyl sulfoxide (free of a test compound)" was used instead of "solution of test compound in 50% dimethyl sulfoxide".

Using the percentage obtained by subtracting the reaction rate of the control group from the reaction rate of the well added with the test compound (test compound addition group) as a GK activation value of the test compound, a concentration dependency curve of the test compound was drawn, and the concentration of the test compound at the middle point between the maximum activity value of the test compound addition group and the activity value of the control group was taken as an $EC_{50}$ value. The results are shown in Table 1.

TABLE 1

| test compound (Example No.) | $EC_{50}$ value (μM) |
|---|---|
| 1 | 3.6 |
| 5 | 0.074 |
| 8 | 0.16 |
| 17 | 0.35 |
| 18 | 0.43 |

As is clear from Table 1, the compound of the present invention has a superior glucokinase activating action.

Formulation Example 1

Production of Capsule

| | |
|---|---|
| 1) compound of Example 1 | 30 mg |
| 2) finely divided powder cellulose | 10 mg |
| 3) lactose | 19 mg |
| 4) magnesium stearate | 1 mg |
| total | 60 mg |

1), 2), 3) and 4) are mixed and filled in a gelatin capsule.

Formulation Example 2

Production of Tablet

| | |
|---|---|
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3), and 30 g of 4) are kneaded with water, vacuum dried and sized.

The sized powder is mixed with 14 g of 4) and 1 g of 5), and the mixture is punched by a tabletting machine. In this way, 1000 tablets containing 30 mg of the compound of Example 1 per tablet are obtained.

Industrial Applicability

The glucokinase activator of the present invention has a superior activity and is useful as a pharmaceutical agent such as an agent for the prophylaxis or treatment of diabetes, obesity and the like, and the like.

This application is based on patent application No. 2006-284418 filed in Japan, and the contents disclosed therein are hereby entirely incorporated by reference. In addition, the patent documents and non-patent documents cited in the present is specification are hereby incorporated in their entireties by reference, to the extent that they have been disclosed in the present specification.

The invention claimed is:

1. A compound represented by the formula (I):

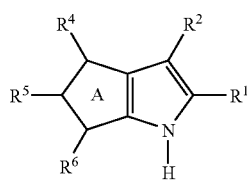

wherein ring A is a 5-membered ring, $R^1$ is an optionally substituted 5- to 7-membered heterocyclic group or —$COR^3$ wherein $R^3$ is an optionally substituted hydrocarbon group, an optionally substituted hydroxy group, an optionally substituted amino group or an optionally substituted heterocyclic group, $R^2$ is a hydrogen atom or a halogen atom, $R^4$ and $R^5$ are each independently a hydrogen atom or a substituent (provided that $R^4$ and $R^5$ are absent when on an atom in ring A the chemical valency does not allow for bonding of a substituent), $R^6$ is an optionally substituted amino group, or a salt thereof.

2. The compound or salt of claim 1, wherein ring A is 5-membered aromatic heterocycle.

3. The compound or salt of claim 1, wherein $R^1$ is an optionally substituted 5- to 7-membered heterocyclic group.

4. The compound or salt of claim 1, wherein $R^2$ is a hydrogen atom.

5. The compound or salt of claim 1, wherein $R^4$ is an optionally substituted hydrocarbon group.

6. The compound or salt of claim 1, wherein $R^5$ is a hydrogen atom or an optionally substituted hydrocarbon group.

7. N-[5-(4,5-dihydro-1,3-thiazol-2-yl)-2-methyl-4H-thieno[3,2-b]pyrrol-3-yl]-N-methylthiophen-2-sulfonamide, N-[5-(8-acetyl-1-thia-3,8-diazaspiro[4.5]deca-2-en-2-yl)-2-methyl-4H-thieno[3,2-b]pyrrol-3-yl]-N-methylthiophen-2-sulfonamide, N-[5-(4,5-dihydro-1,3-thiazol-2-yl)-1-ethyl-1,4-dihydropyrrolo[3,2-b]pyrrol-3-yl]-N-methylthiophen-2-sulfonamide or ethyl 4-benzyl-6-[methyl(2-thienylsulfonyl)amino]-1,4-dihydropyrrolo[3,2-b]pyrrol-2-carboxylate, or a salt thereof.

8. A pharmaceutical composition comprising the compound or salt of claim 1 and a pharmaceutically acceptable carrier.

9. A method of treating diabetes in a mammal having diabetes, comprising administering the compound or salt of claim 1 to the mammal.

* * * * *

SEQUENCE LISTING

```
<160> NUMBER OF SEQ ID NOS: 4

<210> SEQ ID NO 1
<211> LENGTH: 27
<212> TYPE: DNA
<213> ORGANISM: Artificial
<220> FEATURE:
<223> OTHER INFORMATION: primer for cloning glucokinase

<400> SEQUENCE: 1
cagctctcca tccaagcagc cgttgct                                    27

<210> SEQ ID NO 2
<211> LENGTH: 21
<212> TYPE: DNA
<213> ORGANISM: Artificial
<220> FEATURE:
<223> OTHER INFORMATION: primer for cloning glucokinase

<400> SEQUENCE: 2
ggcggcctgg gtcctgacaa g                                          21

<210> SEQ ID NO 3
<211> LENGTH: 60
<212> TYPE: DNA
<213> ORGANISM: Artificial
<220> FEATURE:
<223> OTHER INFORMATION: primer for cloning glucokinase

<400> SEQUENCE: 3
```

```
ggatccatgc ccagaccaag atcccaactc ccacaaccca actcccaggt agagcagatc    60

<210> SEQ ID NO 4
<211> LENGTH: 24
<212> TYPE: DNA
<213> ORGANISM: Artificial
<220> FEATURE:
<223> OTHER INFORMATION: primer for cloning glucokinase

<400> SEQUENCE: 4
gaattcctgg cccagcatac aggc                                          24
```